United States Patent
Mori et al.

(10) Patent No.: US 7,115,717 B2
(45) Date of Patent: Oct. 3, 2006

(54) ANTI-TRAIL-R ANTIBODIES

(75) Inventors: Eiji Mori, Gunma (JP); Shiro Kataoka, Gunma (JP)

(73) Assignee: Kirin Beer Kabushiki Kaisha, Tokyo (JP)

(*) Notice: Subject to any disclaimer, the term of this patent is extended or adjusted under 35 U.S.C. 154(b) by 223 days.

(21) Appl. No.: 10/478,056

(22) PCT Filed: May 17, 2002

(86) PCT No.: PCT/JP02/04816

§ 371 (c)(1),
(2), (4) Date: Jun. 7, 2004

(87) PCT Pub. No.: WO02/094880

PCT Pub. Date: Nov. 28, 2002

(65) Prior Publication Data

US 2004/0214235 A1    Oct. 28, 2004

(30) Foreign Application Priority Data

| May 18, 2001 | (JP) | ............................ 2001-150213 |
| Aug. 9, 2001 | (JP) | ............................ 2001-243040 |
| Oct. 11, 2001 | (JP) | ............................ 2001-314489 |

(51) Int. Cl.
*A61K 39/395* (2006.01)
*C07K 16/30* (2006.01)

(52) U.S. Cl. .............................. 530/388.22; 530/387.3; 530/387.7; 530/388.1; 530/388.8; 424/143.1; 424/155.1

(58) Field of Classification Search ........... 530/388.22; 424/143.1
See application file for complete search history.

(56) References Cited

U.S. PATENT DOCUMENTS

| 6,072,047 A * | 6/2000 | Rauch et al. |
| 6,342,369 B1 * | 1/2002 | Ashkenazi |
| 6,461,823 B1 * | 10/2002 | Ni et al. |
| 6,872,568 B1 * | 3/2005 | Ni et al. |
| 2002/0155109 A1 * | 10/2002 | Lynch |
| 2004/0180049 A1 * | 9/2004 | Ashkenazi et al. |

FOREIGN PATENT DOCUMENTS

| JP | 10-327878 | 12/1998 |
| WO | WO 98/35986 | 8/1998 |
| WO | WO 98/41629 | 9/1998 |
| WO | WO 98/46643 | 10/1998 |
| WO | WO 98/51793 | 11/1998 |
| WO | WO 99/37684 | 7/1999 |

(Continued)

OTHER PUBLICATIONS

Silberstein et al., Relationship of variable region genes expressed by a human B cell lyphoma secreting pathologic anti-PR2 erythrocyte autoantibodies, J. Exp. Med., 169:1631-1643, May 1989.*

(Continued)

*Primary Examiner*—Lorraine Spector
*Assistant Examiner*—Claire M. Kaufman
(74) *Attorney, Agent, or Firm*—Foley & Lardner LLP

(57) ABSTRACT

Anti-TRAIL-R1 and R2 antibodies or functional fragments thereof, having at least one property selected from the following (a) to (c) of:
(a) having activity to induce apoptosis in carcinoma cells expressing TRAIL-R1 and/or TRAIL-R2;
(b) not having effect on normal human cells expressing TRAIL-R1 and/or TRAIL-R2; and
(c) not inducing human hepatocyte toxicity.

14 Claims, 13 Drawing Sheets

FOREIGN PATENT DOCUMENTS

| | | |
|---|---|---|
| WO | WO 96/64461 | 12/1999 |
| WO | WO 00/66156 | 11/2000 |
| WO | WO 99/37684 | 12/2000 |
| WO | WO 01/19861 A2 | 3/2001 |
| WO | WO 01/83560 | 11/2001 |
| WO | WO 02/079377 | 10/2002 |
| WO | WO 02/085946 | 10/2002 |
| WO | WO 03/038043 A2 | 5/2003 |
| WO | WO 03/042367 A2 | 5/2003 |

OTHER PUBLICATIONS

Kazuma Tomizuka et al., "Double trans-chromosomic mice: Maintenance on two individual human chromosome fragments containing Ig heavy and γ loci and expression of fully human antibodies", PNAS, vol. 97, No. 2, Jan. 18, 2000, pp. 722-727.

Anan Chuntharapai et al., "Isotype-Dependent Inhibition of Tumor Growth in Vivo by Monoclonal Antibodies to Death Receptor 4", The Journal of Immunology, vol. 166, pp. 4891-4898.

Kimihisa Ichikawa et al., "Tumoricidal Activity of a Novel antihuman DR5 Monoclonal Antibody without Helptocyte Cytotoxicity", Nature Medicine, vol. 7, No. 8, Aug. 2001, pp. 954-960.

Thomas S. Griffith et al., "Functional Analysis of TRAIL Receptors Using Monoclonal Antibodies", The Journal of Immunology, 1999, vol. 162: 2597-2605.

* cited by examiner

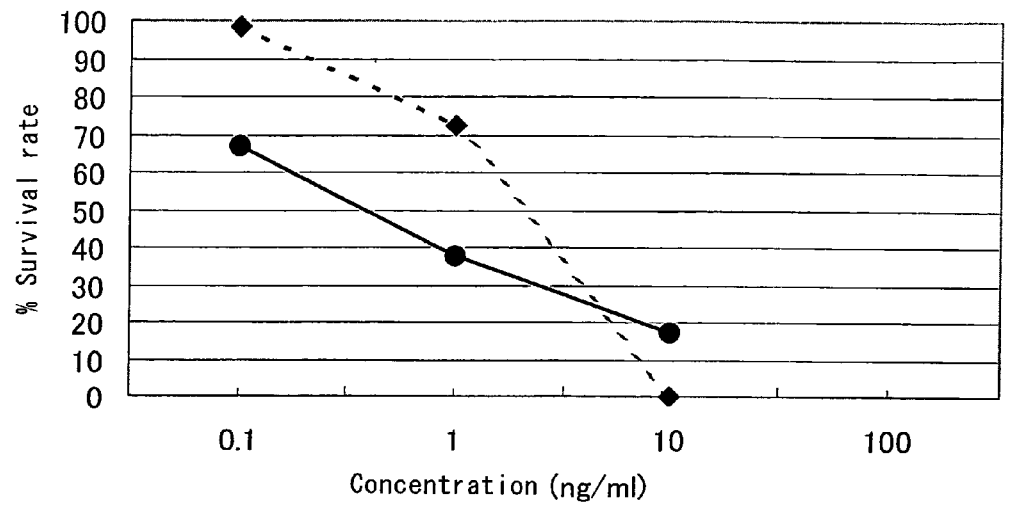
Fig. 5a Human recombinant TRAIL
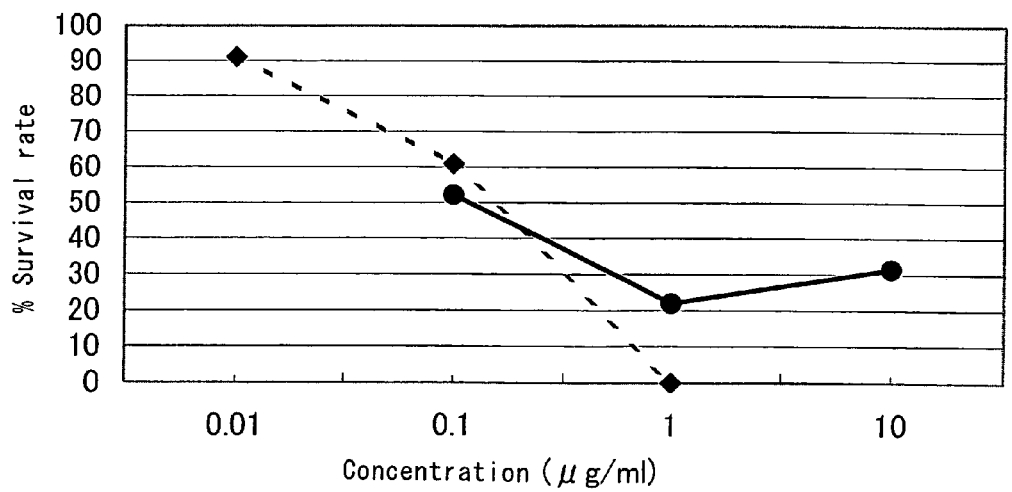
Fig. 5b H-48-2

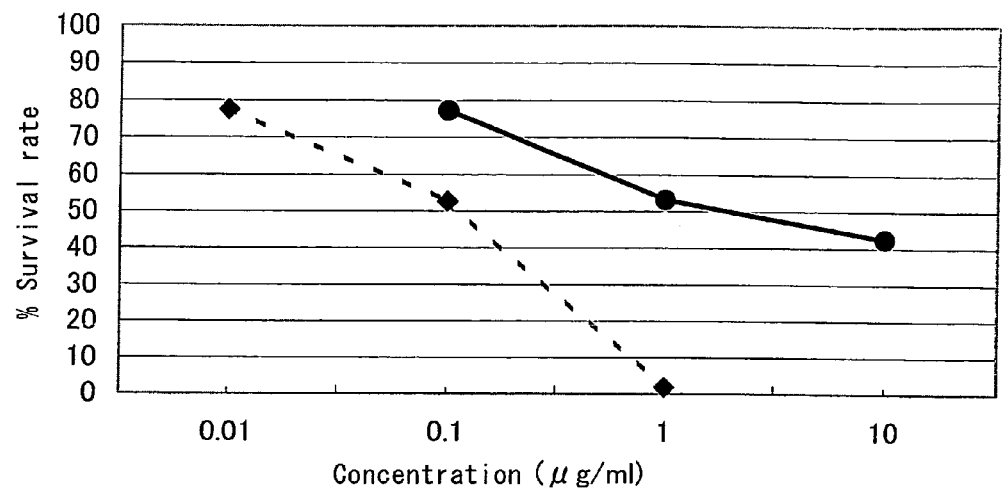
Fig. 5c E-11-13
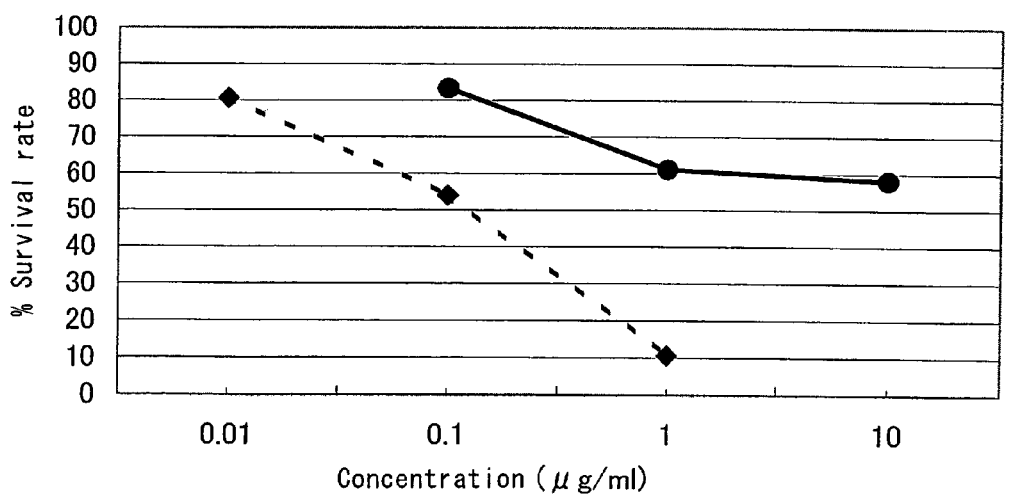
Fig. 5d L-30-10

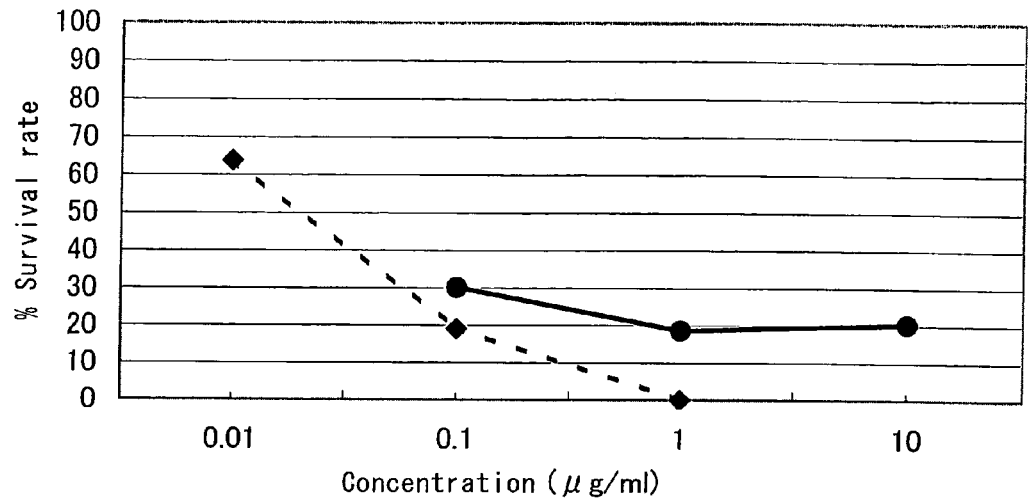
Fig. 5e F-4-8
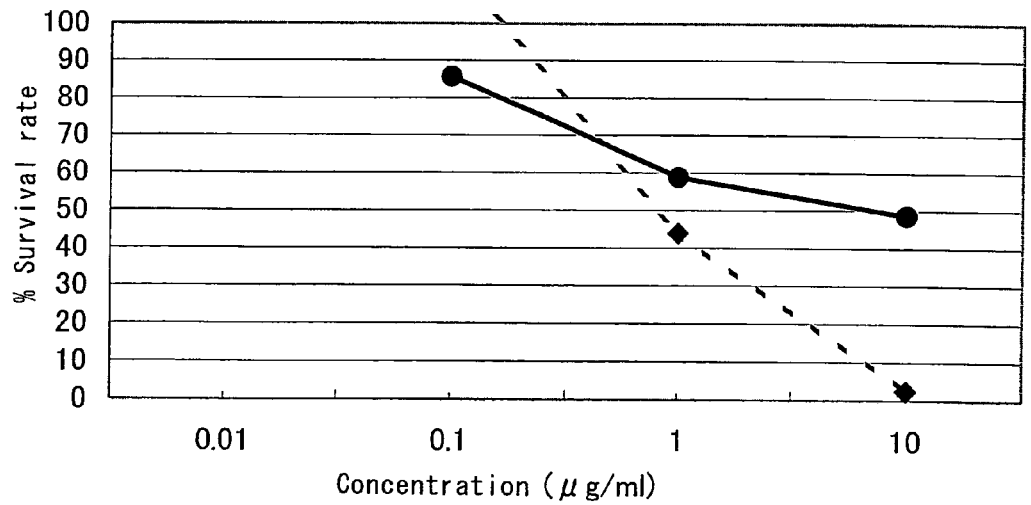
Fig. 5f W-40-5

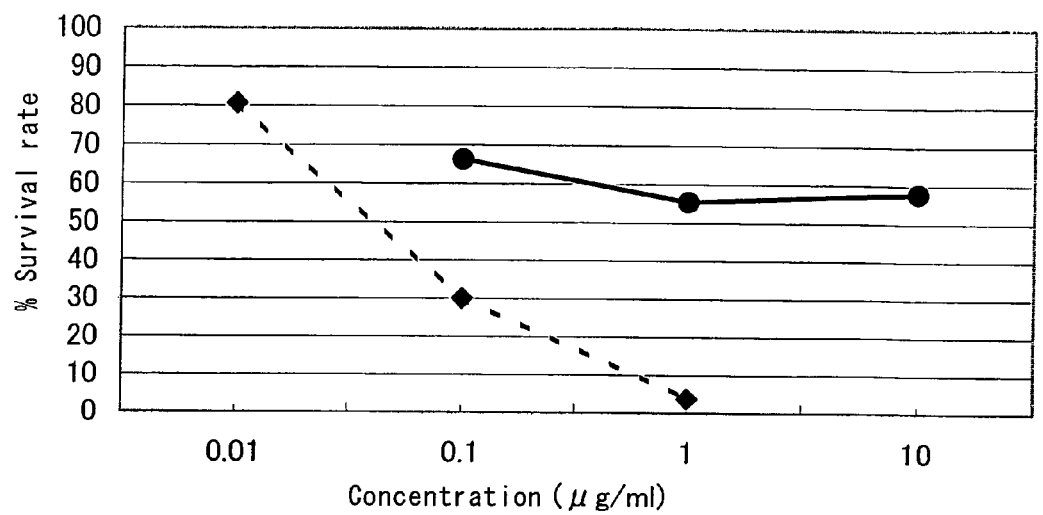
Fig. 5i KMTR1
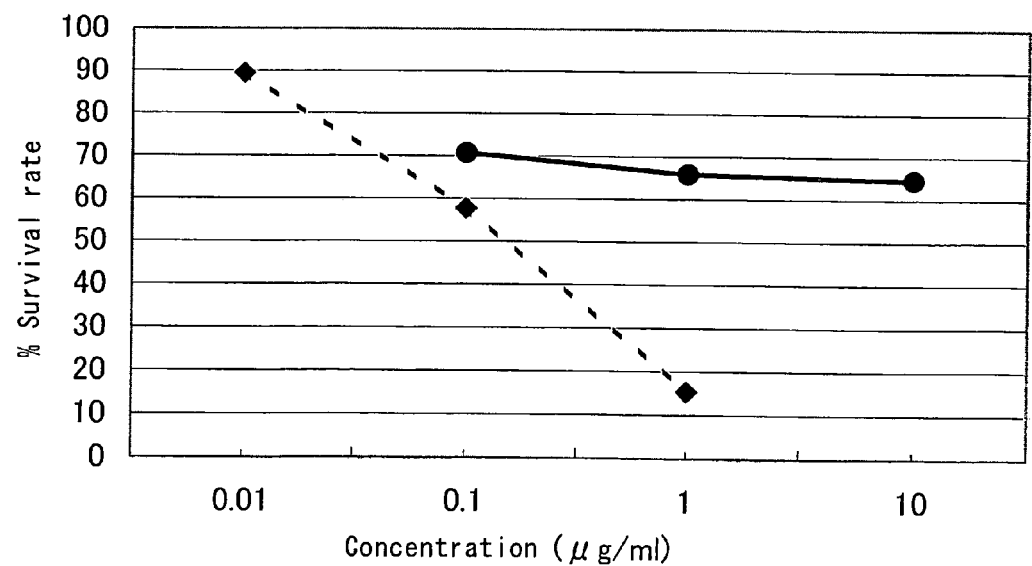
Fig. 5j D1M

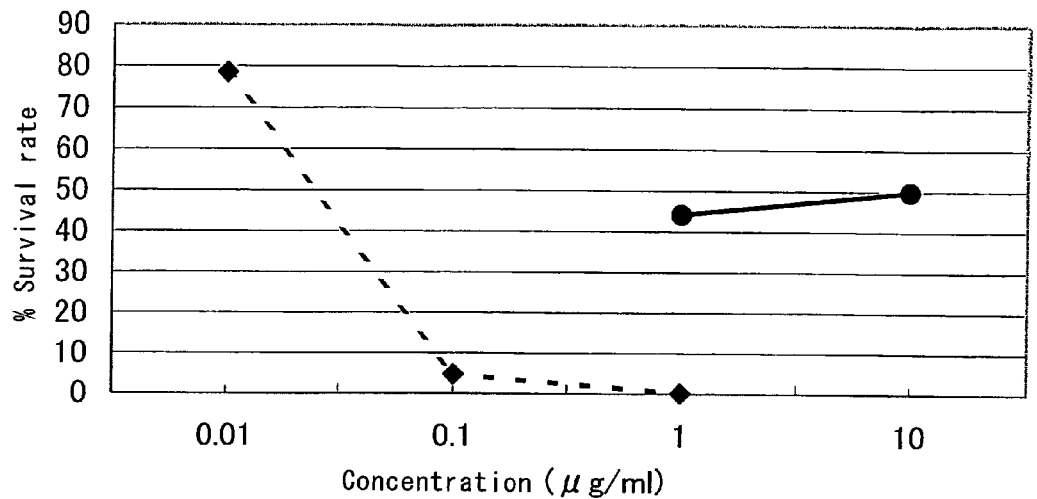
Fig. 5k 0304 (alone)
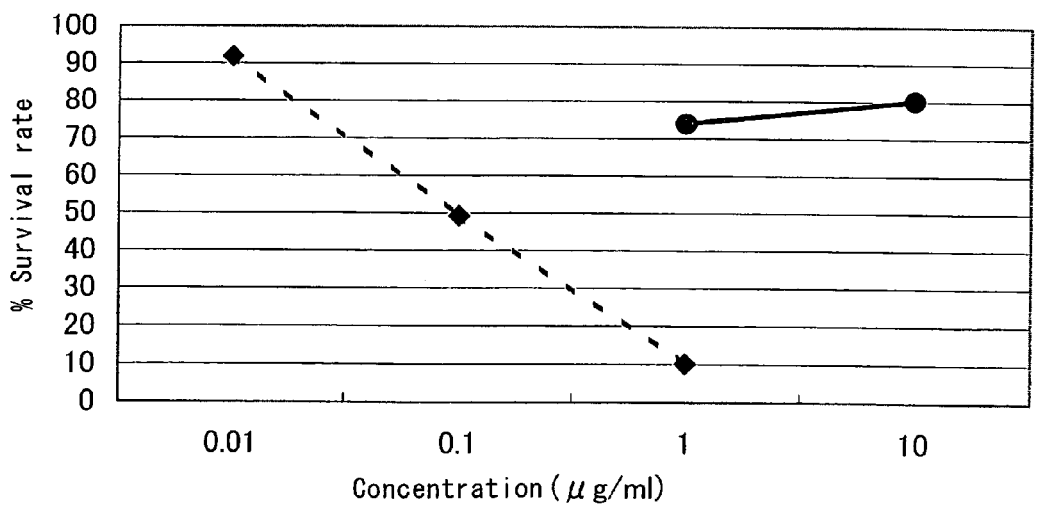
Fig. 5l KMTR1 (alone)

ANTI-TRAIL-R ANTIBODIES

FIELD OF THE INVENTION

The present invention relates to an anti-TRAIL receptor (TRAIL-R) antibody recognizing a TRAIL receptor 1 (TRAIL-R1) or a TRAIL receptor 2 (TRAIL-R2), which are cell membrane molecules involved in apoptosis.

Furthermore, the present invention relates to a prophylactic or therapeutic agent, which contains anti-TRAIL-R antibody as an active ingredient and is used against diseases caused by cells expressing TRAIL-R, and in particular relates to a therapeutic agent used against malignant tumors.

BACKGROUND OF THE INVENTION

In the living body, physiological cell death caused by normal cell alternation is referred to as apoptosis, and is distinguished from necrosis, which is pathological cell death [see Kerr, et al. (1972) Br. J. Cancer 26, 239]. Apoptosis is the phenomenon generally observed in the process of, for example, embryogenesis and the selection of lymphocytes (T cells and B cells) [see Itoh, S., et al. (1991) Cell 66, 233–243]. It is thought that when cells which should originally be eliminated by apoptosis are not removed, this may cause cancer, lupus, herpes virus infection, and other problems. Moreover, when cells that originally should survive are eliminated by apoptosis, this can cause diseases and pathological conditions such as AIDS, Alzheimer disease, Parkinson disease, amyotrophic lateral sclerosis, multiple sclerosis, retinitis pigmentosa, aplastic anemia, myocardial infarction, cerebral apoplexy or toxic substances-induced hepatopathy [see Kataoka, S., et al. (1996) The Oncologist 1, 399–401].

During apoptosis, characteristic phenomena such as curved cell surfaces, condensation of nuclear chromatin, fragmentation of chromosomal DNA, and loss of mitochondrial function are observed. Various intrinsic and extrinsic signals are thought to cause these cellular changes. As intrinsic signals, it has been reported that oncogenes such as myc and bcl-2 and tumor suppressor genes such as p53 are involved in apoptosis induction [see KATAOKA et al., (1993) JIKKEN IGAKU 11, 17, 2324–2328]. As extrinsic signals, it is known that chemotherapy drugs, radiation or the like induces apoptosis [see KATAOKA et al., (1994) SAISHIN IGAKU 49, 6, 1152–1157].

As molecules involved in such apoptosis, molecules belonging to tumor necrosis factor family (TNF family) such as tumor necrosis factor-α (TNF-α), tumor necrosis factor-β (TNF-β) and Fas ligand have been identified. TNF-α and TNF-β have been reported to induce apoptosis in carcinoma cells [see Schmid et al., (1986) Proc. Natl. Acad. Sci. 83, 1881; see Dealtry et al., (1987) Eur. J. Immunol. 17, 689]. Since mice having mutant Fas or Fas ligands develop the conditions of autoimmune disease, it has been strongly suggested that the Fas ligands have a function of eliminating self-reactive lymphocytes by apoptosis in the periphery [see Krammer, et al., (1994) Curr. Op. Immunol. 6, 279–289; see Nagata, et al., (1995) Science 267, 1449–1456]. It has been reported that agonistic mouse monoclonal antibodies that bind specifically to Fas exert apoptosis-inducing activity against carcinoma cells to the same level as that exerted by TNF-α [Yonehara, et al., (1989) J. Exp. Med. 169, 1747–1756].

These TNF family molecules transmit signals into cells by binding to specific receptors on the cell surfaces. Plural receptors for TNF family molecules are known, and they are referred to as TNF receptor family molecules.

TNF receptor family molecules are defined by the presence of cysteine-rich repetition of an extracellular domain. Among them, Fas and TNFR1, which are receptors of a Fas ligand and a TNF-α, contain within the cells a region referred to as a "death domain" sharing homology with reaper, a *Drosophila* suicide gene [see Golstein, P., et al. (1995) Cell 81, 185–186; see White, K., et al. (1994) Science 264, 677–683] and such death domain is essential for signal transduction for apoptosis. Activation of Fas promotes the association of an adapter molecule FADD/MORT1 containing the death domain, and induces the activation of caspase-8 bound to FADD/MORT1. The activated caspase-8 activates downstream caspase molecules in sequence, thereby finally leading the cells to apoptosis [see Nagata, S., (1997) Cell 88, 355–365].

Recently, a novel TNF family molecule that induces apoptosis has been found. Wiley et al., [see Immunity (1995) 3, 673–682] named the molecule "TNF-related apoptosis-inducing ligand" or briefly "TRAIL." This molecule is also referred to as "Apo-2 ligand" or "Apo-2L" [see Pitt, R. M., et al. (1996) J. Biol. Chem. 271, 12687–12690]. For convenience, this molecule is referred to as TRAIL in this specification.

Unlike the Fas ligand, TRAIL is detected at a significant level in many human tissues (e.g., spleen, lungs, prostate, thymus, ovary, small intestine, large intestine, peripheral blood lymphocyte, placenta and kidney). TRAIL is constitutively transcribed in some cell lines. TRAIL has also been shown to rapidly activate apoptosis at a significantly faster pace than that induced by TNF, within a time frame resembling death signal transduction by Fas [see Marsters, S. A., et al., (1996) Curr. Biol. 6, 750–752].

Now 5 proteins have already been identified as TRAIL receptors. Two receptors, TRAIL-R1 (also referred to as DR4) and TRAIL-R2 (also referred to as DR5), have both been reported to have death domains within the intracellular regions. The transcript of TRAIL-R1 is recognized in many human tissues including the spleen, peripheral blood leukocytes, small intestine and the thymus. The transcript of TRAIL-R2 has been detected in many tissues including the spleen, peripheral blood lymphocytes and the ovary [see Pan, G., et al. (1997) Science 276, 111–113; see Pan, G., et al. (1997) Science 277, 815–818; see Walczak, H., et al. (1997) EMBO J 16 (17) 5386–5397].

The presence of the two forms of TRAIL-R2 resulting from alternative splicing and the high expression amount of TRAIL-R2 comprising 440 amino acids in carcinoma cells has been reported [see Screaton, G. R., et al., (1997) Curr Biol 7 (9), 693–696; see Arai, T., et al., (1998) Cancer Letters 133, 197–204].

Recombinant human TRAIL is a recombinant protein comprising the extracellular region of TRAIL, and has been reported to induce apoptosis in many types of carcinoma cells [see Griffith, T. S., et al. (1998) Curr. Opin. Immunol., 10, 559–563].

Furthermore, the recombinant human TRAIL has exerted an effect on a tumor-bearing mouse model using human colon carcinoma cells and breast carcinoma cells [see Walczak, H., et al. (1999) Nature Medicine 5, 2, 157–163]. Unlike TNF-α or FAS ligands also belonging to the TNF receptor family and having apoptosis-inducing activity, TRAIL did not provide damage to the normal tissues of mice or cynomolgus monkeys [see Ashkenazi, A., et al. (1999) J. Clin. Invest. 104, 155–162].

Based on these reports, it is thought that TRAIL selectively induces death in tumor cells. However, such selectivity has not yet been supported theoretically since TRAIL receptors are also expressed in normal cells. Moreover, the recombinant human TRAIL has recently been reported to induce apoptosis in normal human hepatocytes [see Jo, M., et al. (2000) Nature Medicine 6, No. 5, 564–567] and reported to induce apoptosis also in human brain cells [see Nitsch, R., et al. (2000) The Lancet 356, 827–828]. Because agonistic anti-Fas antibodies, which induce apoptosis in hepatocytes, induce fulminant hepatitis in a very short time and thus cause death in mice and chimpanzees, cell death induction by TRAIL on hepatocytes has attracted attention as a particularly significant issue. The safety of using TRAIL as a pharmaceutical product for humans has been questioned [see Nagata, S., (2000) Nature Medicine 6, 5, 502–503].

It has also been reported that the presence or absence of the cell-death-inducing activity of TRAIL on hepatocytes depends on the type of recombinant TRAIL protein [see Lawrence, D., et al. (2001) Nature Medicine 7, 4, 383–385]. However, the safety of the recombinant TRAIL protein is still being studied.

Recently, anti-Fas antibodies that do not induce hepatopathy when administered to mice have been reported for the first time [see Ichikawa, K., et al. (2000) International Immunology 12, No. 4, 555–562]. There have been no known recombinant Fas ligands confirmed not to induce hepatopathy. This suggests that antibodies having activity that may be unavailable from ligands can be obtained. However, the theoretical background of the reason that the antibodies show no hepatotoxicity in spite of inducing apoptosis in T cells has not been revealed. For example, in the case of a different antigen such as TRAIL, it has not been demonstrated whether or not agonistic antibodies having no toxicity can be obtained.

TRAIL binds to TRAIL-R1, TRAIL-R2, or both, and induces apoptosis. However, via which receptor the signals to induce apoptosis in hepatocytes are introduced by TRAIL has not been shown. Furthermore, no research has been done based on the idea of whether hepatotoxicity can be avoided by adding TRAIL-R1/R2 selectivity to agonistic antibodies.

An effective therapeutic means against malignant tumors involves removing carcinoma cells and protecting normal tissues or cells. A drug whose action mechanism is apoptosis induction by the recombinant human TRAIL may cause damages to normal tissues, particularly the liver and the brain, even if it is able to remove carcinoma cells.

Currently, monoclonal antibodies such as a chimeric antibody targeting CD20, which is a receptor present on the cell membrane, and a humanized antibody targeting Her2/neu are used against malignant tumors as target diseases, and their therapeutic effects have been recognized. Since antibodies have characteristics including a long half-life in blood and high specificity to antigens, they are particularly useful as anti-tumor agents. For example, in the case of antibodies targeting tumor-specific antigens, the administered antibodies are assumed to accumulate in tumors. Thus, attack against carcinoma cells by the immune system can be expected by complement-dependent cytotoxicity and antibody-dependent cell-mediated cytotoxicity. In addition, the binding of a drug such as a radionuclide, a cytotoxic substance or the like to the antibodies enables the efficient delivery of the drug bound to the antibody to tumor sites. At the same time, reduced side effects can be expected due to decreased amounts of the drug having reached other non-specific tissues. When tumor-specific antigens have activity to induce cell death, antibodies having agonistic activity are administered, and when tumor-specific antigens are involved in cell proliferation and survival, antibodies having neutralization activity are administered. And then, the accumulation of tumor-specific antibodies and suppression of tumor growth or regression of tumors due to the activity of the antibodies can be expected.

It is thought to be appropriate to apply antibodies as anti-tumor agents because of the characteristics described above. In addition, if antibodies are those against TRAIL receptors, antibodies that may be obtained can avoid causing damage to the liver, which is unable to avoid with the recombinant human TRAIL, and have equivalent apoptosis-inducing activity against carcinoma cells.

SUMMARY OF THE INVENTION

A first purpose of the present invention is to provide a novel antibody or a molecule analogous thereto, which is capable of binding to human TRAIL-R1 and/or human TRAIL-R2 and induces apoptosis specifically in carcinoma cells, without inducing damage to normal human hepatocytes to which a recombinant human TRAIL protein can cause damages. A second purpose of the present invention is to provide a prophylactic or therapeutic agent comprising the above antibody or a molecule analogous thereto as an active ingredient against various malignant tumors including solid tumors that are currently difficult to treat.

As a result of intensive studies on the production of antibodies against human TRAIL-R1 and TRAIL-R2, we have succeeded in obtaining monoclonal antibodies from the culture supernatant by immunizing transgenic mice capable of producing human antibodies by genetic engineering techniques with human TRAIL-R1 or TRAIL-R2, generating hybridomas producing novel monoclonal antibodies that bind to TRAIL-R1 and/or TRAIL-R2 using the method of Kohler and Milstein et al. [see (1975) Nature 256, 495], which is generally used in monoclonal antibody production.

Furthermore, we have completed the present invention by finding that the novel monoclonal antibodies induce apoptosis specifically in carcinoma cells by binding to TRAIL-R1 and/or R2 present on the surfaces of carcinoma cells.

The present invention is as follows.

(1) An antibody or a functional fragment thereof, binding to TRAIL-R1 and/or TRAIL-R2.

The above antibody or the functional fragment thereof has at least one property selected from the following (a) to (c) of:

(a) having activity to induce apoptosis in carcinoma cells expressing TRAIL-R1 and/or TRAIL-R2;

(b) not having effect on normal human cells expressing TRAIL-R1 and/or TRAIL-R2; and (c) not inducing human hepatocyte toxicity.

In the present invention, an antibody or a functional fragment thereof having all the above properties (a) to (c) is preferred. Furthermore, the antibody or the functional fragment thereof of the present invention also includes an antibody or a functional fragment thereof that has at least one property of the above (a) to (c), and (1) binds to TRAIL-R2, but does not bind to TRAIL-R1, or (2) binds to both TRAIL-R2 and TRAIL-R1.

(2) The above antibody is a monoclonal antibody produced by a mouse—mouse hybridoma, such as E-11-13, H-48-2, L-30-10, N-18-12, W-40-5, X-14-4, X-51-12, F-4-8, G-3-10, 0304 or KMTR1, and is preferably a human antibody. The type of the monoclonal antibody produced by E-11-13, H-48-2, L-30-10, N-18-12, W-40-5, X-14-4, X-51-12, F-4-8, 0304 or KMTR1 is the immunoglobulin G(IgG), and the type of the monoclonal antibody produced by G-3-10 is the immunoglobulin M(IgM). H-48-2, E-11-13, F-4-8, L-30-10, 0304 and KMTR1 of the above hybridomas are respectively deposited internationally, and the desposition information is as follows.

| Name | Accession No. | Deposition date | Deposited with: |
|---|---|---|---|
| H-48-2 | FERM BP-7599 | May 18, 2001 | International Patent |
| E-11-13 | FERM BP-7698 | Aug. 8, 2001 | Organism Depositary, |
|  | FERM BP-7770 | Oct. 11, 2001 | National Institute of |
| F-4-8 | FERM BP-7699 | Aug. 8, 2001 | Advanced Industrial |
|  | FERM BP-7768 | Oct. 11, 2001 | Science and Technology |
| L-30-10 | FERM BP-7700 | Aug. 8, 2001 | (Central 6, 1-1-1, |
|  | FERM BP-7769 | Oct. 11, 2001 | Higashi, Tsukuba, |
| 0304 | FERM BP-8037 | May 10, 2002 | Ibaraki, Japan) |
| KMTR1 | FERM BP-8038 | May 10, 2002 |  |

Examples of carcinoma cells include colon carcinoma cells, Colo205, glioma U251 cells and T cell lymphoma Jurkat cells. The carcinoma cells are appropriately selected from these cells.

(3) The antibody or the functional fragment thereof of the present invention has, under conditions where the number of cells is $7.5 \times 10^4$ and the reaction time is 24 hours, an LD50 value for human hepatocytes of 0.01 μg/ml or more, preferably 0.1 μg/ml or more, further preferably 2 to 10 μg/ml, still further preferably 10 to 100 μg/ml, or most preferably 10 μg/ml or more (e.g., 100 μg/ml or more). In the meantime, the antibody or the functional fragment thereof of the present invention has, under conditions where the number of cells is $2.5 \times 10^3$ and the reaction time is 48 hours, an LD50 value for carcinoma cells (e.g., Colo205 cells, U251 cells or Jurkat cells) of 100 μg/ml or less, preferably 10 μg/ml or less, more preferably 0.7 μg/ml or less, further preferably 0.02 to 0.11 μg/ml, or most preferably 0.02 μg/ml or less. Moreover, the antibody or the functional fragment thereof that is particularly preferred in the present invention has a combination of LD50 values, one of which is between 2 and 100 μg/ml for human heptocytes under conditions where the number of cells is $7.5 \times 10^4$ and the reaction time is 24 hours, and the other of which is between 0.02 and 0.11 μg/ml for carcinoma cells under conditions where the number of cells is $2.5 \times 10^3$ and the reaction time is 48 hours.

The above LD50 values of the antibody of the present invention for hepatocytes or carcinoma cells are obtained by measurement with a reaction volume of 110 to 120 μl per reaction system (per well).

(4) Furthermore, the antibody or the functional fragment thereof of the present invention has an LD50 value for human hepatocytes under conditions where the number of cells is $7.5 \times 10^4$ and the reaction time is 24 hours that is 2 times or more, preferably 10 times or more, more preferably 50 times or more (e.g., 50 times to 100 times), further preferably 100 times or more (e.g., 100 times to 250 times), still further preferably 250 times to 1000 times, or most preferably 1000 times or more greater than that for carcinoma cells under conditions where the number of cells is $2.5 \times 10^3$ and the reaction time is 48 hours.

(5) Furthermore, the antibody or the functional fragment thereof of the present invention can suppress the growth of tumors (e.g., those derived from Colo205 cells transplanted to nude mice) or regress tumors. In this case, a period during which tumor cell proliferation can be suppressed, or during which tumor regression can be achieved when the antibody or the functional fragment thereof of the present invention is administered, is at least 9 days, preferably at least 11 days or further preferably at least 13 days. Hereinafter, the period, in order of preference, is as follows: at least 30 days, at least 60 days, and most preferably at least 120 days. In addition, the dose of the antibody or the functional fragment thereof of the present invention that is administered to a tumor-bearing animal to be tested (e.g., a body weight of a tumor-bearing experimental animal is 20 g) is between 0.1 μg/body (5 μg/kg) and 100 μg/body (5 mg/kg). For example, the dose is 100 μg/body or 5 mg/kg, preferably 20 μg/body or 1 mg/kg, more preferably 4 μg/body or 200 μg/kg, or further preferably 1 μg/body or 50 μg/kg. A dose of 0.5 μg/body (25 μg/kg) may also be administered. The administration frequency is, for example, once to 3 times per week, or administration is performed on alternate days.

Moreover, the anti-tumor effect of the antibody (e.g., 0304 antibody or E-11-13 antibody) or the functional fragment thereof of the present invention in tumor-bearing mice is as follows.

(a) When administered at a concentration of 20 μg/mouse to a 4- to 6-week-old tumor-bearing mouse having a 100 mm$^3$ tumor, the antibody or the functional fragment thereof can induce an average of 14% or more tumor reduction by 4 days after the initial administration. In this case, an average of 14% or more tumor reduction can be maintained for at least 7 days.

(b) When administered at a concentration of 20 μg/mouse to a 4- to 6-week-old tumor-bearing mouse having a 100 mm$^3$ tumor, the antibody or the functional fragment thereof can induce an average of 65% or more tumor reduction by 4 days after the initial administration.

(c) When administered at a concentration of 20 μg/mouse to a 4- to 6-week-old tumor-bearing mouse having a 100 mm$^3$ tumor, the antibody or the functional fragment thereof can induce an average of 80% or more tumor reduction by 7 days after the initial administration. In this case, an average of 80% or more tumor reduction can be maintained for at least 4 days.

(d) When administered at a concentration of 25 μg/mouse to a 12-week-old tumor-bearing mouse having a 100 mm$^3$ tumors, the antibody or the functional fragment thereof can induce an average of 45% or more tumor reduction by 3 days after the initial administration.

(e) When administered at a concentration of 25 μg/mouse to a 12-week-old tumor-bearing mouse having a 100 mm$^3$ tumor, the antibody or the functional fragment thereof can induce an average of 65% or more tumor reduction by 5 days after the initial administration. In this case, an average of 65% or more tumor reduction can be maintained for at least 27 days.

(f) When administered at a concentration of 20 μg/mouse to a 4- to 6-week-old tumor-bearing mouse having a 300 mm$^3$ tumor, the antibody or the functional fragment thereof can induce an average of 39% or more tumor reduction by 4 days after the initial administration. In this case, an average of 39% or more tumor reduction can be maintained for at least 14 days.

Examples of the relevant tumor include at least one tumor selected from the group consisting of colon cancer, colorectal cancer, lung cancer, breast cancer, brain tumor, malignant melanoma, renal cell carcinoma, bladder cancer, leukemia, lymphomas, T cell lymphomas, multiple myeloma, gastric cancer, pancreas cancer, cervical cancer, endometrial carcinoma, ovarian cancer, esophageal cancer, liver cancer, head and neck squamous cell carcinoma, cutaneous cancer, urinary tract carcinoma, prostate cancer, choriocarcinoma, pharyngeal cancer, laryngeal cancer, thecomatosis, androblastoma, endometrium hyperplasy, endometriosis, embryoma, fibrosarcoma, Kaposi's sarcoma, hemangioma, cavernous hemangioma, angioblastoma, retinoblastoma, astrocytoma, neurofibroma, oligodendroglioma, medulloblastoma, ganglioneuroblastoma, glioma, rhabdomyosarcoma, hamartoblastoma, osteogenic sarcoma, leiomyosarcoma, thyroid sarcoma and Wilms tumor.

(6) An antibody or a functional fragment thereof having amino acid sequences of the mature portions of a heavy chain variable region and a light chain variable region of the antibody produced by a hybridoma E-11-13, which are respectively represented by SEQ ID NOS: 17 and 19; a heavy chain variable region and a light chain variable region of the antibody produced by a hybridoma L-30-10, which are respectively represented by SEQ ID NOS: 21 and 23; a heavy chain variable region and a light chain variable region of the antibody produced by a hybridoma H-48-2, which are respectively represented by SEQ ID NOS: 25 and 27; a heavy chain variable region and a light chain variable region of the antibody produced by a hybridoma 0304, which are respectively represented by SEQ ID NOS: 29 and 31; or a heavy chain variable region and a light chain variable region of the antibody produced by a hybridoma KMTR1, which are respectively represented by SEQ ID NOS: 33 and 35.

The above antibody or the functional fragment thereof has amino acid sequences of the mature portions of a heavy chain variable region and a light chain variable region that are encoded by nucleic acid sequences isolated from a hybridoma E-11-13, which are respectively represented by SEQ ID NOS: 16 and 18; a heavy chain variable region and a light chain variable region that are encoded by nucleic acid sequences isolated from a hybridoma L-30-10, which are respectively represented by SEQ ID NOS: 20 and 22; a heavy chain variable region and a light chain variable region that are encoded by nucleic acid sequences isolated from a hybridoma H-48-2, which are respectively represented by SEQ ID NOS: 24 and 26; a heavy chain variable region and a light chain variable region that are encoded by nucleic acid sequences isolated from a hybridoma 0304, which are respectively represented by SEQ ID NOS: 28 and 30; or a heavy chain variable region and a light chain variable region that are encoded by nucleic acid sequences isolated from a hybridoma KMTR1, which are respectively represented by SEQ ID NOS: 32 and 34.

(7) A hybridoma producing monoclonal antibodies that bind to TRAIL-R2, which is selected from the group consisting of E-11-13, H-48-2, L-30-10, N-18-12, W-40-5, X-14-4, X-51-12, F-4-8, G-3-10, 0304 and KMTR1.

(8) A method for producing anti-TRAIL-R2 monoclonal antibodies, comprising culturing the above hybridoma and collecting the antibodies binding to TRAIL-R2 from the obtained culture product.

(9) A method for producing anti-TRAIL-R2 monoclonal antibodies, comprising isolating a gene encoding a monoclonal antibody from the above hybridoma, constructing an expression vector having the gene, introducing the expression vector into a host to express the above monoclonal antibody, and collecting anti-TRAIL-R2 monoclonal antibodies from the host, or the culture supernatant or the secretion of the obtained host.

Examples of a host include any host selected from the group consisting of Escherichia coli, yeast cells, insect cells, mammalian cells and plant cells, and mammals.

(10) A prophylactic or therapeutic agent against tumors, comprising as an active ingredient the above antibody or the functional fragment thereof.

Examples of the tumor include at least one tumor selected from the group consisting of colon cancer, colorectal cancer, lung cancer, breast cancer, brain tumor, malignant melanoma, renal cell carcinoma, bladder cancer, leukemia, lymphomas, T cell lymphomas, multiple myeloma, gastric cancer, pancreas cancer, cervical cancer, endometrial carcinoma, ovarian cancer, esophageal cancer, liver cancer, head and neck squamous cell carcinoma, cutaneous cancer, urinary tract carcinoma, prostate cancer, choriocarcinoma, pharyngeal cancer, laryngeal cancer, thecomatosis, androblastoma, endometrium hyperplasy, endometriosis, embryoma, fibrosarcoma, Kaposi's sarcoma, hemangioma, cavernous hemangioma, angioblastoma, retinoblastoma, astrocytoma, neurofibroma, oligodendroglioma, medulloblastoma, ganglioneuroblastoma, glioma, rhabdomyosarcoma, hamartoblastoma, osteogenic sarcoma, leiomyosarcoma, thyroid sarcoma and Wilms tumor.

The present invention is explained in detail as follows. This specification includes part or all of the contents as disclosed in the specification and/or drawings of Japanese Patent Application No. 2001-150213 (filed on May 18, 2001), Japanese Patent Application No. 2001-243040 (filed on Aug. 9, 2001), and Japanese Patent Application No. 2001-314489 (filed on Oct. 11, 2001) which are priority documents of the present application.

The anti-TRAIL-R1 and R2 monoclonal antibodies have been reported to have activity to induce apoptosis in carcinoma cells [see Griffith, T. S., et al. (1999) J. Immunol. 162, 2597–2605; see Chuntharapai, A., et al. (2001) J. Immunol. 166, 4891–4898]. However, these antibodies are derived from mice.

In addition, the cytotoxicity against normal human hepatocytes, which is also questioned in a recombinant human TRAIL protein, is a concern.

Surprisingly, the novel human anti-TRAIL-R2 monoclonal antibody of the present invention has been revealed to have no side effect of inducing cytotoxicity against not only cells derived from a normal human tissue, but also normal hepatocytes for which cytotoxicity by the recombinant human TRAIL protein is a concern. We have obtained a novel anti-TRAIL-R2 monoclonal antibody. That is, we have completed the present invention by succeeding for the first time in the world in producing a novel monoclonal antibody provided with possible advantages of improved safety and therapeutic effects. The monoclonal antibody is preferably a human antibody. Its antigenicity, which is always a problem in the case of a mouse-derived antibody, has already been avoided.

Any antibody type of immunoglobulin G(IgG), A(IgA), E(IgE) or M(IgM) can be appropriately used as the antibody. Normally, IgG is more preferred.

The present invention is explained in detail by making clear the meanings of the words and phrases used in the present invention as follows.

1. TRAIL and the Antibody

The antibody of the present invention is an antibody against the receptor of a tumor necrosis factor (TNF)-related apoptosis-inducing ligand (TRAIL) (TRAIL-R). The antibodies of the present invention are (1) an antibody reacting with TRAIL-R1, (2) an antibody reacting with TRAIL-R2, and (3) an antibody reacting with both TRAIL-R1 and TRAIL-R2. In the present invention, the antibody (1) may be referred to as "the anti-TRAIL-R1 antibody," and the antibodies (2) and (3) may be referred to as "the anti-TRAIL-R2 antibodies." In addition, when both TRAIL receptors, TRAIL-R1 and TRAIL-R2, are conveniently explained together in this specification, they may be referred to as "TRAIL-R1 and R2." Therefore, for example, the description of "TRAIL-R1 and R2 expression vectors" (see Example 1, below) is meant to explain two expression vectors, the expression vector of TRAIL-R1 and the expression vector of TRAIL-R2.

The "antibody" in the present invention is an antibody or a part thereof having reactivity to the human TRAIL-R1 and R2 or a part thereof as defined above, and includes functional fragments of these antibodies. The "functional fragment" means a part (partial fragment) of the antibody retaining one or more actions of the antibody on an antigen. Specific examples of functional fragments include F(ab')$_2$, Fab', Fab, Fv, disulfide-bound Fv, single chain Fv(scFv) and the polymers thereof (D. J. King., Applications and Engineering of Monoclonal Antibodies., 1998 T. J. International Ltd).

The "human antibody" in the present invention means an antibody which is the expression product of a human-derived antibody gene.

Examples of the antibody of the present invention include various antibodies having a property of inducing apoptosis in carcinoma cells expressing the human TRAIL-R1 and R2 as later described in Example 7.

The antibody of the present invention encompasses a monoclonal antibody comprising heavy chains and/or light chains having amino acid sequences with deletion, substitution or addition of one or a plurality of amino acids in each amino acid sequence of the heavy chain and/or light chain of the antibody. The above-described partial amino acid alteration (deletion, substitution, insertion or addition) can be introduced into the amino acid sequence of the antibody of the present invention by, for example, a method which involves partial alteration of the nucleotide sequence encoding the amino acid sequence. The partial alteration can be introduced into the nucleotide sequence by a standard method using known site-specific mutagenesis (Proc Natl Acad Sci USA., 1984 Vol 81: 5662). Here, the antibody is an immunoglobulin wherein all the regions, including a heavy chain variable region and a heavy chain constant region, and a light chain variable region and a light chain constant region composing the immunoglobulin, are derived from a gene encoding the immunoglobulin.

The antibody of the present invention also encompasses antibodies having any immunoglobulin classes and isotypes.

The anti-TRAIL-R1 and R2 antibodies of the present invention can be produced by the following production method. Specifically, for example, the above-defined human TRAIL-R1 and R2 or a part thereof is bound to an appropriate substance (e.g., bovine serum albumin) for enhancing the antigenicity of an antigen, and then non-human mammals including human antibody-producing transgenic mice and the like are immunized with the bound product, together with an immunopotentiator (e.g., Freund's complete or incomplete adjuvant) if necessary. Alternatively, immunization can also be performed by introducing a gene encoding the human TRAIL-R1 or human TRAIL-R2, and then administering animal cells excessively expressing TRAIL-R1 or TRAIL-R2 on the cell surfaces. Monoclonal antibodies can be obtained by culturing hybridomas that are obtained by fusing antibody-producing cells obtained from immunized animals with myeloma cells incapable of producing autoantibodies, and then selecting clones that produce monoclonal antibodies showing specific affinity for the antigens used for immunization.

The antibody of the present invention encompasses an antibody converted to have a different subclass by alteration using genetic engineering techniques known to a person skilled in the art. For example, the subclass switching of the antibody of the present invention to IgG2 or IgG4 enables antibodies with a low binding activity to Fc receptors to be obtained. Also, the subclass switching of the antibody of the present invention to IgG1 or IgG3 enables antibodies with a high binding activity to Fc receptors to be obtained. Moreover, the binding activity to a Fc receptor can also be changed by artificially altering the amino acid sequence of the constant region of the antibody of the present invention, or by binding with a constant region sequence having such an altered sequence. Furthermore, the therapeutic effect against diseases such as cancer can be further enhanced by binding to the antibody of the present invention a radionuclide such as iodine, yttrium, indium or technitium, (J. W. Goding, Monoclonal Antibodies: principles and practice., 1993 Academic Press), bacterial toxin such as pyocyanic toxin, diphteria toxin or lysin, chemotherapeutics such as methotrexate, mitomycin or calicheamicin (D. J. King, Applications and Engineering of Monoclonal Antibodies., 1998 T. J. International Ltd.; M. L. Grossbard., Monoclonal Antibody-Based Therapy of Cancer., 1998 Marcel Dekker Inc), or else a prodrug such as Maytansinoid (Chari et al., Cancer Res., 1992 Vol. 52: 127; Liu et al., Proc. Natl. Acad. Sci. USA, 1996 Vol. 93: 8681).

Moreover, we have found that the antibodies of the present invention having the property of binding to TRAIL-R2 but not the property of binding to TRAIL-R1 include antibodies that do not induce human hepatocyte toxicity. Therefore, the present invention also provides a method for producing anti-TRAIL-R2 antibodies having no hepatocyte toxicity, comprising a step of selecting antibodies that do not bind to TRAIL-R1 from the antibody population that binds to TRAIL-R2. However, the antibody of the present invention having no hepatocyte toxicity is not limited to an antibody having the property of binding to TRAIL-R2 but not the property of binding to TRAIL-R1.

The present invention encompasses the following operation steps in monoclonal antibody production. Specifically, the steps are, for example: (1) purification of biopolymers and/or the preparation of cells excessively expressing antigen proteins on the cell surfaces (these biopolymers and/or cells are used as immunogens); (2) immunization of animals by the injection of an antigen, blood collection, testing of the antibody titer, and determination of a time for excising the spleen and the like followed by preparation of antibody-producing cells; (3) preparation of myeloma cells (hereinafter referred to as "myeloma"); (4) cell fusion of the antibody-producing cells with myeloma, (5) selection of a hybridoma group producing a target antibody; (6) division into a single cell clone (cloning); (7) if necessary, culture of hybridomas for producing monoclonal antibodies in large quantities, or breeding of animals having the hybridomas transplanted therein; and (8) study of the physiological activities and the recognition specificity of the thus-produced monoclonal antibodies, or testing of the characteristics as a labeled reagent.

The production method of anti-TRAIL-R1 and R2 monoclonal antibodies is described in detail according to the above steps, but the production method of the antibody is not limited to this method. For example, antibody-producing cells and myeloma other than splenocytes can also be used.

(1) Purification of Antigen

As the antigen, a fusion protein of the extracellular regions of human TRAIL-R1 and R2 with the Fc region of a human IgG (hereinafter referred to as TRAIL-R1-hFc and TRAIL-R2-hFc) can be used. TRAIL-R1-hFc and TRAIL-R2-hFc can be obtained by integrating a DNA encoding a fusion protein of TRAIL-R1 or R2 with the Fc region of a human IgG into an expression vector for animal cells, introducing the expression vector into animal cells, and then purifying from the culture supernatant of the obtained transfectant strain. Alternatively, TRAIL-R1-hFc and TRAIL-R2-hFc commercially available from ALEXIS and the like can also be used. Furthermore, purified TRAIL-R1 and R2 from the cell membranes of a human cell line, can also be used as the antigen. Furthermore, the primary structures of TRAIL-R1 and R2 are known [see Pan, G., et al. (1997) Science 276, 111–113 and Science 277, 815–818; see Walczak, H., et al. (1997) EMBO J 16 (17) 5386–5397]. Thus, according to a method known by a person skilled in the art, peptides are chemically synthesized from the amino acid sequences of TRAIL-R1 and R2, and then can also be used as the antigen.

As the immunogen, Cells which are transfected with the expression vectors pEF-TRAIL-R1delta and pEF-TRAIL-R2delta, which contain a DNA encoding human TRAIL-R1 and R2 deleting the death domain and the amino acids on the C-terminal side from the death domain in the intracellular region (hereinafter referred to as "TRAIL-R1 and R2delta"), into L929 cells and excessively express TRAIL-R1 and R2delta on the cell surfaces are effective. pEF-TRAIL-R1delta and pEF-TRAIL-R2delta can be prepared by respectively integrating a DNA encoding a human TRAIL-R1delta protein and a DNA encoding a human TRAIL-R2delta protein into pEFneo, expression vectors for animal cells [see Ohashi. H., et al. (1994) Proc. Natl. Acad. Sci. 91, 158–162]. The DNAs encoding TRAIL-R1 and R2, vector, host and the like are not limited thereto.

Specifically, the transfectant strain obtained by transfecting L929 cells with pEF-TRAIL-R1 and R2delta is cultured. Using as indicators the neomycin resistance trait acquired by the cells having pEFneo vectors inserted therein and the confirmation of the expression of TRAIL-R1 and R2delta using goat anti-TRAIL-R1 and R2 polyclonal antibodies (DAKO), L929 cells excessively expressing human TRAIL-R1 and R2delta on the cell surfaces can be prepared.

(2) Preparation Step of Antibody-Producing Cell

The antigen obtained in (1), Freund's complete or incomplete adjuvant or an assistant such as potassium aluminum sulfate are mixed, and then experimental animals are immunized with the mixture as an immunogen. Transgenic mice capable of producing human-derived antibodies are most preferably used as experimental animals, and such mice are described in the publication of Tomizuka et al [Tomizuka. et al., Proc Natl Acad Sci USA., 2000 Vol 97: 722].

The method for administering immunogens upon mouse immunization may be any of subcutaneous injection, intraperitoneal injection, intravenous injection, intracutaneous injection, intramuscular injection or footpad injection. Subcutaneous injection, intraperitoneal injection, footpad injection or intravenous injection is preferred.

Immunization can be performed once, or repeatedly (multiple times) at appropriate intervals (intervals of preferably 3 days to 1 week or intervals of 2 weeks). Subsequently, the antibody titer against the antigen in the serum of the immunized animal is measured, and the animals showing sufficiently increased antibody titers are used as a source of antibody-producing cells, so that the effect of the following steps can be enhanced. Generally, antibody-producing cells derived from animals 3 to 5 days after the final immunization are preferably used for the following cell fusion step.

Examples of the method for measuring antibody titer that is used herein include various known techniques such as the radioimmunoassay (hereinafter referred to as "RIA method"), enzyme-linked immunosorbent assay (hereinafter, referred to as "ELISA method"), fluorescent antibody method and passive haemagglutination method. In view of, for example, detection sensitivity, promptness, correctness, and possibility of automation of the operation, the RIA method or the ELISA method is more preferred.

In the present invention, antibody titer can be measured by the following procedures according to, for example, the ELISA method. First, purified or partially purified recombinant human TRAIL-R1 and R2 are adsorbed on the surface of a solid phase such as a 96-well plate for ELISA. The solid phase surface, on which no antigen is adsorbed, is further coated with a protein, which is independent of the antigen, such as bovine serum albumin (hereinafter referred to as "BSA"). After the surface is washed, it is allowed to come into contact with a sample (e.g., mouse serum) that has been subjected to serial dilution as a primary antibody. Anti-TRAIL-R1 and R2 antibodies in the sample are bound to the above antigen. As a secondary antibody, enzyme-labeled antibodies against human antibodies are added and bound to the human antibodies. After washing, the substrate of the enzyme is added, and then changes and the like in absorbance due to color development resulting from substrate degradation are measured. By this method, antibody titer is calculated.

(3) Preparation Step of Myeloma

As myeloma, cells incapable of producing autoantibodies and derived from mammals such as mice, rats, guinea pigs, hamsters, rabbits or humans can be used. In general, established cell lines obtained from mice, for example, 8-azaguanine-resistant mouse (derived from BALB/c) myeloma strains P3X63Ag8U.1 (P3-U1) [Yelton, D. E. et al. Current Topics in Microbiology and Immunology, 81, 1–7 (1978)], P3/NSI/1-Ag4-1(NS-1) [Kohler, G. et al. European J. Immunology, 6, 511–519 (1976)], Sp2/O-Ag14(SP-2) [Shulman, M. et al. Nature, 276, 269–270 (1978)], P3X63Ag8.653 (653) [Kearney, J. F. et al. J. Immunology, 123, 1548–1550 (1979)] and P3X63Ag8 (X63) [Horibata, K. and Harris, A. W. Nature, 256, 495–497 (1975)] are preferably used. These cell lines are sub-cultured in, for example, a 8-azaguanine medium [the medium prepared by adding 8-azaguanine to an RPMI-1640 medium supplemented with glutamine, 2-mercaptoethanol, gentamicin and fetal calf serum (hereinafter referred to as "FCS")], Iscove's Modified Dulbecco's Medium (hereinafter referred to as "IMDM") or Dulbecco's Modified Eagle Medium (hereinafter referred to as "DMEM"). Subculture is performed using a normal medium 3 to 4 days before cell fusion (e.g., DMEM medium containing 10% FCS), and $2 \times 10^7$ or more cells are ensured at the day of cell fusion.

(4) Cell Fusion

Antibody-producing cells are plasma cells, or lymphocytes that are progenitor cells thereof, and may be obtained from any site of an individual. In general, the cells can be obtained from, for example, the spleen, lymph node, bone marrow, tonsil, peripheral blood or an appropriate combination thereof. Splenocytes are most generally used.

After the final immunization, for example, the spleen, which is a site where antibody-producing cells are present, is excised from the mouse from which a given antibody titer is obtained, thereby preparing splenocytes, the antibody-producing cells. Currently, the most generally employed means for fusing the splenocytes with the myeloma obtained in step (3) is a method using polyethylene glycol, which has a relatively low cytotoxicity and with which the fusion procedure is simple. For example, this method comprises the following steps.

Splenocytes and myeloma are washed well in a serum-free medium (e.g., DMEM) or a phosphate-buffered saline (hereinafter referred to as "PBS"), and then mixed well to have a cell number ratio of splenocytes to myeloma of approximately 5:1 to 10:1, followed by centrifugation. The supernatant is removed, and then the precipitated cell groups are well disassembled. 1 ml of a 50% (w/v) polyethylene glycol (molecular weight of 1000 to 4000)-containing serum-free medium is dropped onto the precipitate while stirring. Subsequently, 10 ml of a serum-free medium is slowly added, and then centrifugation is performed. The supernatant is discarded again. The precipitated cells are suspended in a normal medium containing an appropriate amount of hypoxanthine, aminopterin, thymidine (hereinafter referred to as "HAT") solution (hereinafter referred to as "HAT medium") and human interleukin-6 (hereinafter referred to as "IL-6"), added in each well of a plate for culturing (hereinafter referred to as "plate"), and then cultured in the presence of 5% carbon dioxide gas at 37° C. for approximately 2 weeks. Supplementation with a HAT medium is appropriately performed during culturing.

(5) Selection of Hybridoma Group

When the above myeloma cells are cells of an 8-azaguanine resistant strain, that is, the cells of a hypoxanthine guanine phosphoribosyltransferase (HGPRT)-deficient strain, unfused myeloma cells and myeloma—myeloma fusion cells are unable to survive in a HAT-containing medium. While a fusion cell of two antibody-producing cells, or a hybridoma of an antibody-producing cell and a myeloma cell can survive, the fusion cell of two antibody-producing cells has a limited life span. Thus, when culturing in a HAT-containing medium is continued, only hybridomas of antibody-producing cells and myeloma cells survive, so that the hybridoma can be selected.

For hybridomas grown to form colonies, the HAT medium is exchanged with a medium from which aminopterin has been removed (hereinafter referred to as "HT medium"). Subsequently, a part of the culture supernatant is collected, and then, for example, anti-TRAIL-R1 and R2 antibody titers are measured by the ELISA method. However, when the above fusion protein is used as an antigen for ELISA, a step of removing clones producing antibodies that specifically bind to the Fc region of human IgG is required so as not to select such a clone. The presence or absence of such a clone can be confirmed by, for example, ELISA using the Fc region of human IgG as an antigen.

The method using the 8-azaguanine resistant cell strain is as illustrated above. Other cell strains can also be used depending on a selection method for hybridomas. In this case, a medium composition to be used varies depending on the method used.

(6) Cloning Step

Hybridomas that have been shown to produce specific antibodies by measuring antibody titer in a manner similar to that described in (2) are transferred to another plate and then subjected to cloning. Examples of the cloning method include the limiting dilution method wherein dilution is performed to cause each well of a plate to contain one hybridoma, followed by culturing; the soft agar method, wherein culturing is performed in a soft agar medium and then colonies are collected; a method wherein each cell is picked with a micromanipulator and then the cell is cultured; and the sorter clone method, wherein one cell is separated with a cell sorter. The limiting dilution method is convenient, and is often used.

For the wells in which antibody titer has been detected, for example, cloning is repeated 2 to 4 times by the limiting dilution method, and then strains that have stable antibody titers are selected as anti-TRAIL-R1 and R2 monoclonal antibody-producing hybridoma strains.

In addition, a mouse—mouse hybridoma H-48-2 which is the human anti-TRAIL-R2 monoclonal antibody-producing cell of the present invention, was internationally deposited with International Patent Organism Depositary at the National Institute of Advanced Industrial Science and Technology (Central 6, 1-1-1, Higashi, Tsukuba, Ibaraki, Japan) on May 18, 2001. The international accession number is FERM BP-7599. In addition, a hybridoma E-11-13 was internationally deposited under the accession number of FERM BP-7698, a hybridoma F-4-8 under the accession number of FERM BP-7699, and a hybridoma L-30-10 under the accession number of FERM BP-7700 on Aug. 8, 2001. In addition, a hybridoma 0304 was internationally deposited under the accession number of FERM BP-8037, and a hybridoma KMTR1 under the accession number of FERM BP-8038 on May 10, 2002. Hence, for example, when antibodies are prepared using the mouse—mouse hybridomas, the antibodies can be prepared by step (7) and the following steps (described below) while omitting steps (1) to (6). Moreover, culturing is performed in vivo, for example, in mouse ascites, and then antibodies can be isolated from the ascites.

(7) Preparation of Monoclonal Antibody by Culturing Hybridoma

After the completion of cloning, the hybridoma is cultured in a normal medium to which HT medium is exchanged.

Mass culture is performed by the roll-streak system using a large culture bottle, or by the spinner culture method. The supernatant in the mass culture is purified using a method known by a person skilled in the art such as gel filtration, so that anti-TRAIL-R1 and R2 monoclonal antibodies which are contained in the prophylactic or the therapeutic agent of the present invention as an active ingredient can be obtained. Furthermore, proliferation of the hybridoma intraperitoneally in, for example, mice of the same line (e.g., BALB/c) or Nu/Nu mice, rats, guinea pigs, hamsters or rabbits makes it possible to obtain ascites containing a large amount of anti-TRAIL-R1 and R2 monoclonal antibodies which are contained in the prophylactic or the therapeutic agent of the present invention as an active ingredient. As a convenient purification method, for example, a commercially available monoclonal antibody purification kit (e.g., MAbTrap GII kit; Amersham Pharmacia Biotech) can also be used.

Monoclonal antibodies thus obtained have high antigen specificity against the human TRAIL-R1 and R2.

(8) Verification of Monoclonal Antibody

The isotype and the subclass of the thus-obtained monoclonal antibody can be determined as follows. Examples of identification method include the Ouchterlony method, the ELISA method and the RIA method. Although the Ouchterlony method is convenient, an enrichment step is required when the concentration of monoclonal antibodies is low.

In contrast, when the ELISA method or the RIA method is used, the culture supernatant is allowed to react intact with an antigen-coated solid phase. By further using antibodies to various immunoglobulin isotypes and subclasses as secondary antibodies, the isotype and the subclass of the monoclonal antibody can be identified.

Furthermore, protein quantification can be performed by the Folin-Lowry method, and a calculation method using absorbance at 280 nm [1.4(OD280)=immunoglobulin 1 mg/ml].

Epitopes to be recognized by monoclonal antibodies can be identified as follows. First, various partial structures of a molecule that the monoclonal antibody recognizes are prepared. To prepare the partial structures, for example, there exist a method whereby various partial peptides of the molecule are produced using a known oligopeptide synthesis technique and a method whereby DNA sequences encoding target partial peptides are integrated into appropriate expression plasmids using genetic engineering techniques, and then the peptides are produced inside and outside a host such as *Escherichia coli*. In general, both methods are used in combination for the above purpose. For example, a series of polypeptides are prepared to be appropriately shorter in length sequentially from the C-terminus or the N-terminus of an antigen protein, using a genetic engineering technique known to a person skilled in the art. Then, the reactivities of the monoclonal antibody against them are studied, so that the approximate recognition site is determined.

Next, more specifically, various oligopeptides corresponding to the site, mutants or the like of the peptides are synthesized using an oligopeptide synthesis technique known to a person skilled in the art. Then, the ability of the monoclonal antibody (contained as an active ingredient in the prophylactic or the therapeutic agent of the present invention) to bind to these peptides is examined, or the activity of competitive inhibition of the peptide on the binding of the monoclonal antibody with the antigen is examined, thereby specifying the epitope. As a convenient method for obtaining various oligopeptides, a commercially available kit (e.g., SPOTs kit, GENOSYS BIOTECHNOLOGIES), a kit for a series of multipin peptide synthesis (Chiron) using the multipin syntheses method or the like can also be used.

Moreover, a gene encoding a human monoclonal antibody is cloned from an antibody-producing cell such as a hybridoma, the gene is integrated into an appropriate vector, and then the vector is introduced into a host (e.g., a mammalian cell line, *Escherichia coli*, yeast cells, insect cells or plant cells). Thus, recombinant antibodies that are produced using the gene recombinant technique can be prepared (P. J. Delves., ANTIBODY PRODUCTION ESSENTIAL TECHNIQUES., 1997 WILEY, P. Shepherd and C. Dean., Monoclonal Antibodies., 2000 OXFORD UNIVERSITY PRESS, J. W. Goding., Monoclonal Antibodies: principles and practice., 1993 ACADEMIC PRESS).

A method employed to prepare a gene encoding a monoclonal antibody from a hybridoma comprises the step of preparing by the PCR method and the like DNAs respectively encoding the light chain variable region, light chain constant region, heavy chain variable region and heavy chain constant region of the monoclonal antibody. In this case, oligo DNAs designed from the anti-TRAIL-R antibody gene or amino acid sequence can be used as primers, and DNA prepared from the hybridoma can be used as a template. These DNAs are integrated into an appropriate vector, and then the vector is introduced into a host for expression. Alternatively, these DNAs are separately integrated into appropriate vectors, thereby causing co-expression.

Examples of vectors used herein include phages or plasmids that can autonomously grow in a host microorganism. Examples of the plasmid DNA include plasmids derived from *Escherichia coli, Bacillus subtilis* or yeast. An example of the phage DNA is a λ phage.

Examples of the host used for transformation are not specifically limited, as long as it can express a target gene, and include bacteria (e.g., *Escherichia coli* and *Bacillus subtilis*), yeast, animal cells (e.g., COS cells and CHO cells) and insect cells.

Methods for introducing a gene into a host are known, and any such method may be used (e.g., a method using calcium ion, the electroporation method, the spheroplast method, the lithium acetate method, the calcium phosphate method and the lipofection method). In addition, examples of a method for introducing a gene into an animal (described later) include the microinjection method, a method for introducing a gene into ES cells by the electroporation or the lipofection method, and the nucleus transplantation method.

In the present invention, anti-TRAIL-R antibodies can be obtained by culturing transformants and collecting the antibodies from the culture product. The term "culture product" means any of (a) a culture supernatant, (b) cultured cells or cultured microbes or the disrupted cells or microbes thereof, or (c) the secretion product of the transformant. To culture transformants, a medium appropriate for the host used herein is used, and the static culture method, a culture method using a roller bottle or the like is employed.

After culturing, when a target protein is produced within microbes or cells, antibodies are collected by disrupting the microbes or the cells. Furthermore, when a target antibody is produced outside the microbes or the cells, the culture solution is used intact, or the microbes or cells are removed by centrifugation or the like. Subsequently, a target antibody can be isolated and purified from the above culture product using one of or an appropriate combination of general biochemical methods with various chromatographies that are used for protein isolation and purification.

Moreover, by the use of transgenic animal generation techniques, animal hosts having the gene of a target antibody integrated in the endogenous gene are generated, such as transgenic cattle, transgenic goats, transgenic sheep or transgenic pigs. The antibody gene-derived monoclonal antibodies can then be obtained in large quantities from the milk to be secreted from the transgenic animal (Wright, G., et al. (1991) Bio/Technology 9, 830–834). Hybridomas can be cultured in vitro using a known nutrition medium, which is used to allow the proliferation, maintenance, and storage of the hybridoma so as to cause the hybridoma to produce monoclonal antibodies in the culture supernatant depending on various conditions such as the characteristics of a cell type to be cultured, the purpose of an experiment or study, and a culture method; or any nutrition medium, which is induced and prepared from a known basic medium.

(9) Characteristics of Antibody

The antibody of the present invention has the following functional properties (a) to (c), and each of the properties can be confirmed by, for example, the method described for each of (a) to (c).

(a) When human carcinoma cells are cultured, the antibody of the present invention is contained in the medium, and the survival rate of the cells is examined, the antibody has activity to induce apoptosis in carcinoma cells expressing TRAIL-R1 and/or R2.

(b) When normal human tissue-derived cells are cultured, the antibody of the present invention is contained in the medium, and the survival rate of the cells is examined, the antibody does not have effect on normal cells expressing TRAIL-R1 and/or R2.

(c) When human hepatocytes are cultured, the antibody of the present invention is contained in the medium, and the survival rate of the cells is examined, the antibody does not induce hepatocyte toxicity.

The apoptosis-inducing activity of the antibody of the present invention can be expressed using an LD50 value (an antibody concentration, which causes death in half of the cells under a given experimental condition) as an indicator. The LD50 value is 100 µg/ml or less, preferably 10 µg/ml or less, more preferably 0.7 µg/ml or less, further preferably 0.02 to 0.11 µg/ml, or most preferably 0.02 µg/ml or less in the experimental conditions described hereinafter.

Furthermore, the term "does not have effect on normal cells" or "does not induce hepatocyte toxicity" means that the apoptosis-inducing activity of the antibody of the present invention on normal cells (human hepatocytes) is not significantly high. When an LD50 value is used as an indicator, it is 0.01 µg/ml or more, preferably 0.1 µg/ml or more, more preferably 2 to 10 µg/ml, further preferably 10 to 24 µg/ml or most preferably 24 µg/ml or more in the experimental conditions described hereinafter.

The antibody of the present invention has any of the above activities (a) to (c). The antibody is a substance having novel characteristics in that it preferably has the above activity (a) of inducing apoptosis in carcinoma cells, and the above activities (b) and (c) of not inducing damage on normal cells, particularly normal hepatocytes. Therefore, the antibody of the present invention is useful as an ingredient to be contained in a prophylactic or therapeutic agent against malignant tumors.

Apoptosis-inducing activity on normal cells or carcinoma cells can be expressed using an LD50 value as an indicator. The LD50 value in the present invention can be calculated as follows. Normal cells (e.g., human heptocytes) or carcinoma cells (e.g., human colon cancer cell line Colo205; ATCC CCL-222) are cultured, and then the antibody of the present invention is added to a medium. After a certain period of time, the survival rate of the cells is measured by MTT assay (Green, L. M. et al., J. Immunological Methods, 70: 257–268 (1984)), LDH assay or the like.

Based on a graph on which the survival rate and the concentration of the antibody added are plotted, an antibody concentration corresponding to a survival rate of 50% is determined as an LD50 value.

The LD50 value can be read from a graph, or calculated by finding a formula for a graph curve by regression calculation.

In an experiment for carcinoma cells (Colo205), $2.5 \times 10^3$ cells are seeded in 100 µl of a medium per well of a 96-well flat-bottomed plate, and then cultured at 37° C. in the presence of 5% $CO_2$. On the next day, the antibodies are added, the mixture is allowed to stand for 48 hours in the above environment, and then the survival rate of the cells is measured (total volume of the reaction solution: 110 to 120 µl). In the present invention, the above conditions are described as "number of cells: $2.5 \times 10^3$ and reaction time: 48 hours."

In an experiment for normal cells (hepatocytes), $7.5 \times 10^4$ cells are seeded in 100 µl of a medium per well of a 96-well flat-bottomed plate, and then cultured at 37° C. in the presence of 5% $CO_2$. On the next day, the antibodies are added, the mixture is allowed to stand for 24 hours in the above environment, and then the survival rate of the cells is measured (total volume of the reaction solution: 110 to 120 µl). In the present invention, the above conditions are described as "number of cells: $7.5 \times 10^4$ and reaction time: 24 hours."

The antibody of the present invention includes antibodies having a property of showing an LD50 value for normal cells (human hepatocytes) of, for example, 0.01 µg/ml (10 ng/ml) or more, or preferably 0.1 µg/ml or more when the LD50 value is measured under the above conditions. It can be said that the higher the LD50 value against normal cells, the higher the safety. Thus, antibodies having LD50 values of 2 to 100 µg/ml are further preferred. The antibody of the present invention includes antibodies having a property of showing the LD50 value for carcinoma cells of, for example, 100 µg/ml or less, or preferably 0.7 µg/ml or less when the LD50 value is measured under the above conditions. It can be said that lower the LD50 value against carcinoma cells, the stronger the activity to kill tumor cells. Thus, antibodies having LD50 values of 0.02 to 0.11 µg/ml are further preferred. In particular, the E-11-13 antibody, the L-30-10 antibody and the KMTR1 antibody of the present invention have properties of showing LD50 values for human hepatocytes of 2 to 100 µg/ml or more (for example, 2 to 24 µg/ml, preferably, 100 µg/ml) and LD50 values for carcinoma cells of 0.02 to 0.11 µg/ml. That is, these antibodies have both safety for normal cells and an apoptosis-inducing effect on tumor cells. Furthermore surprisingly, the antibody of the present invention significantly suppressed tumor cell proliferation in a tumor-bearing mouse model.

The ratio of the LD50 value for normal cells measured under conditions where "number of cells: $7.5 \times 10^4$ and reaction time: 24 hours" to the LD50 value for carcinoma cells measured under conditions where "number of cells: $2.5 \times 10^3$ and reaction time: 48 hours" is next examined. As described above, the higher the LD50 value for normal cells, the higher the safety, and the lower the LD50 value for carcinoma cells, the stronger the activity to kill tumor cells. Hence, antibodies having a higher ratio of the LD50 value for normal cells to that for carcinoma cells can be said to be useful (higher safety and stronger apoptosis-inducing activity in carcinoma cells). The ratio of the LD50 value for carcinoma cells to that for normal cells (showing how many times the LD50 value for normal cells is greater than that for carcinoma cells) is supposed to be an N/C ratio. The antibody of the present invention has a property of having N/C=2 or more, namely, having a LD50 value for normal cells which is twice or more greater than that for carcinoma cells. Preferably the LD50 for normal cells is 10 times or more greater (N/C=10 or more) than that for carcinoma cells, more preferably, N/C=10 to 25. Hereinafter, the N/C ratio, in order of preference, is as follows: N/C=50, N/C=50 or more, N/C=50 to 100, N/C=100 or more, N/C=100 to 1000, N/C=250 to 1000 and most preferably N/C=1000 or more.

Pharmaceutical Composition

A preparation containing a preparation that is prepared by purifying the human anti-TRAIL-R1 and R2 antibodies of the present invention is also encompassed within the scope of the present invention. Such a preparation preferably contains a physiologically acceptable diluent or carrier in addition to the antibody, and may be a mixture with other antibodies or other drugs such as antibiotics. Examples of an appropriate carrier include, but are not limited to, a physiological saline solution, a phosphate buffered saline solution, a phosphate buffered saline glucose solution and a buffered physiological saline. Alternatively, the antibody may be freeze-dried, and then used when necessary by adding the above buffered aqueous solution for reconstitution. The prophylactic or therapeutic agent can be administered in various forms. Examples of the forms of administration of these agents include oral administration using vehicles such as tablets, capsules, granules, powders or syrups, and parenteral administration using vehicles such as injections, drops or suppositories.

The dose differs depending on symptom, age, body weight and the like. Normally in the case of oral administration, the dose is approximately 0.01 mg to 1000 mg per day for an adult, and it can be administered once or separately administered on several different occasions. Further, in the case of parenteral administration, a dose of approximately 0.01 mg to 1000 mg per administration can be administered by subcutaneous injection, intramuscular injection or intravenous injection.

The antibody or the pharmaceutical composition of the present invention can be applied to treatment of or prophylaxis against various diseases or symptoms that may be caused by cells expressing TRAIL-R1 and R2. Examples of such diseases or the symptoms include various malignant tumors.

Examples of the types of such tumors include colon cancer, colorectal cancer, lung cancer, breast cancer, brain tumor, malignant melanoma, renal cell carcinoma, bladder cancer, leukemia, lymphomas, T cell lymphomas, multiple myeloma, gastric cancer, pancreas cancer, cervical cancer, endometrial carcinoma, ovarian cancer, esophageal cancer, liver cancer, head and neck squamous cell carcinoma, cutaneous cancer, urinary tract carcinoma, prostate cancer, choriocarcinoma, pharyngeal cancer, laryngeal cancer, thecomatosis, androblastoma, endometrium hyperplasy, endometriosis, embryoma, fibrosarcoma, Kaposi's sarcoma, hemangioma, cavernous hemangioma, angioblastoma, retinoblastoma, astrocytoma, neurofibroma, oligodendroglioma, medulloblastoma, ganglioneuroblastoma, glioma, rhabdomyosarcoma, hamartoblastoma, osteogenic sarcoma, leiomyosarcoma, thyroid sarcoma and Wilms tumor. The number of the types of tumors to which the antibody of the present invention is applied is not limited to one type, and plural types of tumors may develop at the same time.

Example of Preparation

The molecule of the present invention is used in the form of an ampule of aseptic solution or suspension prepared by dissolving the molecule in water or a pharmacologically acceptable solution other than water. In addition, an ampule may be filled with an aseptic powder preparation (preferably, where the molecule of the present invention is freeze-dried), and it can be diluted with a pharmacologically acceptable solution when used.

BRIEF DESCRIPTION OF THE DRAWINGS

FIG. 5a shows a graph depicting the cell-death-inducing activity of human recombinant TRAIL (positive control) on Colo205 and normal human hepatocytes. A solid line with solid circles (-●-) represents normal human hepatocyte, and a dotted line with solid diamond-shaped symbols (--□--) represents Colo205 cells.

FIG. 5b shows a graph depicting the cell-death-inducing activity of purified human anti-TRAIL-R2 monoclonal antibodies (H-48-2) on Colo205 and normal human hepatocytes. A solid line with solid circles (-●-) represents normal human hepatocyte, and a dotted line with solid diamond-shaped symbols (--□--) represents Colo205 cells.

FIG. 5c shows a graph depicting the cell-death-inducing activity of purified human anti-TRAIL-R2 monoclonal antibodies (E-11-13) on Colo205 and normal human hepatocytes. A solid line with solid circles (-●-) represents normal human hepatocyte, and a dotted line with solid diamond-shaped symbols (--□--) represents Colo205 cells.

FIG. 5d shows a graph depicting the cell-death-inducing activity of purified human anti-TRAIL-R2 monoclonal antibodies (L-30-10) on Colo205 and normal human hepatocytes. A solid line with solid circles (-●-) represents normal human hepatocyte, and a dotted line with solid diamond-shaped symbols (--□--) represents Colo205 cells.

FIG. 5e shows a graph depicting the cell-death-inducing activity of purified human anti-TRAIL-R2 monoclonal antibodies (F-4-8) on Colo205 and normal human hepatocytes. A solid line with solid circles (-●-) represents normal human hepatocyte, and a dotted line with solid diamond-shaped symbols (--□--) represents Colo205 cells.

FIG. 5f shows a graph depicting the cell-death-inducing activity of purified human anti-TRAIL-R2 monoclonal antibodies (W-40-5) on Colo205 and normal human hepatocytes. A solid line with solid circles (-●-) represents normal human hepatocyte, and a dotted line with solid diamond-shaped symbols (--□--) represents Colo205 cells.

FIG. 5i shows a graph depicting the cell-death-inducing activity of purified human anti-TRAIL-R2 monoclonal antibodies (KMTR1) on Colo205 and normal human hepatocytes. A solid line with solid circles (-●-) represents normal human hepatocyte, and a dotted line with solid diamond-shaped symbols (--□--) represents Colo205 cells.

FIG. 5j shows a graph depicting the cell-death-inducing activity of purified human anti-TRAIL-R2 monoclonal antibodies (D1M) on Colo205 and normal human hepatocytes. A solid line with solid circles (-●-) represents normal human hepatocyte, and a dotted line with solid diamond-shaped symbols (--□--) represents Colo205 cells.

FIG. 5k shows a graph depicting the cell-death-inducing activity of purified human anti-TRAIL-R2 monoclonal antibodies (0304, Goat anti-human IgG antibodies were not added) on Colo205 and normal human hepatocytes. A solid line with solid circles (-●-) represents normal human hepatocyte, and a dotted line with solid diamond-shaped symbols (--□--) represents Colo205 cells.

FIG. 5l shows a graph depicting the cell-death-inducing activity of purified human anti-TRAIL-R2 monoclonal antibodies (KMTR1, Goat anti-human IgG antibodies were not added) on Colo205 and normal human hepatocytes. A solid line with solid circles (-●-) represents normal human hepatocyte, and a dotted line with solid diamond-shaped symbols (--□--) represents Colo205 cells.

BEST MODE FOR CARRYING OUT THE INVENTION

Figure 1:
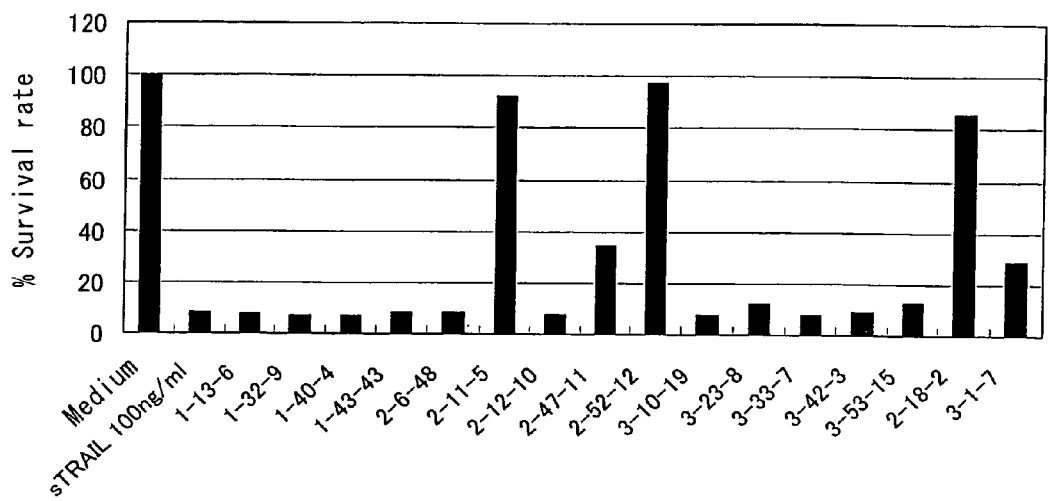
FIG. 1 shows the cell-death-inducing activity on Colo205 in the culture supernatant of hybridomas producing human anti-TRAIL-R1 monoclonal antibodies.

The present invention will be described more specifically by the following examples. The present invention is not limited to the embodiments described in these examples.

Example 1

Preparation of Antigen

To obtain cells excessively expressing human TRAIL-R1 and TRAIL-R2 on the cell membrane, plasmid vectors for the expression of human TRAIL-R1 and human TRAIL-R2 (which had been prepared by removing the death domain and the amino acids on the C-terminal side from the death domain in the intracellular regions from the full-length amino acids of the human TRAIL-R1 and TRAIL-R2, hereinafter referred to as TRAIL-R1 and TRAIL-R2delta,) were prepared. DNAs encoding TRAIL-R1 and TRAIL-R2delta were prepared by the PCR method.

a) Construction of Full-Length Human TRAIL-R1 and R2 Expression Vectors

To perform template PCR, plasmid vectors, pcDNA3-TRAIL-R1 and pcDNA3-TRAIL-R2, retaining cDNAs encoding human TRAIL-R1 and R2 were used as templates. pcDNA3-TRAIL-R1 and pcDNA3-TRAIL-R2 were constructed by the following method. The full-length human TRAIL-R1 DNA and TRAIL-R2 DNA were modified by polymerase chain reaction (PCR) to add an EcoR I sequence to the 5' end, and a Not I sequence and a termination codon to the 3' end. Using human placenta-derived cDNA (Clontech) as a template, primers 5'-CACGAATTCACCATG-GCGCCACCACCAGCT-3' (SEQ ID NO: 1) and 5'-TTTCTCGAGGCGGCCGCTTATCACTC-CAAGGACACGGCAGAGCCTGT G-3' (SEQ ID NO: 2) synthesized for TRAIL-R1, and primers 5'-CACGAAT-TCGCCACCATGGAACAACGGGGACAG-3' (SEQ ID NO: 3) and 5'-TTTCTCGAGGCGGCCGCTCATTAGGA-CATGGCAGAGTCTGCATTACCT-3' (SEQ ID NO: 4) synthesized for TRAIL-R2, a PCR reaction was performed for 30 cycles (each cycle consisting of 94° C. for 20 seconds, 60° C. for 30 seconds and 68° C. for 90 seconds) using platinum PfxDNA polymerase (Gibco BRL). The modified TRAIL-R1 and TRAIL-R2 sequences were isolated as EcoR I-Not I fragments, and then ligated to pcDNA3 (Invitrogen) vectors that had been cleaved with the same enzymes. The obtained plasmids were named pcDNA3-TRAIL-R1 and pcDNA3-TRAIL-R2. Of the two fragments formed by alternative splicing, TRAIL-R2 integrated in pcDNA3-TRAIL-R2 comprises 440 amino acids encoded by a 1320 bp cDNA. Hereinafter, the reaction temperature for all the PCRs in the examples was regulated using a GeneAmp PCR system 9700 (Perkin Elmer Japan).

b) Construction of Human TRAIL-R1 and R2Delta Expression Vectors

Human TRAIL-R1 and R2delta expression vectors were constructed by the following methods. To prepare an expression plasmid comprising a TRAIL-R1 partial peptide having an amino acid sequence of 1 to 351, and the same comprising a TRAIL-R2 partial peptide having an amino acid sequence of 1 to 348, PCR reaction was performed to add an EcoR I sequence to the 5' ends of the TRAIL-R1 and R2 partial peptides, and an Not I sequence and a termination codon to the 3' ends of the same. PCR was performed for 25 cycles (each cycle consisting of 94° C. for 20 seconds, 65° C. for 30 seconds and 68° C. for 75 seconds) using oligonucleotide primers 5'-CACGAATTCACCATGGCGCCAC-CACCAGCT-3' (SEQ ID NO: 1) and 5'-TTCTACGAGCG-GCTTATCACAGCCTCCTCCTCTGAGA-3' (SEQ ID NO: 5) for TRAIL-R1, and oligonulcotide primers 5'-CAC-GAATTCGCCACCATGGAACAACGGGGACAG-3' (SEQ ID NO: 3) and 5'-TTCTACGAGCGGCCGCTTAT-CACAAGTCTGCAAAGTCATC-3' (SEQ ID NO: 6) for TRAIL-R2, platinum PfxDNA polymerase (Gibco BRL), pcDNA3-TRAIL-R1 and pcDNA3-TRAIL-R2. The modified TRAIL-R1 and R2 partial peptides were isolated as EcoR I-Not I fragments. The EcoR I-Not I fragment was ligated to pEFneo vectors that had been cleaved with EcoR I and Not I enzymes. The obtained plasmids were named pEF-TRAIL-R1delta and pEF-TRAIL-R2delta.

c) Preparation of Human TRAIL-R1 and R2Delta-Expressing Cells pEF-TRAIL-R1delta and pEF-TRAIL-R2delta prepared in b) were introduced into L929 cells (American Type Culture Collection No. CCL-1) using LipofectAMINE Plus (Gibco BRL). Transfection was performed by the method described in the manual. After 24 hours of culturing in a flask for culturing cells (with a culture area of 75 cm 2) at 37° C. under 5.0% carbon dioxide gas, G418 (Gibco BRL) was added at 1 mg/ml in the culture, followed by 1 week of culturing. Subsequently, FACS analysis was performed using goat anti-human TRAIL-R1 polyclonal antibodies and goat anti-human TRAIL-R2 polyclonal antibodies (DAKO). Thus, it was confirmed that the transfected cells, which had acquired a G418 resistance trait, expressed TRAIL-R1delta comprising 351 amino acids and TRAIL-R2delta comprising 348 amino acids on the cell membrane surface.

The synthesis of oligonucleotides such as primers for PCR was always performed using an automated DNA synthesis system (model 3948, Perkin Elmer Japan, Applied Biosystems division) according to the manual [see Matteucci, M. D. and Caruthers, M. H. (1981) J. Am. Chem. Soc. 103, 3185–3191]. After the end of synthesis, each oligonucleotide was cleaved from the support and then deprotected. The obtained solution was dried and solidified, and the product was dissolved in distilled water, and then cryopreserved at −20° C. until use.

Example 2

Generation of Human Antibody-Producing Mice

The mice used for immunization had a genetic background whereby they were homozygotes for both disrupted endogenous Ig heavy chain and κ light chain, and the mice harbored at the same time chromosome 14 fragment (SC20) containing a human Ig heavy chain locus, and a human Igκ chain transgene (KCo5). These mice were generated by crossing mice of a line A having a human Ig heavy chain locus with mice of a line B having a human Igκ chain transgene. The mice of line A are homozygotes for both disrupted endogenous Ig heavy chain and κ light chain, and harbor chromosome 14 fragment (SC20), which is transmittable to progeny, as is described, for example, in the report of Tomizuka et al. (Tomizuka. et al., Proc Natl Acad Sci USA., 2000 Vol 97: 722). Furthermore, the mice of line B (transgenic mice) are homozygotes for both disrupted endogenous Ig heavy chain and κ light chain, and harbor a human Igκ chain transgene (KCo5), as described, for example, in the report of Fishwild et al. (Nat Biotechnol., 1996 Vol 14:845).

Progeny mice obtained by crossing male mice of the line A with female mice of the line B, or female mice of the line A with male mice of the line B, were analyzed by the method described in Tomizuka et al's report (Tomizuka et al., Proc Natl Acad Sci USA., 2000 Vol 97:722). Individuals (human antibody-producing mice) having human Ig heavy chain and K light chain detected simultaneously in the sera were screened for (Ishida & Lonberg, IBC's 11th Antibody Engineering, Abstract 2000; Ishida, I. et al., Cloning & Stem Cells 4, 85–96 (2002)) and used for the following immunization experiment. Mice having the altered genetic background of the above mice and the like (Isao ISHIDA, 2002, JIKKEN IGAKU 20, 6, 846–851) were also used for the immunization experiment. In addition, the above human antibody-producing mice are available from Kirin Brewery Co., Ltd via contract.

Example 3

Preparation of Human Monoclonal Antibodies Against Human TRAIL-R1 and R2

In this example, monoclonal antibodies were prepared according to general methods as described in, for example, Introduction of Experimental Protocols for Monoclonal Antibody (Monoclonal Antibody Jikken Sosa Nyumon, written by Tamie ANDO et al., KODANSHA, 1991). As immunogens, the TRAIL-R1 and R2delta-expressing L929 cell prepared in Example 1 or a fusion protein of the extracellular regions of human TRAIL-R1 and R2 and the Fc region of human IgG1 was used. Animals used for immunization were the human antibody (human immunoglobulin)-producing mice generated in Example 2.

To prepare human monoclonal antibodies against human TRAIL-R1, human antibody-producing mice were initially immunized via the right foot pad with the TRAIL-R1delta-expressing L929 cells ($3\times10^6$ cells/mouse) prepared in Example 1. After the initial immunization, immunization with the L929 cells was performed 10 times every 3 days via the left and right food pad alternatively. Furthermore, at 3 days before the obtainment of the spleen and the lymph node (described later), the L929 cells were used for immunization via both foot pads. To prepare human monoclonal antibodies against human TRAIL-R2, human antibody-producing mice ($1\times10^7$ cells/mouse) were initially immunized intraperitoneally with the TRAIL-R2delta-expressing L929 cells prepared in Example 1. After the initial immunization, immunization with the L929 cells was performed 5 or 6 times a week intraperitoneally. Furthermore, at 3 days before the obtainment of the spleen (described later) the L929 cells or a fusion protein of the extracellular region of human TRAIL-R2 and the Fc region of human IgG1 was used for immunization via the caudal vein. Moreover, the fusion protein comprising the extracellular region of human TRAIL-R2 and the Fc region of human IgG1 was mixed with Freund's complete adjuvant. The human antibody-producing mice were then initially immunized subcutaneously with the mixture. Subsequently, the same protein was mixed with Freund's incomplete adjuvant, and the mice were immunized twice subcutaneously with the mixture every 2 weeks. Furthermore, at 3 days before the obtainment of the spleen (described later), the same protein was used for immunization via the caudal vein.

The spleens and/or the lymph nodes were obtained by a surgical operation from the immunized mice. Then the organ was put into 10 ml of a serum-free DMEM medium (Gibco BRL) containing 350 mg/ml sodium hydrogen carbonate, 50 units/ml penicillin and 50 µg/ml streptomycin (hereinafter, referred to as "serum-free DMEM medium"). It was then pulverized using a spatula on mesh (Cell strainer: Falcon). The cell suspension that had passed through the mesh was centrifuged so as to precipitate the cells. The cells were washed twice in a serum-free DMEM medium, and suspended in a serum-free DMEM medium, and then the number of the cells was counted. In the meantime, myeloma cells SP2/0 (ATCC No. CRL-1581) that had been cultured so as not to exceed a cell concentration of $1\times10^8$ cells/ml at 37° C. in the presence of 5% carbon dioxide gas in a 10% FCS (Sigma)-containing DMEM medium (Gibco BRL) (hereinafter referred to as "serum-containing DMEM medium") were washed in a serum-free DMEM medium in the same manner. Then the cells were suspended in a serum-free DMEM medium, and then the number of the cells was counted. The collected cell suspension and the mouse myeloma suspension were mixed at a cell number ratio of 5:1. The mixture was centrifuged, thereby completely removing the supernatant. To this pellet, 1 ml of 50% (w/v) polyethylene glycol 1500 (Boehringer Mannheim) was gently added as a fusion agent while agitating the pellet using the tip of a pipette. Next, 1 ml of a serum-free DMEM medium preheated at 37° C. was gently added at two separate times, followed by addition of another 7 ml of serum-free DMEM medium. After centrifugation, the fusion cells obtained by the removal of the supernatant were subjected to screening by the limiting dilution method described below. Screening for hybridomas was performed by culturing the cells in DMEM media containing 10% fetal calf serum (FCS), hypoxanthine (H), aminopterin (A) and thymidine (T) (hereinafter referred to as "HAT": Sigma). Further, single clones were obtained using DMEM media containing 10% FCS and HT (Sigma) by the limiting dilution method. Culturing was performed in a 96-well microtiter plate (Beckton Dickinson). Screening for hybridoma clones producing anti-human TRAIL-R1 and R2 human monoclonal antibodies and characterization of the human monoclonal antibodies produced by each of the hybridomas were performed by the enzyme-linked immunosorbent assay (ELISA) and fluorescence activated cell sorter (FACS) described below, or by measuring the activity to induce cell death in carcinoma cells.

By ELISA described in Examples 4 and 5 and the FACS analysis described in Example 6, a large number of hybridomas producing human monoclonal antibodies that have human immunoglobulin γ chain (hIg γ) and human immunoglobulin light chain K, and have reactivity specifically to human TRAIL-R1 and/or R2 were obtained. Furthermore, in any of the following examples including this example, and tables and figures showing the test results of the examples, hybridoma clones producing each of the human anti-human TRAIL-R1 and R2 monoclonal antibodies of the present invention were denoted using symbols. A clone represented by symbols with the term "antibody" placed before or after the symbols means an antibody that is produced by each of the hybridomas, or a recombinant antibody that is produced by a host cell carrying an antibody gene (full-length or a variable region) isolated from the hybridoma. In addition, within a contextually clear range, the name of a hybridoma clone may express the name of an antibody. The following hybridoma clones represent single clones: 1-13, 1-18, 1-32, 1-40, 1-43, 2-6, 2-11, 2-12, 2-18, 2-47, 2-52, 3-1, 3-7, 3-10, 3-23, 3-33, 3-42, 3-53, 1-13-6, 1-32-9, 1-40-4, 1-43-43, 2-6-48, 2-11-5, 2-12-10, 2-47-11, 2-52-12, 3-10-19, 3-23-8, 3-33-7, 3-42-3, 3-53-15, 2-18-2, 3-1-7, E-11, E-14, E-30, N-18, X-14, E-11-13, E-14-4, F-4-2, F-4-8, H-48-2, L-30-10, N-18-12, W-40-5, X-14-4, X-51-4, X-51-12, A-11, G-3, H-34, 1-22, 1-35, J-21, J-26, K-8, K-16, K-57, L-4, P-28, P-36, W-42, X-13, X-60, Z-23, 1-39, A-4-27, A-4-29, G-3-10, H-34-2, K-57-12, W-42-2, 0304, 0322, KMTR1 and D1M. H-48-2 of these clones was internationally deposited with International Patent Organism Depositary at the National Institute of Advanced Industrial Science and Technology (Central 6, 1-1-1, Higashi, Tsukuba, Ibaraki, Japan) on May 18, 2001. The international accession number is FERM BP-7599. Furthermore, E-11-13, F-4-8 and L-30-10 were internationally deposited with the above deposition center on Aug. 8, 2001. The international accession number of E-11-13 is FERM BP-7698, that of F-4-8 is FERM BP-7699, and that of L-30-10 is FERM BP-7700. Furthermore, E-11-13, F-4-8 and L-30-10 were internationally deposited with the above deposition center on Oct. 11, 2001. The international accession number of E-11-13 is FERM BP-7770, that of F-4-8 is FERM BP-7768, and that of L-30-10 is FERM BP-7769. Furthermore, 0304 and KMTR1 were internationally deposited with the above deposition center on May 10, 2002. The international accession number of 0304 is FERM BP-8037, and that of KMTR1 is FERM BP-8038.

Example 4

Detection of Human Anti-TRAIL-R1 Monoclonal Antibody or Human Anti-TRAIL-R2 Monoclonal Antibody Having Human Immunoglobulin Light Chain κ (Igκ)

Fusion proteins of the extracellular regions of human TRAIL-R1 and R2 and the Fc region of human IgG1 (hereinafter referred to as "TRAIL-R1-hFc" and "TRAIL-R2-hFc" (ALEXIS). Regarding TRAIL-R2-hFc, a region comprising 1 to 183 amino acids was also used as the extracellular region of TRAIL-R2) were added at 0.5 µg/ml in phosphate buffered saline (hereinafter referred to as "PBS"). 50 µl of the thus prepared solution was added to each well of a 96-well microplate for ELISA (Maxisorp, Nunc) and incubated for 1 hour at room temperature or at 4° C. overnight, thereby coating TRAIL-R1-hFc or TRAIL-R2-hFc to the microplate. Subsequently the supernatant was discarded, a blocking reagent (SuperBlock (registered trademark) Blocking Buffer, PIERCE) was added to each well, and then incubation was performed at room temperature for 30 minutes, thereby blocking the part where TRAIL-R1-hFc or TRAIL-R2-hFc did not bind. Thus, a microplate having each well coated with TRAIL-R1-hFc or TRAIL-R2-hFc was prepared.

The culture supernatant of each hybridoma (50 µl) was added to each well, reaction was performed at room temperature for 1 hour, and then each well was washed twice in 0.1% Tween20-containing PBS (PBS-T). Subsequently, horseradish peroxidase-labeled goat anti-human Igκ antibodies (50 µl/well, Biosource International) were diluted 2000 times in PBS-T containing 10% Block Ace (Dainippon Pharmaceutical Co., Ltd.). 50 µl of the thus prepared solution was added to each well, and incubation was then performed at room temperature for 30 minutes. The microplate was washed three times with PBS-T, and then 100 µl of a TMB chromogenic substrate solution (DAKO) was added to each well, followed by incubation at room temperature for 20 minutes. 0.5M sulfuric acid was added (100 µl/well) to each well to stop reaction. Absorbance at a wavelength of 450 nm (reference wavelength of 570 nm) was measured with a microplate reader (MTP-300, Corona Electric). Moreover, antibodies produced by the hybridomas 0304, 0322, KMTR1 and D1M were subjected to the above experiment using the purified antibodies obtained by the method described in Example 10.

Table 1 and Table 2 show the characteristics of the part of antibodies among the thus obtained anti-human TRAIL-R1 and R2 antibodies. Table 1 shows the subclass and cross reactivity of the obtained human anti-TRAIL-R1 monoclonal antibodies. Table 2 shows the subclass and cross reactivity of the obtained human anti-TRAIL-R2 monoclonal antibodies.

TABLE 1

| Human anti-TRAIL-R1 | | Cross reactivity | |
|---|---|---|---|
| antibody | Subclass | TRAIL-R1 | TRAIL-R2 |
| 1-13 | IgG4 | + | − |
| 1-18 | IgG4 | + | − |
| 1-32 | IgG1 | + | − |
| 1-40 | IgG1 | + | − |
| 1-43 | IgG1 | + | − |
| 2-6 | IgG1 | + | − |
| 2-11 | IgG1 | + | − |

TABLE 1-continued

| Human anti-TRAIL-R1 antibody | Subclass | Cross reactivity | |
|---|---|---|---|
| | | TRAIL-R1 | TRAIL-R2 |
| 2-12 | IgG1 | + | − |
| 2-18 | IgM | + | − |
| 2-47 | IgG4 | + | − |
| 2-52 | IgG1 | + | − |
| 3-1 | IgM | + | − |
| 3-7 | IgM | + | − |
| 3-10 | IgG4 | + | − |
| 3-23 | IgG4 | + | − |
| 3-33 | IgG4 | + | − |
| 3-42 | IgG2 | + | − |
| 3-53 | IgG1 | + | − |

+: with reactivity
−: no reactivity

TABLE 2

| Human anti-TRAIL-R2 antibody | Subclass | Cross reactivity | |
|---|---|---|---|
| | | TRAIL-R1 | TRAIL-R2 |
| A-4-27 | IgM | − | + |
| A-4-29 | IgM | + | + |
| A-11 | IgM | − | + |
| E-11 | IgG1 | − | + |
| E-14 | IgG1 | − | + |
| F-4-2 | IgG4 | − | + |
| F-4-8 | IgG1 | − | + |
| G-3 | IgM | − | + |
| H-34 | IgM | − | + |
| H-48-2 | IgG1 | − | + |
| I-22 | IgM | − | + |
| I-35 | IgM | − | + |
| J-21 | IgM | − | + |
| J-26 | IgM | − | + |
| K-8 | IgM | − | + |
| K-16 | IgM | − | + |
| K-57 | IgM | − | + |
| L-4 | IgM | − | + |
| L-30 | IgG1 | − | + |
| N-18 | IgG4 | − | + |
| P-28 | IgM | − | + |
| P-36 | IgM | − | + |
| W-40-5 | IgG1 | − | + |
| W-42 | IgM | − | + |
| X-13 | IgM | − | + |
| X-14 | IgG4 | − | + |
| X-51-4 | IgG1 | − | + |
| X-51-12 | IgG4 | − | + |
| X-60 | IgM | − | + |
| Z-23 | IgM | − | + |
| 1-39 | IgM | − | + |
| 0304 | IgG4 | − | + |
| 0322 | IgG4 | − | + |
| KMTR1 | IgG1 | + | + |
| D1M | IgG1 | + | + |

+: with reactivity
−: no reactivity

Example 5

Identification of the Subclass of Each Monoclonal Antibody

A microplate having each well coated with TRAIL-R1-hFc or TRAIL-R2-hFc was prepared by a method similar to that of Example 4, and then each well was washed twice with PBS-T. The culture supernatant (50 μl) of each of the hybridomas obtained in Example 4 was added to each well of the microplate coated with TRAIL-R1-hFc or TRAIL-R2-hFc to perform reaction for 1 hour, and then each well was washed twice with PBS-T. Subsequently, sheep anti-human IgG1 antibodies, sheep anti-human IgG2 antibodies, or sheep anti-human IgG3 antibodies or sheep anti-human IgG4 antibodies, which had been respectively labeled with horseradish peroxidase and diluted 2000 times, were added (50 μl/well, The Binding Site) to each well, followed by incubation at room temperature for 1 hour. After washing 3 times with PBS-T, a substrate buffer (TMB, 100 μl/well, DAKO) was added to each well, and then incubation was performed at room temperature for 20 minutes. Next, 0.5M sulfuric acid (100 μl/well) was added to stop the reaction. Absorbance at a wave length of 450 nm (with a reference wavelength of 570 nm) was measured using a microplate reader (MTP-300, Corona Electric). In addition, antibodies produced by the hybridomas 0304, 0322, KMTR1 and D1M were subjected to the above experiment using the purified antibodies obtained by the method of Example 10. The above Table 1 and Table 2 show the results.

Example 6

Test of the Reactivity of Each Monoclonal Antibody to TRAIL-R1 and R2 Expressing Cells The reactivity of each of the monoclonal antibodies obtained in Example 4 to the TRAIL-R1delta-expressing L929 cells and TRAIL-R2delta-expressing L929 cells prepared in Example 1 was examined by FACS analysis. L929 cells, TRAIL-R1delta-expressing L929 cells and TRAIL-R2delta-expressing L929 cells were suspended at a concentration of $2 \times 10^6$/ml in a staining buffer (SB) of PBS containing 1% rabbit serum, 0.1% NaN$_3$ and 1% FCS. The cell suspension (100 μl/well) was added into a 96-well round-bottomed plate (Beckton Dickinson). After centrifugation (2000 rpm, 4° C., 2 minutes), the supernatant was removed and then the culture supernatant (50 μl) of the hybridoma cultured in Example 3 was added. The mixture was agitated, allowed to stand on ice for 30 minutes, and then subjected to centrifugation (2000 rpm, 4° C. for 2 minutes) to remove the supernatant. After the pellet was washed twice with SB (100 μl/well), 30 μl of 0.0125 mg/ml RPE fluorescence-labeled rabbit anti-human Igκ F(ab')$_2$ antibodies (DAKO) was added, and then incubation was performed on ice for 30 minutes. After washed twice with SB, the cells were suspended in 300 μl of SB, and then fluorescence intensity of each cell was measured by FACS (FACScan, Beckton Dickinson). As a result, all the antibodies were observed to have strong binding activity only to the TRAIL-R1delta-expressing L929 cells or the TRAIL-R2delta-expressing L929 cells, and no binding activity to L929 cells was observed. Thus, it was shown that they were antibodies binding specifically to TRAIL-R1 and TRAIL-R2.

Example 7

Cell-Death-Inducing Activity on Carcinoma Cells

Figure 2:
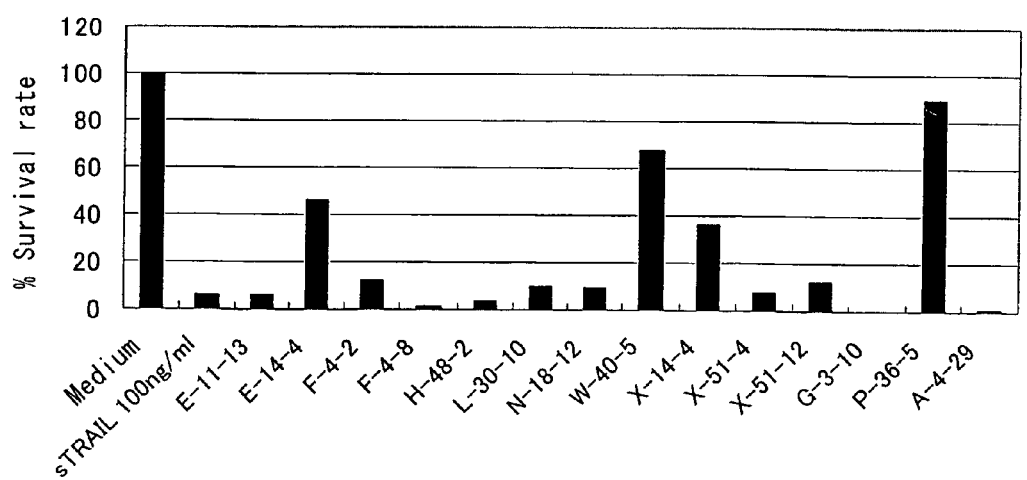
FIG. 2 shows the cell-death-inducing activity on Colo205 in the culture supernatant of hybridomas producing human anti-TRAIL-R2 monoclonal antibodies.
Figure 3:
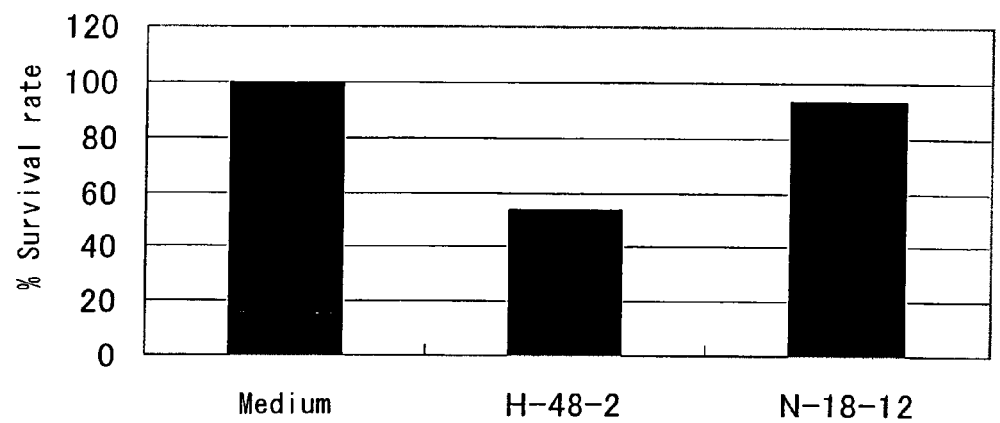
FIG. 3 shows the cell-death-inducing activity on Colo205 in the culture supernatant of hybridomas producing human anti-TRAIL-R2 monoclonal antibodies (Goat anti-human IgG(γ) specific polyclonal antibodies were not added).

Using the culture supernatant of the hybridoma producing the human anti-TRAIL-R1 monoclonal antibodies or the human anti-TRAIL-R2 monoclonal antibodies obtained from Example 3 or 4 to 6, cell-death-inducing activity on Colo205 (ATCC No. CCL-222) cells, which were colon carcinoma cells, was measured. Colo205 cells cultured in RPMI media containing 10% FCS were prepared at a concentration of $2.5 \times 10^4$/ml. 100 μl of the suspension was added to each well of a 96-well flat bottomed plate (Beckton Dickinson). After culturing at 37° C. under 5.0% carbon dioxide gas for 24 hours, the hybridoma culture supernatant was added at 50 μl/well. Furthermore, when the human anti-TRAIL-R1 monoclonal antibody or the human anti-TRAIL-R2 monoclonal antibody was IgG, goat anti-human IgG (γ)-specific polyclonal antibodies (Sigma) were added (10 μl/well) to each well at a final concentration of 5 μg/ml. For a part of the obtained hybridomas, wells not supplemented with goat anti-human IgG (γ)-specific polyclonal antibodies were prepared. As a positive control, human recombinant TRAIL protein (DAKO) was employed with a final concentration of 100 ng/ml. As a negative control, human IgG (Biogenesis) was employed. After 48 hours of culturing at 37° C. under 5.0% carbon dioxide gas, an MTS reagent (Cell Titer 96 AQ$_{UEOUS}$ Non-Radioactive Cell Proliferation Assay: Promega) was prepared according to the method described in the instructions, and then 20 μl of the reagent was added to each well. After another 2 hours of culturing at 37° C. under 5.0% carbon dioxide gas, absorbance at a wavelength of 490 nm (reference wavelength of 630 nm) was measured using a microplate reader (1420 ARVO multi-label counter: WALLAC). Using the reducibility of mitochondria as an indicator, the survival rate of the cells was calculated. The survival rate of the cells in each well was calculated by the following formula: Survival rate (%)=100×(a−b)/(c−b) (wherein "a" represents the measured value of a well tested, "b" represents the measured value of a cell-free well, and "c" represents the measured value of a negative control well). FIGS. 1 to 3 and Tables 3 and 4 show the results. Table 3 shows the cell-death-inducing activity (in the culture supernatant of the hybridomas producing the human anti-TRAIL-R1 monoclonal antibodies) on Colo205 and normal human hepatocytes. Table 4 shows the cell-death-inducing activity (in the culture supernatant of the hybridomas producing the human anti-TRAIL-R2 monoclonal antibodies) on Colo205 and human normal heptocytes.

TABLE 3

| Human anti-TRAIL-R1 antibody | Subclass | Normal human hepatocyte survival rate | Colo205 cell survival rate |
| --- | --- | --- | --- |
| 1-13-6 | IgG4 | − | − |
| 1-32-9 | IgG1 | − | − |
| 1-40-4 | IgG1 | − | − |
| 1-43-43 | IgG1 | − | − |
| 2-6-48 | IgG1 | − | − |
| 2-11-5 | IgG1 | ++ | ++ |
| 2-12-10 | IgG1 | − | − |
| 2-47-11 | IgG4 | + | + |
| 2-52-12 | IgG1 | ++ | ++ |
| 3-10-19 | IgG4 | − | − |
| 3-23-8 | IgG4 | − | − |
| 3-33-7 | IgG4 | − | − |
| 3-42-3 | IgG2 | − | − |
| 3-53-15 | IgG1 | − | − |
| 2-18-2 | IgM | ++ | ++ |
| 3-1-7 | IgM | − | + |
| sTRAIL 1 μg/ml | — | − | − |

++: Survival rate of 80% or more
+: Survival rate of 21% to 79%
−: Survival rate of 20% or less

TABLE 4

| Human anti-TRAIL-R2 antibody | Subclass | Normal human hepatocyte survival rate | Colo205 cell survival rate |
| --- | --- | --- | --- |
| E-11-13 | IgG1 | ++ | − |
| E-14-4 | IgG1 | + | + |
| F-4-2 | IgG4 | + | − |
| F-4-8 | IgG1 | − | − |
| H-48-2 | IgG1 | ++ | − |
| L-30-10 | IgG1 | ++ | − |
| N-18-12 | IgG4 | ++ | − |
| W-40-5 | IgG1 | ++ | + |
| X-14-4 | IgG4 | ++ | + |
| W-51-4 | IgG1 | − | − |
| X-51-12 | IgG4 | ++ | − |
| A-4-29 | IgM | − | − |
| G-3-10 | IgM | ++ | − |
| H-34-2 | IgM | − | − |
| K-57-12 | IgM | + | − |
| W-42-2 | IgM | − | − |
| sTRAIL 1 μg/ml | — | − | − |

++: Survival rate of 80% or more
+: Survival rate of 21% to 79%
−: Survival rate of 20% or less As a result, it was revealed that the human anti-TRAIL-R1 and R2 monoclonal antibodies clearly had activity to induce cell death in Colo205 cells, compared with the negative control. Moreover, it was shown that a part of the human anti-TRAIL-R2 monoclonal antibodies, which is IgG, had activity to induce cell death even in the absence of goat anti-human IgG(γ)-specific polyclonal antibodies (in a state without cross-linking with the human anti-TRAIL-R2 monoclonal antibodies).

Example 8

Cell-Death-Inducing Activity on Normal Cells

Cell-death-inducing activity on HUVEC (Biowhittaker), which is a normal human umbilical vein endothelial cell, was measured using the culture supernatant of the hybridomas producing the human anti-TRAIL-R2 monoclonal antibodies obtained in Examples 4 to 6. HUVEC cells cultured in an EGM-2 medium (Biowhittaker) were prepared at a concentration of 5×10$^4$/ml. 100 μl of the suspension was added to each well of a 96-well flat-bottomed plate (Beckton Dickinson). The cells were cultured at 37° C. under 5.0% carbon dioxide gas for 24 hours, and then the culture supernatant of the hybridoma was added at 50 μl/well. Further, when the human anti-TRAIL-R1 monoclonal antibody or the human anti-TRAIL-R2 monoclonal antibody was IgG, 10 μl of goat anti-human IgG(γ)-specific polyclonal antibodies (Sigma) were added at a final concentration of 5 μg/ml to each well. Human IgG (Biogenesis) was used as a negative control. After 48 hours of culturing at 37° C. under 5.0% carbon dioxide gas, an MTS reagent (Cell Titer 96 AQ$_{UEOUS}$ Non-Radioactive Cell Proliferation Assay: Promega) was prepared according to the method described in the instructions, and then 20 μl of the reagent was added to each well. After another 2 hours of culturing at 37° C. under 5.0% carbon dioxide gas, absorbance at a wavelength of 490 nm (with a reference wavelength of 630 nm) was measured using a microplate reader (1420 ARVO multi-label counter: WALLAC). Using the reducibility of mitochondria as an indicator, the survival rate of the cells was calculated. The survival rate of the cells of each well was calculated by a formula similar to that of Example 7.

Figure 4:
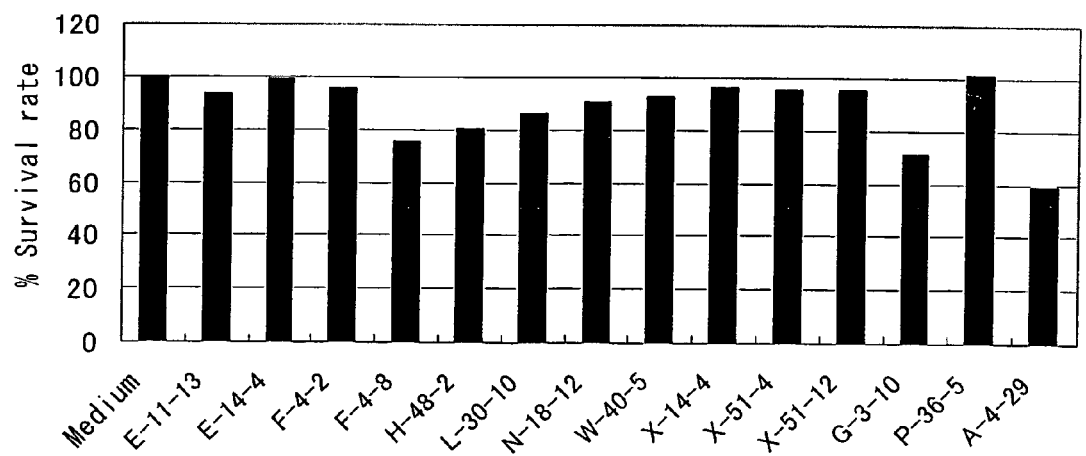
FIG. 4 shows the cell-death-inducing activity on HUVEC in the culture supernatant of hybridomas producing human anti-TRAIL-R2 monoclonal antibodies.
Figure 5G:
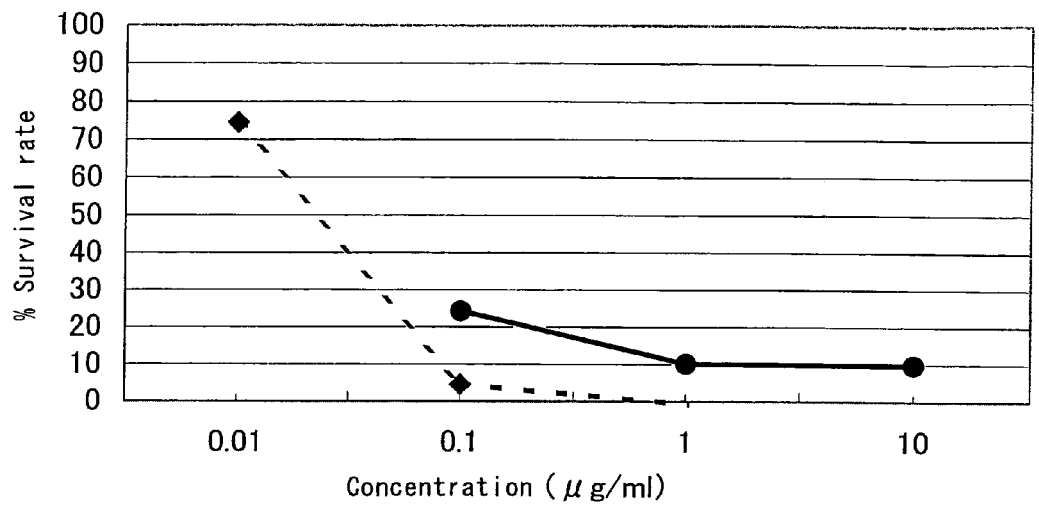
FIG. 5g shows a graph depicting the cell-death-inducing activity of purified human anti-TRAIL-R2 monoclonal antibodies (0304) on Colo205 and normal human hepatocytes. A solid line with solid circles (-●-) represents normal human hepatocyte, and a dotted line with solid diamond-shaped symbols (--□--) represents Colo205 cells.
Figure 5H:
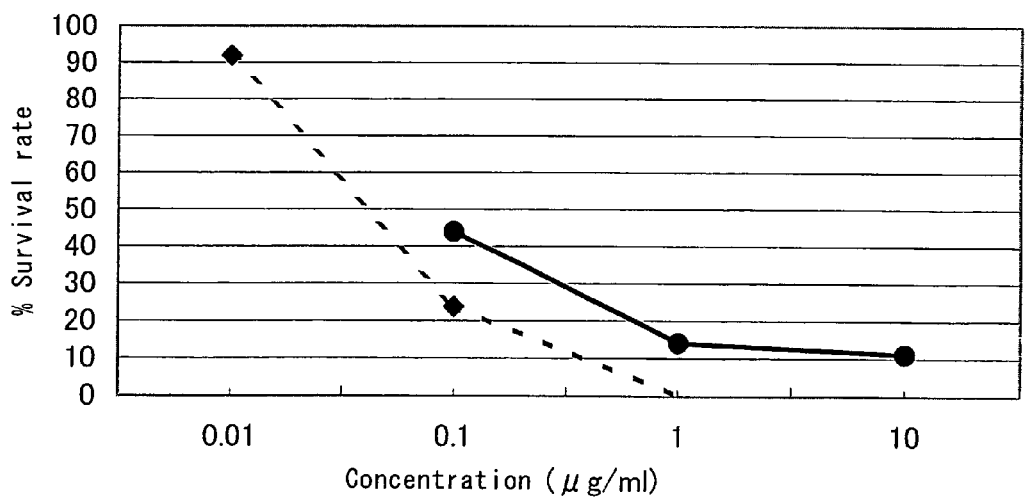
FIG. 5h shows a graph depicting the cell-death-inducing activity of purified human anti-TRAIL-R2 monoclonal antibodies (0322) on Colo205 and normal human hepatocytes. A solid line with solid circles (-●-) represents normal human hepatocyte, and a dotted line with solid diamond-shaped symbols (--□--) represents Colo205 cells.

FIG. 4 shows the result. The human anti-TRAIL-R2 monoclonal antibody and the negative control showed almost the same result, revealing that the human anti-TRAIL-R2 monoclonal antibody does not show cytotoxicity against HUVEC cells.

Example 9

Cell-Death-Inducing Activity on Normal Human Hepatocytes

Cell-death-inducing activity on normal human hepatocytes (hereinafter referred to as "HH cells") (Tissue Transformation Technologies) was measured using the culture supernatant of the hybridomas producing the human anti-TRAIL-R1 and R2 monoclonal antibodies obtained in Examples 4 to 6. First, frozen HH cells were thawed at 37° C., and then prepared at a concentration of $7.5 \times 10^5$/ml using a CM5300 medium (CEDRA). 100 µl of the suspension was added to each well of a 96-well flat-bottomed plate coated with collagen type I (Beckton Dickinson). After 4.5 hours of culturing at 37° C. under 5.0% carbon dioxide gas, medium exchange was performed. After 24 hours of culturing at 37° C. under 5.0% carbon dioxide gas, medium exchange was performed again. Subsequently, the culture supernatant of the hybridoma was added at 50 µl/well, and then 10 µl of goat anti-human IgG(γ)-specific polyclonal antibodies (Sigma) were added to each well at a final concentration of 5 µg/ml. Human IgG (Biogenesis) was used as a negative control. After 24 hours of culturing at 37° C. under 5.0% carbon dioxide gas, morphological changes in HH cells were observed under a microscope. The result of the human anti-TRAIL-R2 monoclonal antibody and that of negative control were almost the same, revealing that the human anti-TRAIL-R2 monoclonal antibody does not show cytotoxicity also against HH cells.

Example 10

Preparation of Each Antibody

The human anti-TRAIL-R1 and R2 monoclonal antibodies from the culture supernatant of the hybridomas obtained from Examples 4, 6 and 7 were purified by the following method. The culture supernatant containing the human anti-TRAIL-R1 and R2 monoclonal antibodies was subjected to affinity purification using rmp Protein A (Amersham Pharmacia Biotech), a 0.8×40 cm column (Bio-Rad), PBS as an adsorption buffer and a 0.02 M glycine buffer (pH 3) as an elution buffer. The eluted fraction was adjusted to have a pH of around 7.2 by adding 1 M Tris (pH 9.0). The thus prepared antibody solution was substituted with PBS using a dialysis membrane (10000 cut, Spectrum Laboratories), and then filtered using a MILLEX-GV membrane filter (Millipore) with a pore size of 0.22 µm for sterilization, thereby obtaining purified human anti-TRAIL-R1 and R2 monoclonal antibodies. Absorbance at 280 nm was measured, and then the concentration of the purified antibodies was calculated using 1.4 OD=1 mg/ml.

The culture supernatant containing the human anti-TRAIL-R1 and R2 monoclonal antibodies was prepared by the following method. First, human anti-TRAIL-R1 and R2 monoclonal antibodies-producing hybridomas were adapted in an eRDF medium (Kyokutoseiyaku) containing 10 ng/ml Recombinant Human IL-6 (R&D Systems) and 10% Low IgG fetal bovine serum (HyClone). The adapted hybridomas were cryopreserved. Next, for the purpose of antibody purification, a part of the hybridomas was adapted in an eRDF medium (Kyokutoseiyaku) containing bovine insulin (5 µg/ml, Gibco BRL), human transferrin (5 µg/ml, Gibco BRL), ethanolamine (0.01 mM, Sigma), sodium selenite ($2.5 \times 10^5$ mM, Sigma), 10 ng/ml recombinant human IL-6 (R&D Systems) and 1% Low IgG fetal bovine serum (HyClone). The hybridoma cells were cultured in flasks, and when the viable cell ratio of the hybridoma reached 90%, the culture supernatant was collected. The collected supernatant was applied to a 10 µm filter and a 0.2 µm filter (German Science), thereby removing miscellaneous waste materials such as hybridomas.

Example 11

Cell-Death-Inducing Activity of Purified Human Anti-TRAIL-R2 Monoclonal Antibody on Carcinoma Cells and Normal Human Hepatocytes The cell-death-inducing activity on the colon carcinoma cell Colo205 (ATCC No. CCL-222) was measured using the purified human anti-TRAIL-R2 monoclonal antibodies obtained in Example 10. Colo205 cells cultured in RPMI media containing 10% FCS were prepared at a concentration of $2.5 \times 10^4$/ml, and then the 100 µl of the suspension was added to each well of a 96-well flat-bottomed plate (Beckton Dickinson). After 24 hours of culturing at 37° C. under 5.0% carbon dioxide gas, the purified antibodies were added (10 µL/well) at final concentrations of 10, 100 and 1000 ng/ml. Further, 10 µl of goat anti-human IgG (γ)-specific polyclonal antibodies (Sigma) were added to each well at a final concentration of 10 µg/ml. For a part of the obtained hybridomas, wells not supplemented with goat anti-human IgG (γ)-specific polyclonal antibodies were prepared. As a positive control, human recombinant TRAIL proteins (R&D SYSTEMS) with final concentrations of 0.1, 1 and 10 ng/ml were used. A human anti-HSA antibody was used as a negative control. Culturing was performed at 37° C. under 5.0% carbon dioxide gas for 48 hours, so as to cause the antibodies to react with the receptors on the cell surfaces. The volume per reaction system was 120 µl. In addition, for 0304 and KMTR1, an experiment wherein no goat anti-human IgG (γ)-specific monoclonal antibodies were added as the cross-linker was conducted (described as "alone" in Table 5). The volume per reaction system in this case was 110 µl. After culturing, an MTS reagent (Cell Titer 96 AQ$_{UEOUS}$ Non-Radioactive Cell Proliferation Assay: Promega) was prepared according to the method described in the instructions. 20 µl of the reagent was added to each well. After 2 hours of culturing at 37° C. under 5.0% carbon dioxide gas, absorbance at a wavelength of 490 nm (with a reference wavelength of 630 nm) was measured using a microplate reader (1420 ARVO multi-label counter: WALLAC). Using the reducibility of the mitochondria as an indicator, the survival rate of the cells was calculated. The survival rate of the cells in each well was calculated using a formula similar to that of Example 7.

Next, the cell-death-inducing activity on HH cells (Tissue Transformation Technologies, and In Vitro Technologies) was measured using the human anti-TRAIL-R2 monoclonal antibodies obtained in Example 10. First the frozen HH cells were thawed at 37° C., and then prepared at a concentration of $7.5 \times 10^5$/ml using a CM5300 medium (CEDRA). 100 µl of the suspension was added to each well of a 96-well flat-bottomed plate coated with collagen type I (Beckton Dickinson). After 4.5 hours of culturing at 37° C. under 5.0% carbon dioxide gas, medium exchange was performed.

After another 24 hours of culturing at 37° C. under 5.0% carbon dioxide gas, the medium was exchanged with a serum-free medium [DMEM medium (Sigma) containing insulin (20 µg/ml, Sigma), glucagon (7 ng/ml, Sigma), hydrocortisone (7.5 µg/ml, Sigma) and human EGF (20 ng/ml, Beckton Dickinson)] or a CM5300 medium. Subsequently, the purified antibodies were added (10 µl/well) at final concentrations of 0.1, 1 and 10 µg/ml, and then 10 µl of goat-anti-human IgG(γ)-specific polyclonal antibodies (Sigma) were added to each well at final concentrations of 10 and 100 µg/ml. For a part of the obtained hybridomas, wells not supplemented with goat anti-human IgG(γ)-specific polyclonal antibodies were prepared. As a negative control, human anti-HSA antibodies were used. Culturing was performed at 37° C. under 5.0% carbon dioxide gas for 24 hours, the antibodies and the receptors on the cell surfaces were allowed to react. The volume per reaction system was 120 µl. In addition, for 0304 and KMTR1, an experiment wherein no goat anti-human IgG(γ)-specific monoclonal antibodies were added as the cross-linker was conducted (described as "alone" in Table 5). The volume per reaction system in this case was 110 µl. After culturing, HH cells were washed twice with PBS, 100 µl of PBS was added to each well, and then Triton X-100 was added (10 µl/well) at a final concentration of 0.8%. The cells were allowed to stand at 37° C. for 1 hour, so that living HH cells were lysed. The lysate was transferred (50 µl/well) to a different 96-well flat-bottomed plate, and then subjected to LDH assay. A reagent for LDH assay (CytoTox 96 Non-Radioactive Cytotoxicity Assay: Promega) was prepared according to the method described in the instructions, and then 50 µl of the reagent was added to each well. The plate was protected from light, and then it was allowed to stand at room temperature for 30 minutes. A reaction stop solution (1M acetic acid: Promega) was added at 50 µl/well. Absorbance at a wavelength of 492 nm was measured using a microplate reader (1420 ARVO multi-label counter: WALLAC). The survival rate of the cells was calculated using the enzymatic activity of LDH as an indicator. The survival rate of the cells of each well was calculated by a formula similar to that of Example 7.

Furthermore, LD50 values were calculated by the following method using the calculated survival rate. In the graph, the calculated survival rates at each antibody concentration are plotted on the vertical axis and the concentrations of the antibodies added to the cells are plotted on the horizontal axis. Plotted dots adjacent to each other are connected to make a curve. A formula expressing this curve was found by a regression calculation. The antibody concentrations corresponding to the survival rate of 50% were calculated using the formula, thereby obtaining LD50 values.

FIG. 5a to l and Table 5 show the results. In FIG. 5, a solid line with solid circles (-●-) represents normal human hepatocyte, and a dotted line with solid diamond-shaped symbols (--□--) represents Colo205 cells. Furthermore, FIGS. 5k and l show the results of experiments wherein no goat anti-human IgG(γ)-specific polyclonal antibodies were added. Table 5 shows the cell-death-inducing activity (LD50 value) of the purified human anti-TRAIL-R2 monoclonal antibody on colon carcinoma cells Colo205, and normal human hepatocytes. $2.5 \times 10^3$ colon carcinoma cells Colo205, were seeded in 100 µl of a medium per well of a 96-well flat-bottomed plate, and the purified human anti-TRAIL-R2 monoclonal antibodies were added to the cells on the next day. When the time for the reaction between the cells and the antibody reached 48 hours, the LD50 value was obtained. $7.5 \times 10^4$ normal cells (human hepatocytes) were seeded in 100 µl of a medium per well of a 96-well flat-bottomed plate, and the purified human anti-TRAIL-R2 monoclonal antibodies were added to normal cells (human hepatocytes) on the next day. When the time for the reaction between the cells and antibody reached to 24 hours, the LD50 value was obtained. Compared with the negative control, the purified human anti-TRAIL-R2 monoclonal antibody was shown to clearly have activity to induce cell death in Colo205 cells. Furthermore, compared with the human recombinant TRAIL and purified antibody H-48-2, the human hepatocyte toxicity of the purified human anti-TRAIL-R2 monoclonal antibodies E-11-13, L-30-10 and KMTR1 were shown to be low.

Moreover, KMTR1 was shown by the results of Example 4 to bind to both receptors, TRAIL-R1 and TRAIL-R2. It can be expected that this antibody can transduce cell-death-inducing signals via either TRAIL-R1 or TRAIL-R2 receptor.

Since the hepatocytes showed a survival rate of 50% or more even when 10 µg/ml L-30-10 was added, the LD50 of L-30-10 was 10 µg/ml or more. The LD50 was 24 µg/ml when regression calculation was performed based on a graph on which the antibody concentrations and the survival rates had been plotted. Since the hepatocytes showed a survival rate of 50% or less when 0.1 µg/ml F-4-8 was added, the LD50 of F-4-8 was 0.1 µg/ml or less. The LD50 was 0.002 µg/ml based on a regression calculation performed similarly to that for L-30-10. The LD50 values of KMTR1 and D1M were both confirmed to be 10 µg/ml or more. Further in a case where no goat anti-human IgG(γ)-specific polyclonal antibodies were added (hereinafter referred to as "in the "alone" case"), the survival rate of hepatocytes was never below 50%, even when KMTR1 with an antibody volume of 100 µg/ml was added. Thus, it was confirmed that the LD50 in the "alone" case was 100 µg/ml or more.

Next, the ratio of the LD50 value for normal hepatocytes to that for Colo 205 (showing how many times the LD50 value for normal human hepatocytes is greater than that for Colo205 cells) was measured (N/C ratio). The results were N/C=25.45 (10 times or more greater) in the case of purified antibody E-11-3, N/C=67 or more (10 times or more greater) in the case of D1M, N/C=50 (10 times or more greater) in the case of 0304 alone, N/C=240 (100 times or more greater) in the case of L-30-10, and N/C=1000 times or more greater in the case of KMTR1 alone. Thus, all the antibodies were shown to be excellent in terms of efficacy and safety (Table 5).

TABLE 5

| Purified human anti-TRAIL-R2 antibody | Normal human hepatocyte LD50 (µg/ml) | Colo205 LD50 (µg/ml) | N/C ratio |
|---|---|---|---|
| E-11-13 | 2.8 | 0.11 | 25.45 |
| F-4-8 | 0.002 | 0.02 | 0.1 |
| H-48-2 | 0.12 | 0.15 | 0.8 |
| L-30-10 | 24 | 0.1 | 240 |
| W-40-5 | 7.47 | 0.7 | 10.7 |
| 0304 | 0.002 | 0.02 | 0.1 |
| 0322 | 0.06 | 0.04 | 1.5 |
| KMTR1 | >10 | 0.04 | >250 |
| D1M | >10 | 0.15 | >67 |
| 0304 (alone) | 1 | 0.02 | 50 |
| KMTR1 (alone) | >100 | 0.1 | >1000 |
| Human recombinant TRAIL | 0.25 ng/ml | 2 ng/ml | 0.125 |

By a similar method, the cell-death-inducing activity of the purified human anti-TRAIL-R2 monoclonal antibodies was examined for U251 cells (derived from glioma, Riken Genebank No. RCB0461) and Jurkat cells (derived from T cell lymphomas, Dainippon Pharmaceutical Co., Ltd.). In an experiment for U251 cells, $1.0 \times 10^4$ cells were seeded in 100 µl of a medium per well of a 96-well flat-bottomed plate and then cultured at 37° C. in the presence of 5% $CO_2$. The antibodies were added on the next day. After culturing under the above environment for 48 hours, the survival rate of the cells was measured. In an experiment for Jurkat cells, $4.0 \times 10^4$ cells were seeded in 100 µl of a medium per well of a 96-well flat-bottomed plate, and then the antibodies were added. After 48 hours of culturing at 37° C. in the presence of 5% $CO_2$, the survival rate of the cells was measured. The LD50 value (unit: µg/ml) of each antibody is as shown below.

LD50 of E-11-13 for U251 cells: 0.3, and for Jurkat cells: 0.1.

LD50 of L-30-10 for U251 cells: 0.17, and for Jurkat cells: 0.13.

LD50 of H-48-2 for U251 cells: 0.24, and for Jurkat cells: 0.07.

LD50 of F-4-8 for U251 cells: 0.03, and for Jurkat cells: 0.004.

LD50 of W-40-5 for U251 cells: 1.0, and for Jurkat cells: 0.48.

In addition for U251 cells, assay was performed with a system wherein a cisplatin solution (NIPPON KAYAKU) with a final concentration of 4 µg/ml was added simultaneously with the antibody.

Example 12

Effect of Purified Human Anti-TRAIL-R2 Monoclonal Antibodies on Tumor-Bearing Mice The effect of the human anti-TRAIL-R2 monoclonal antibody obtained in Example 10 was examined using a tumor-bearing mouse model according to the following method.

Colo205, colon carcinoma cells, were subcutaneously transplanted in the dorsal areas at $5 \times 10^6$/mouse to 4- to 6-week-old Balb/c nude mice (purchased from CLEA Japan). 1 week to 10 days after transplantation, the sizes of tumors that had adhered were measured. 5 or 7 tumor-bearing mice having average tumor sizes of approximately 100 mm$^3$ or 300 mm$^3$ were grouped into a single group. Into the peritoneal cavities of the tumor-bearing mice, the purified antibodies were administered at 1, 4, 20, 25 and 100 µg/mouse (dissolved in 200 µl of PBS), and then the tumor size was measured. The same volume of human anti-HSA antibodies was used as a negative control of the antibody.

Figure 6:
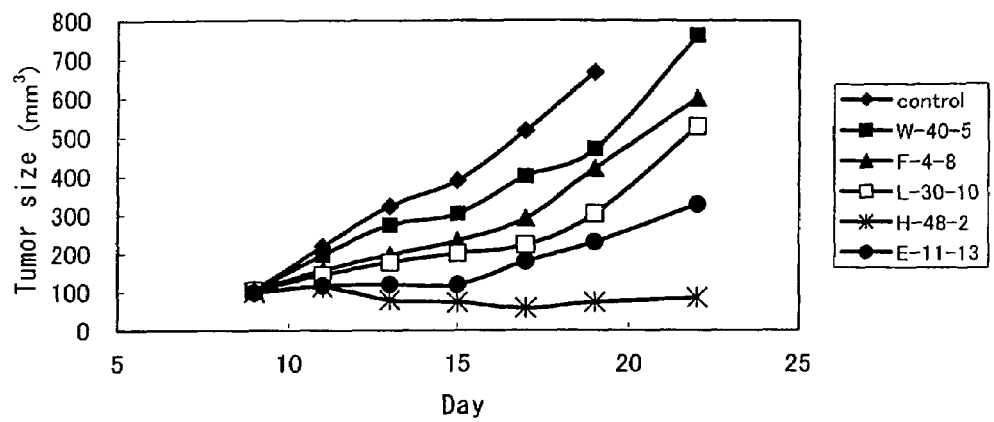
FIG. 6 shows the results of measuring the tumor size when purified human anti-TRAIL-R2 monoclonal antibodies E-11-13, F-4-8, H-48-2, L-30-10 and W-40-5 were administered at 1 μg/mouse three times on alternate days.

FIGS. 6 to 10 show the results of the above experiments. In the groups where purified human anti-TRAIL-R2 monoclonal antibodies E-11-13, F-4-8, H-48-2, L-30-10 and W-40-5 had been administered at 1 µg/mouse, a regression effect was observed in the group to which H-48-2 had been administered. The anti-tumor effects were lower in descending order of E-11-13, L-30-10, F-4-8 and W-40-5 (FIG. 6). In FIG. 6, when the antibody was administered 3 times on alternate days, growth suppression and a regression effect were observed at least for 13 days when calculated from the initial administration (H-48-2 clone).

Figure 7:
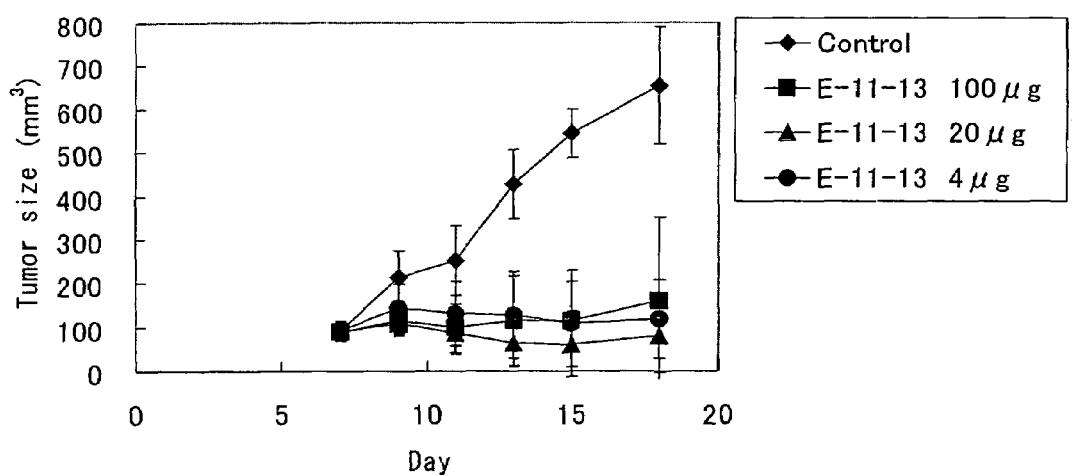
FIG. 7 shows the results of measuring the tumor size when purified human anti-TRAIL-R2 monoclonal antibodies E-11-13 were administered at 4, 20 and 100 μg/mouse 4 times.

In the groups to which E-11-13 had been administered at 4, 20 and 100 µg/mouse, anti-tumor effects were confirmed in all the mice. With a dose of 20 µg/mouse, the highest tumor regression effect was observed (FIG. 7). In FIG. 7, when the antibody was administered 4 times on alternate days, growth suppression and a regression effect were observed at least for 11 days when calculated from the initial administration. Changes with time in tumor volume of the group to which the antibodies were administered at 20 µg/mouse 4 times on alternate days (administered on days 7, 9, 11 and 13 after transplantation) were as follows.

On day 2 after the initial administration (corresponding to day 9 in FIG. 7), the average tumor volume was 109.5 mm$^3$;

On day 4 after the initial administration (corresponding to day 11 in FIG. 7), the average tumor volume was 85.1 mm$^3$:

On day 6 after the initial administration (corresponding to day 13 in FIG. 7), the average tumor volume was 64.3 mm$^3$:

On day 8 after the initial administration (corresponding to day 15 in FIG. 7), the average tumor volume was 61.8 mm$^3$; and On day 11 after the initial administration (corresponding to day 18 in FIG. 7), the average tumor volume was 78.9 mm$^3$.

The tumor volume on day 4 after the start of administration was approximately 85.1 mm$^3$, and a 14% or more tumor reduction was observed. This reduction was maintained on day 11 after the administration, showing that the antibody of the present invention possesses a high anti-tumor effect.

Figure 8:
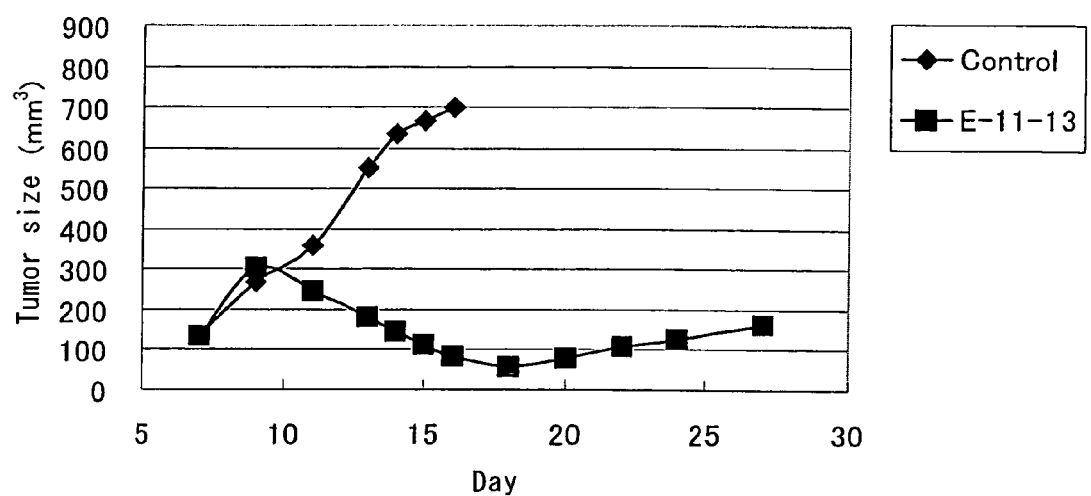
FIG. 8 shows the results of measuring the tumor size when purified human anti-TRAIL-R2 monoclonal antibodies E-11-13 were administered at 20 μg/300 mm$^3$ tumor-bearing mouse three times on alternate days.

E-11-3 was administered at 20 µg/mouse to a group of 7 tumor-bearing mice where the tumors were approximately 300 mm$^3$ on average. As a result, significant tumor regression was observed (FIG. 8). In FIG. 8, when the antibody was administered 3 times on alternate days, growth suppression and a regression effect were observed at least for 18 days when calculated from the initial administration. Changes with time in tumor volume of the group to which the antibodies were administered at 20 µg/mouse 3 times on alternate days (administered on days 9, 11 and 13 after transplantation) are as follows.

On day 2 after the initial administration (corresponding to day 11 in FIG. 8), the average tumor volume was 246.9 mm$^3$;

On day 4 after the initial administration (corresponding to day 13 in FIG. 8), the average tumor volume was 181.8 mm$^3$;

On day 5 after the initial administration (corresponding to day 14 in FIG. 8), the average tumor volume was 146.2 mm$^3$;

On day 6 after the initial administration (corresponding to day 15 in FIG. 8), the average tumor volume was 110.8 mm$^3$;

On day 7 after the initial administration (corresponding to day 16 in FIG. 8), the average tumor volume was 82.7 mm$^3$;

On day 9 after the initial administration (corresponding to day 18 in FIG. 8), the average tumor volume was 57.5 mm$^3$;

On day 11 after the initial administration (corresponding to day 20 in FIG. 8), the average tumor volume was 81.3 mm$^3$;

On day 13 after the initial administration (corresponding to day 22 in FIG. 8), the average tumor volume was 108.1 mm$^3$;

On day 15 after the initial administration (corresponding to day 24 in FIG. 8), the average tumor volume was 127.8 mm$^3$; and On day 18 after the initial administration (corresponding to day 27 in FIG. 8), the average tumor volume was 163.3 mm$^3$.

The tumor volume on day 4 after the start of administration was approximately 181.8 mm$^3$, and a 39% or more tumor reduction was observed. This reduction was maintained even on day 18 after the administration, showing that the antibody of the present invention possesses a high anti-tumor effect.

Figure 9:
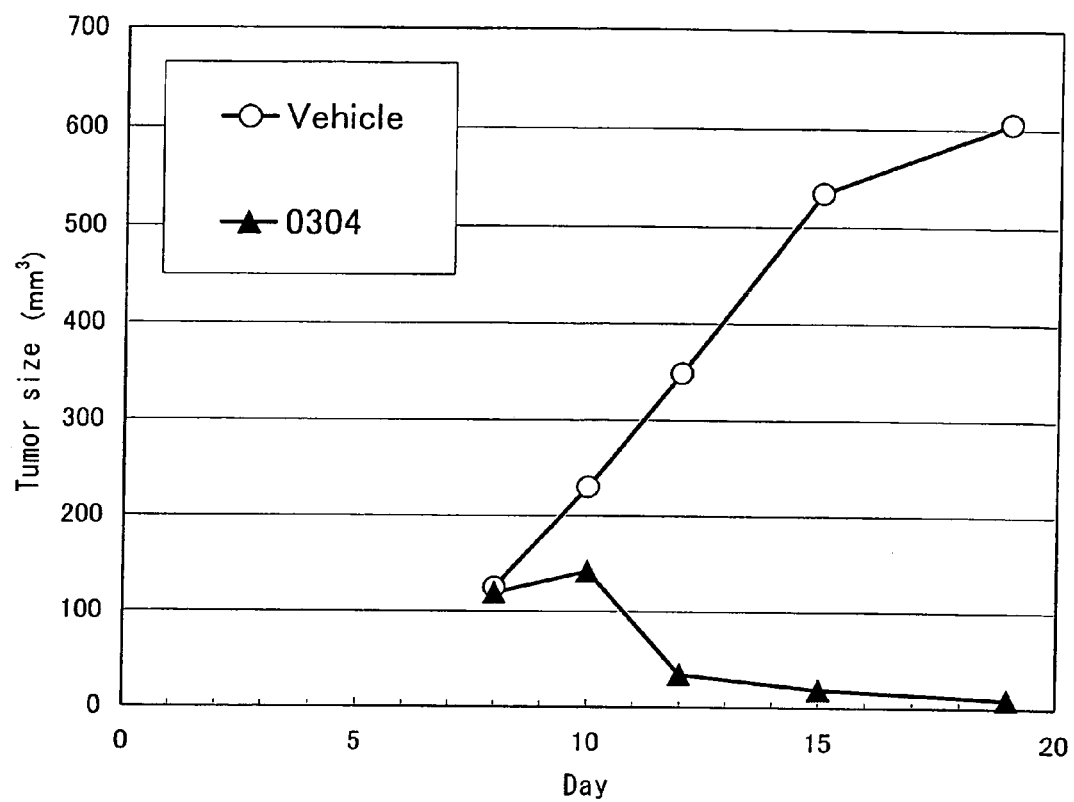
FIG. 9 shows the results of measuring the tumor size when purified human anti-TRAIL-R2 monoclonal antibodies 0304 were administered at 20 μg/100 mm$^3$ tumor-bearing mouse three times on alternate days.

The activity of 0304 antibody was evaluated as follows. Colo205, colon carcinoma cells, were subcutaneously transplanted in the dorsal areas at 5×10⁶/mouse to 6-week-old Balb/c nude mice (purchased from CLEA Japan). 8 days after transplantation, the sizes of tumors that had adhered were measured. 5 tumor-bearing mice having an average tumor size of approximately 100 mm³ were grouped into a single group. Into the peritoneal cavities of the tumor-bearing mice, the purified antibodies were administered at 20 μg/mouse (dissolved in 200 μl of PBS), and then the tumor size was measured. Anti-tumor effects were confirmed in all the mice of the group, to which 0304 had been administered (at 20 μg/mouse) 3 times on alternate days (administered on days 8, 10 and 12 after transplantation) (FIG. 9). Changes with time in tumor volume are as follows.

On day 2 after the initial administration (corresponding to day 10 in FIG. 9), the average tumor volume was 142.092 mm³;

On day 4 after the initial administration (corresponding to day 12 in FIG. 9), the average tumor volume was 34.138 mm³;

On day 7 after the initial administration (corresponding to day 15 in FIG. 9), the average tumor volume was 18.641 mm³; and On day 11 after the initial administration (corresponding to day 19 in FIG. 9), the average tumor volume was 9.339 mm³;

The tumor volume on day 4 after the start of administration was approximately 34.138 mm³, and a 65% or more tumor reduction was observed. This reduction was maintained even on day 11 after the administration, showing that the antibody of the present invention possesses an extremely high anti-tumor effect.

Figure 10:
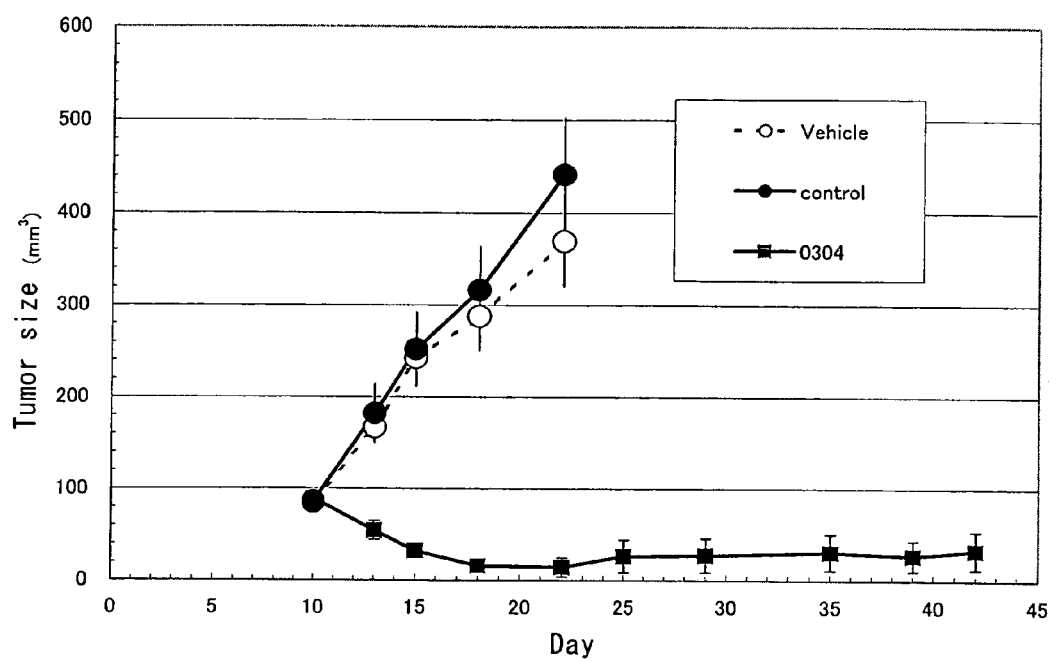
FIG. 10 shows the results of measuring the tumor size when purified human anti-TRAIL-R2 monoclonal antibodies 0304 were administered at 25 μg/100 mm$^3$ tumor-bearing mouse three times.

Next, Colo205, colon carcinoma cells, were subcutaneously transplanted in the dorsal areas at 5×10⁶/mouse to 12-week-old Balb/c nude mice (purchased from CLEA Japan). 10 days after transplantation, the sizes of tumors that had adhered were measured. 5 tumor-bearing mice having an average tumor size of approximately 100 mm³ were grouped into a single group. Into the peritoneal cavities of the tumor-bearing mice, the purified antibodies were administered at 25 μg/mouse (dissolved in 200 μl of PBS), and then the tumor size was measured. As a negative control of the antibody, the same volume of human anti-HSA antibodies was used. Anti-tumor effects were confirmed in all the mice of the group, to which 0304 had been administered at 25 μg/mouse 3 times (administered on days 10, 13 and 15 after transplantation) (FIG. 10). Changes with time in tumor volume are as follows.

On day 3 after the initial administration (corresponding to day 13 in FIG. 10), the average tumor volume was 54.626 mm³;

On day 5 after the initial administration (corresponding to day 15 in FIG. 10), the average tumor volume was 32.357 mm³;

On day 8 after the initial administration (corresponding to day 18 in FIG. 10), the average tumor volume was 15.895 mm³;

On day 12 after the initial administration (corresponding to day 22 in FIG. 10), the average tumor volume was 14.377 mm³;

On day 15 after the initial administration (corresponding to day 25 in FIG. 10), the average tumor volume was 26.654 mm³;

On day 19 after the initial administration (corresponding to day 29 in FIG. 10), the average tumor volume was 27.565 mm³;

On day 25 after the initial administration (corresponding to day 35 in FIG. 10), the average tumor volume was 30.802 mm³;

On day 29 after the initial administration (corresponding to day 39 in FIG. 10), the average tumor volume was 27.092 mm³; and On day 32 after the initial administration (corresponding to day 42 in FIG. 10), the average tumor volume was 32.921 mm³.

On day 12 after the initial administration (corresponding to day 22 in FIG. 10), tumor disappearance was confirmed in 3 out of 5 mice.

The average tumor volume on day 3 after the initial administration was 54.626 mm³, and a 45% or more tumor reduction was observed. Moreover, the average tumor volume on day 5 after the administration was 32.357 mm³, and a 65% or more tumor reduction was observed. This reduction was maintained on day 32 after the administration. Specifically, the 65% or more reduction was maintained at least for 27 days. Thus, it was shown that the antibody of the present invention possesses an extremely high anti-tumor effect.

Furthermore, in FIG. 10, growth suppression and a regression effect were observed for at least 32 days when calculated from the initial administration.

In addition, in FIGS. 9 and 10, "Vehicle" represents PBS (200 μl) that was used as a medium for dissolving the antibodies upon administration.

As shown in Example 11, 0304 or KMTR1 antibodies alone can show cell-death-inducing activity. Moreover, as shown in this example, 0304 was confirmed to have a significant anti-tumor effect in the tumor-bearing mouse model. Hence, antibodies that can alone show cell-death-inducing activity and anti-tumor activity are expected to be able to show anti-tumor activity without depending on the physiological conditions (e.g., types or numbers of immunocytes) of a patient to which a prophylactic or therapeutic agent against disease caused by TRAIL-R1 and/or TRAIL-R2-expressing cells is to be administered, particular when a therapeutic agent against malignant tumor is to be administered.

Example 13

Binding Affinity of Purified Human Anti-TRAIL-R1 and TRAIL-R2 Monoclonal Antibodies to TRAIL-R1 and TRAIL-R2

The binding affinity of purified human anti-TRAIL-R monoclonal antibodies obtained in Example 10 to TRAIL-R was studied by the following method using BIACORE 2000 (Biacore).

1) Immobilization of TRAIL-R1-hFc and TRAIL-R2-hFc

TRAIL-R1-hFc or TRAIL-R2-hFc was diluted at a final concentration of 10 μg/ml with 10 mM Acetic Acid (pH 4.0), and then immobilized on a sensor chip CM5 by the amine coupling method. The immobilization conditions are as follows. NHS activation and ethanolamine blocking were performed according to the methods described in the instructions. Coupling of TRAIL-R1-hFc and that of TRAIL-R2-hFc were performed by manual injection as described in the instructions.

(Immobilization conditions) Flow rate: 5 μl/minute

NHS activation: 7 minutes

Coupling: manual injection

Ethanolamine blocking: 7 minutes

It was confirmed that 377.4 RU of TRAIL-R1-hFc and 495.4RU of TRAIL-R2-hFc were immobilized on the sensor chip under the above conditions.

2) Regeneration Conditions and Confirmation of Reproducibility

20 μg/ml purified human anti-TRAIL-R1 monoclonal antibody 2–6 was added for 2 minutes onto the sensor chip on which TRAIL-R1-hFc had been immobilized. And then, the binding of the antibodies to TRAIL-R1-hFc was confirmed. Subsequently, 50 mM NaOH was added for 15 seconds, and then the complete dissociation of the bound antibodies from TRAIL-R1-hFc was confirmed (hereinafter complete dissociation is referred to as "regeneration"). Next, the purified human anti-TRAIL-R1 monoclonal antibody 2–6 was added to the regenerated TRAIL-R1-hFc at a flow rate of 20 μl/minute by the KINJECT method (binding for 1 minute and dissociation for 1 minute), followed by the addition of 50 mM NaOH for 15 seconds to regenerate TRAIL-R1 hFc. This cycle was repeated 9 times. Even after 9 repetitions of the above cycle, no change was found in the amount of TRAIL-R1-hFc immobilized on the sensor chip or the amount of the antibody bound thereon. It was thus revealed that TRAIL-R1-hFc was regenerated without being inactivated by the addition of 50 mM NaOH for 15 seconds. A similar examination was performed using a sensor chip with TRAIL-R2-hFc immobilized thereto and 20 μg/ml purified human anti-TRAIL-R2 monoclonal antibody E-11-13. As a result, it was confirmed that TRAIL-R2-hFc can be regenerated under the same regeneration conditions.

3) Examination of Interaction

Each of the purified human anti-TRAIL-R1 monoclonal antibodies 1-13, 2-6 and 2-12 was serially diluted to 2.1, 4.2, 8.4, 16.8, 33.5, 67.0 and 134.0 nM using HBS-EP (Biacore). Each antibody of the dilution series was added in order at a flow rate of 20 μl/minute by the KINJECT method (binding for 2 minutes and dissociation for 6 minutes), thereby obtaining a sensorgram. Similarly, each of the purified human anti-TRAIL-R2 monoclonal antibodies E-11-13, L-30-10, H-48-2, F-4-8, W-40-6 and X-14-4 was serially diluted to 0.52, 1.05, 2.1, 2.09, 4.19 and 8.38 nM using HBS-EP (Biacore). Each antibody of the dilution series was added in order at a flow rate of 20 μl/minute by the KINJECT method (binding for 2 minutes and dissociation for 2 minutes), thereby obtaining sensorgrams. For each antibody, kinetics analysis was performed using each sensorgram and BIAevaluation software ver3.2 (Biacore). As a fitting model, global fitting was performed using a Bivalent model, so that the binding rate constant and the dissociation rate constant were found. In addition, a dissociation constant (Kd value) was calculated from the two constants. Also, the sensorgrams were used for fitting after the subtraction of control cells and buffer correction. Table 6 and Table 7 show the results. In the tables, "kass" indicates the binding rate constant, "kdiss" indicates the dissociation rate constant, and "$K_D$" indicates the dissociation constant.

TABLE 6

| Purified human anti-TRAIL-R1 antibody | kass (1/Ms) | kdiss (1/s) | $K_D$ (nM) |
|---|---|---|---|
| 1-13 | $1.08 \times 10^5$ | $4.58 \times 10^{-4}$ | 4.24 |
| 2-6 | $1.62 \times 10^5$ | $1.86 \times 10^{-4}$ | 1.15 |
| 2-12 | $1.63 \times 10^5$ | $7.80 \times 10^{-4}$ | 4.79 |

TABLE 7

| Purified human anti-TRAIL-R2 antibody | kass (1/Ms) | kdiss (1/s) | $K_D$ (nM) |
|---|---|---|---|
| E-11-13 | $5.27 \times 10^5$ | $3.84 \times 10^{-5}$ | 0.0729 |
| L-30-10 | $6.13 \times 10^5$ | $1.44 \times 10^{-3}$ | 2.35 |
| H-48-2 | $5.75 \times 10^5$ | $1.58 \times 10^{-3}$ | 2.75 |
| F-4-8 | $5.63 \times 10^5$ | $7.05 \times 10^{-4}$ | 1.25 |
| W-40-6 | $1.74 \times 10^5$ | $2.92 \times 10^{-3}$ | 16.8 |
| X-14-4 | $6.55 \times 10^4$ | $2.93 \times 10^{-3}$ | 44.7 |

Example 14

Preparation of Genes Encoding Monoclonal Antibodies and Construction of Recombinant Antibody Expression Vectors (1) cDNA Cloning and Construction of Expression Vectors of E-11-13, L-30-10 and H-48-2 Antibody Genes Hybridomas E-11-13, L-30-10 and H-48-2 were cultured in eRDF media (Kyokutoseiyaku) containing 10 ng/ml Recombinant Human IL-6 (R&D Systems) and 10% Low IgG Fetal Bovine Serum (HyClone). After the cells were collected by centrifugation, TRIZOL (Gibco BRL) was added, and then total RNA was extracted according to the instructions. Cloning of the variable regions of the antibody cDNAs was performed using a SMART RACE cDNA amplification Kit (Clontech) according to the attached instructions. Using 5 μg of total RNA as a template, 1st strand cDNA was prepared.

1) Synthesis of 1st Strand cDNA
   Total RNA 5 μg/3 μl
   5'CDS 1 μl
   SMART oligo 1 μl
After the reaction solution having the above composition was incubated at 70° C. for 2 minutes,
   5×Buffer 2 μl
   DTT 1 μl
   DNTP mix 1 μl and
   Superscript II 1 μl
were added, followed by incubation at 42° C. for 1.5 hours.

Furthermore, after 100 μl of Tricine buffer was added, incubation was performed at 72° C. for 7 minutes, thereby obtaining 1 st strand cDNA.

2) Amplification by PCR of Heavy Chain Genes and Light Chain Genes, and Construction of Recombinant Antibody Expression Vector.

For cDNA amplification, Z-Taq (Takara) was used.
   cDNA 2 μl
   10×Z-Taq Buffer 5 μl
   dNTP mix 4 μl
   Z-Taq 1 μl
   Primer 1
   Primer 2

A reaction solution having the above composition was prepared to have a final volume of 50 μl with double distilled water, and then subjected to PCR.

To amplify heavy chains, UMP (SMART RACE cDNA amplification Kit; Clontech) and hh-6 primer (5'-GGT CCG GGA GAT CAT GAG GGT GTC CTT-3') (SEQ ID NO: 7) were used, and a cycle of 98° C. for 1 second and 68° C. for 30 seconds was repeated 30 times. Furthermore, using 1 μl of the reaction solution as a template, NUMP (SMART RACE cDNA amplification Kit; Clontech) and hh-3 primer (5'-GTG CAC GCC GCT GGT CAG GGC GCC TG-3') (SEQ ID NO: 8), a cycle of 98° C. for 1 second and 68° C. for 30 seconds was repeated 20 times. Subsequently, the amplified PCR product was purified using a PCR purification kit (QIAGEN), and then the nucleotide sequences were determined using hh-4 (5'-GGT GCC AGG GGG AAG ACC GAT GG-3') (SEQ ID NO: 9) as a primer. Based on the sequence information, it was found that the 3 clones of E-11-13, L-30-10 and H-48-2 were identical in the sequence of the N-terminal region. Thus, common primers were used for subcloning and the determination of the nucleotide sequences. Based on the sequence information, tnH48KBgl (5'-ATA TAG ATC TCT CAG TTA GGA CCC AGA GGG AAC C-3') (SEQ ID NO: 10) was synthesized. Using this primer, the sequences were also determined from the opposite direction. PCR was performed using a specific primer and tnCHNhe (5'-GAT GGG CCC TTG GTG CTA GCT GAG GAG ACG G-3') (SEQ ID NO: 11) (98° C. for 1 second, 60° C. for 30 seconds and 72° C. for 30 seconds). The amplified heavy chain cDNA fragment was digested with Sal I and Nhe I, and then introduced into an N5KG1-Val Lark vector (an altered vector of IDEC Pharmaceuticals, N5KG1 (U.S. Pat. No. 6,001,358)) that had been cleaved using the same enzymes. Sequencing was performed using the vector as a template so that the inserted sequence was confirmed to be identical to the sequence determined by a direct sequence.

Light chains were amplified by repeating a cycle of 98° C. for 1 second and 68° C. for 30 seconds 30 times using UMP (SMART RACE cDNA amplification Kit; Clontech) and hk-2 primer (5'-GTT GAA GCT CTT TGT GAC GGG CGA GC-3') (SEQ ID NO: 12). Furthermore, using 1 μl of the reaction solution as a template, NUMP (SMART RACE cDNA amplification Kit; Clontech) and hk-6 (5'-T GGC GGG AAG ATG AAG ACA GAT GGT G-3') (SEQ ID NO: 13), a cycle of 98° C. for 1 second and 68° C. for 30 seconds was repeated 20 times. Subsequently, the amplified PCR product was purified using a PCR purification kit (QIAGEN), and then the nucleotide sequences were determined using hk-6 (5'-tggc ggg aag atg aag aca gat ggt g-3') primer. Based on the sequence information, it was found that 3 clones were all identical in the sequence of the N-terminal region. Thus, common primers were used for subcloning. Based on the sequence information, tnH48Hsal (5'-ATA TGT CGA CTA CGG GGG GGC TTT CTG AGA GTC-3') (SEQ ID NO: 14) was synthesized. Using this primer, sequencing was also performed from the opposite direction. PCR was performed using a specific primer and tnCkBsi (5'-AAG ACA GAT GGT GCA GCC ACC GTA CGT TTG AT-3') (SEQ ID NO: 15) (98° C. for 1 second, 60° C. for 30 seconds and 72° C. for 30 seconds). The amplified light chain cDNA fragment was digested with Bgl II and BsiW I, and then introduced into a N5KG1-Val Lark vector that had been cleaved with the same enzymes. Sequencing was performed using the vector as a template so that the inserted sequence was confirmed to be identical to the sequence determined by a direct sequence.

DNAs encoding the E-11-13 heavy chain variable region and light chain variable region, and the amino acid sequences comprising the heavy chain variable region and the light chain variable region, are as respectively shown below.

```
<E-11-13 heavy chain comprising the variable region>
(SEQ ID NO: 16)

GTCGACTACGGGGGGCTTTCTGAGAGTCATGGATCTCATGTGCAAGAA

AATGAAGCACCTGTGGTTCTTCCTCCTGCTGGTGGCGGCTCCCAGATGG

GTCCTGTCCCAGCTGCAGCTGCAGGAGTCGGGCCCAGGACTGGTGAAG

CCTTCGGAGACCCTGTCCCTCACCTGCACTGTCTCTGGTGGCTCCATCAT

CAGTAAAAGTTCCTACTGGGGCTGGATCCGCCAGCCCCCAGGGAAGGG

GCTGGAGTGGATTGGGAGTATCTATTATAGTGGGAGTACCTTCTACAACC

CGTCCCTCAAGAGTCGAGTCACCATATCCGTAGACACGTCCAAGAACCA

GTTCTCCCTGAAGCTGAGCTCTGTGACCGCCGCAGACACGGCTGTGTAT

TACTGTGCGAGACTGACAGTGGCTGAGTTTGACTACTGGGGCCAGGGA

ACCCTGGTCACCGTCTCCTCAGCTAGC

<E-11-13 heavy chain comprising the variable region>
(SEQ ID NO: 17)

MDLMCKKMKHLWFFLLLVAAPRWVLSQLQLQESGPGLVKPSETLSLTCTV

SGGSIISKSSYWGWIRQPPGKGLEWIGSIYYSGSTFYNPSLKSRVTISVDTSK
```

```
-continued
NQFSLKLSSVTAADTAVYYCARLTVAEFDYWGQGTLVTVSSAS

<E-11-13 light chain comprising the variable region>
(SEQ ID NO: 18)

TCACAGATCTCTCAGTTAGGACCCAGAGGGAACCATGGAAGCCCCAGC

TCAGCTTCTCTTCCTCCTGCTACTCTGGCTCCCAGATACCACCGGAGAA

ATTGTGTTGACACAGTCTCCAGCCACCCTGTCTTTGTCTCCAGGGGAAA

GAGCCACCCTCTCCTGCAGGGCCAGTCAGAGTGTTAGCAGCTTCTTAGC

CTGGTACCAACAGAAACCTGGCCAGGCTCCCAGGCTCCTCATCTATGAT

GCATCCAACAGGGCCACTGGCATCCCAGCCAGGTTCAGTGGCAGTGGG

TCTGGGACAGACTTCACTCTCACCATCAGCAGCCTAGAGCCTGAAGATT

TTGCAGTTTATTACTGTCAGCAGCGTAGCAACTGGCCTCTCACTTTCGGC

CCTGGGACCAAAGTGGATATCAAACGTACG

<E-11-13 light chain comprising the variable region>
(SEQ ID NO: 19)

MEAPAQLLFLLLLWLPDTTGEIVLTQSPATLSLSPGERATLSCRASQSVSSFL

AWYQQKPGQAPRLLIYDASNRATGIPARFSGSGSGTDFTLTISSLEPEDFAV

YYCQQRSNWPLTFGPGTKVDIKRT
```

The translation initiation point of the heavy chain DNA is an ATG codon that begins from the 30th adenine (A) from the 5' end of SEQ ID NO: 16. The boundary of the antibody variable region and the constant region is located between the 461st adenine (A) and the 462nd guanine (G) from the 5' end. In the amino acid sequence, the heavy chain variable region ranges from the N-terminus to the 144th serine (S) residue of SEQ ID NO: 17, and the constant region is of the 145th alanine (A) and the following residues. Analysis of the N-terminus of the purified heavy chain protein revealed that the heavy chain signal sequence ranges from the N-terminus to the 26th serine (S) of SEQ ID NO: 17, and the N-terminus of the mature protein is the 27th glutamine (Q) of SEQ ID NO: 17.

The translation initiation point of the light chain DNA is an ATG codon that begins from the 35th A from the 5' end of SEQ ID NO: 18, and the variable region ranges from the 5' end to the 415th adenine (A). In the amino acid sequence, the variable region ranges from the N-terminus to the 127th lysine (K) of SEQ ID NO: 19. Analysis of the N-terminus of the purified light chain protein revealed that the light chain signal sequence ranges from the N-terminus to the 20th glycine (G) of SEQ ID NO: 19, and the N-terminus of the mature protein is the 21st glutamic acid (E) of SEQ ID NO: 19.

DNAs encoding the L-30-10 heavy chain variable region and light chain variable region, and the amino acid sequences comprising the heavy chain variable region and the light chain variable region, are as respectively shown below.

```
<L-30-10 heavy chain comprising the variable region>
(SEQ ID NO: 20)

GTCGACTACGGGGGGCTTTCTGAGAGTCATGGATCTCATGTGCAAGAA

AATGAAGCACCTGTGGTTCTTCCTCCTGCTGGTGGCGGCTCCCAGATGG

GTCCTGTCCCAGTTGCAGCTGCAGGAGTCGGGCCCAGGACTGGTGAAG

CCCTCGGAGACCCTGTCCCTCACCTGCACTGTCTCTGGTGGCTCCATCA

GCAGTAGGAGTAACTACTGGGGCTGGATCCGCCAGCCCCAGGGAAGG

GGCTGGAGTGGATTGGGAATGTCTATTATAGAGGGAGCACCTACTACAA

TTCGTCCCTCAAGAGTCGAGTCACCATATCCGTAGACACGTCCAAGAAC

CAGTTCTCCCTGAAGCTGAGCTCTGTGACCGTCGCAGACACGGCTGTGT

ATTACTGTGCGAGACTGTCAGTGGCTGAGTTTGACTACTGGGGCCAGGG

AATCCTGGTCACCGTCTCCTCAGCTAGC

<L-30-10 heavy chain comprising the variable region>
```

-continued (SEQ ID NO: 21)

MDLMCKKMKHLWFFLLLVAAPRWVLSQLQLQESGPGLVKPSETLSLTCTV

SGGSISSRSNYWGWIRQPPGKGLEWIGNVYYRGSTYYNSSLKSRVTISVDT

SKNQFSLKLSSVTVADTAVYYCARLSVAEFDYWGQGILVTVSSAS

<L-30-10 light chain comprising the variable region>
(SEQ ID NO: 22)

AGATCTCTCAGTTAGGACCCAGAGGGAACCATGGAAGCCCCAGCTCAG

CTTCTCTTCCTCCTGCTACTCTGGCTCCCAGATACCACCGGAGAAATTGT

GTTGACACAGTCTCCAGCCACCCTGTCTTTGTCTCCAGGGGAAAGAGC

CACCCTCTCTTGTAGGGCCAGTCAGAGTGTTAGCAGCTTCTTAGCCTGG

TACCAACAGAAACCTGGCCAGGCTCCCAGGCTCCTCATCTATGATGCAT

CCAACAGGGCCACTGGCAGCCCAGCCAGGTTCAGTGGCAGTGGGTCTG

GGACAGACTTCACTCTCACCATCAGCAGCCTAGAGCCTGAAGATTTTGC

AGTTTATTACTGTCAGCAGCGTAGCGACTGGCCTCTCACTTTCGGCCCT

GGGACCAAAGTGGATATCAAACGTACG

<L-30-10 light chain comprising the variable region>
(SEQ ID NO: 23)

MEAPAQLLFLLLLWLPDTTGEIVLTQSPATLSLSPGERATLSCRASQSVSSFL

AWYQQKPGQAPRLLIYDASNRATGSPARFSGSGSGTDFTLTISSLEPEDFAV

YYCQQRSDWPLTFGPGTKVDIKRT

The translation initiation point of the heavy chain DNA is an ATG codon that begins from the 30th adenine (A) from the 5' end of SEQ ID NO: 20. The boundary of the antibody variable region and the constant region is located between the 461st adenine (A) and the 462nd guanine (G) from the 5' end. In the amino acid sequence, the heavy chain variable region ranges from the N-terminus to the 144th serine (S) residue of SEQ ID NO: 21, and the constant region is of the 145th alanine (A) and the following residues. It was predicted by a gene sequence prediction software (Signal P ver.2) that the heavy chain signal sequence ranges from the N-terminus to the 26th serine (S) of SEQ ID NO: 21. Analysis of the N-terminus of the purified heavy chain protein revealed that the heavy chain signal sequence ranges from the N-terminus to the 26th serine (S) of SEQ ID NO: 21, and the N-terminus of the mature protein is the 27th glutamine (Q) of SEQ ID NO: 21.

The translation initiation point of the light chain DNA is an ATG codon that begins from the 31st A from the 5' end of SEQ ID NO: 22, and the variable region ranges from the 5' end to the 411st adenine (A). In the amino acid sequence, the variable region ranges from the N-terminus to the 127th lysine (K) of SEQ ID NO: 23. Analysis of the N-terminus of the purified light chain protein revealed that the light chain signal sequence ranges from the N-terminus to the 20th glycine (G) of SEQ ID NO: 23, and the N-terminus of the mature protein is the 21st glutamic acid (E) of SEQ ID NO: 23.

DNAs encoding the H-48-2 heavy chain variable region and light chain variable region, and the amino acid sequences comprising the heavy chain variable region and the light chain variable region, are as respectively shown below.

<H-48-2 heavy chain comprising the variable region>
(SEQ ID NO: 24)

TCGACTACGGGGGGCTTTCTGAGAGTCATGGATCTCATGTGCAAGAAA

ATGAAGCACCTGTGGTTCTTCCTCCTGCTGGTGGCGGCTCCCAGATGGG

TCCTGTCCCAGCTGCAGCTGCAGGAGTCGGGCCCAGGACTGGTGAAGC

CTTCGGAGACCCTGTCCCTCACCTGCACTGTCTCTGGTGGCTCCATCAG

CAGTAGTAGTTACTACTGGGGCTGGGTCCGCCAGCCCCCAGGGAAGGG

GCTGGAGTGGATTGGGAGTATCCATTATAGTGGGAGTACTTTCTACAACC

CGTCCCTCAAGAGTCGAGTCACCATTTCCGTAGACACGTCCAAGAACCA

-continued

```
GTTCTCCCTGAAGCTGAGCTCTGTGACCGCCGCAGACACGACTGTGTAT

TACTGTGCGAGACAGGGGTCTACTGTGGTTCGGGGAGTTTACTACTACG

GTATGGACGTCTGGGGCCAAGGGACCACGGTCACCGTCTCCTCAGCTA

GC
```

<H-48-2 heavy chain comprising the variable region>
(SEQ ID NO: 25)

MDLMCKKMKHLWFFLLLVAAPRWVLSQLQLQESGPGLVKPSETLSLTCTV

SGGSISSSSYYWGWVRQPPGKGLEWIGSIHYSGSTFYNPSLKSRVTISVDTS

KNQFSLKLSSVTAADTTVYYCARQGSTVVRGVYYYGMDVWGQGTTVTV

SSAS

<H-48-2 light chain comprising the variable region>
(SEQ ID NO: 26)

```
AGATCTCTCAGTTAGGACCCAGAGGGAACCATGGAAACCCCAGCGCAG

CTTCTCTTCCTCCTGCTACTCTGGCTCCCAGATACCACCGGAGAAATTGT

GTTGACGCAGTCTCCAGGCACCCTGTCTTTGTCTCCAGGGGAAAGAGC

CACCCTCTCCTGCAGGGCCAGTCAGAGTGTTAGCAGCAGCTACTTAGCC

TGGTACCAGCAGAAACCTGGCCAGGCTCCCAGGCTCCTCATCTATGGTG

CATCCAGCAGGGCCACTGGCATCCCAGACAGGTTCAGTGGCAGTGGGT

CTGGGACAGACTTCACTCTCACCATCAGCAGACTGGAGCCTGAAGATTT

TGCAGTGTATTACTGTCAGCAGTATGGTAGCTCACCTCTGTACACTTTTG

GCCAGGGGACCAAGCTGGAGATCAAACGTACG
```

<H-48-2 light chain comprising the variable region>
(SEQ ID NO: 27)

METPAQLLFLLLLWLPDTTGEIVLTQSPGTLSLSPGERATLSCRASQSVSSS

YLAWYQQKPGQAPRLLIYGASSRATGIPDRFSGSGSGTDFTLTISRLEPEDF

AVYYCQQYGSSPLYTFGQGTKLEIKRT

The translation initiation point of the heavy chain DNA is an ATG codon that begins from the 29th adenine (A) from the 5' end of SEQ ID NO: 24. The boundary of the antibody variable region and the constant region is located between the 484th adenine (A) and the 485th guanine (G) from the 5' end. In the amino acid sequence, the heavy chain variable region ranges from the N-terminus to the 152nd serine (S) residue of SEQ ID NO: 25, and the constant region is of the 153rd alanine (A) and the following residues. It was predicted by a gene sequence prediction software (Signal P ver.2) that the heavy chain signal sequence ranges from the N-terminus to the 26th serine (S) of SEQ ID NO: 25. Analysis of the N-terminus of the purified heavy chain protein revealed that the heavy chain signal sequence ranges from the N-terminus to the 26th serine (S) of SEQ ID NO: 25, and the N-terminus of the mature protein is the 27th glutamine (Q) of SEQ ID NO: 25.

The translation initiation point of the light chain DNA is an ATG codon that begins from the 31st A from the 5' end of SEQ ID NO: 26, and the variable region ranges from the 5' end to the 417th adenine (A). In the amino acid sequence, the variable region ranges from the N-terminus to the 129th lysine (K) of SEQ ID NO: 27. Analysis of the N-terminus of the purified light chain protein revealed that the light chain signal sequence ranges from the N-terminus to the 20th glycine (G) of SEQ ID NO: 27, and the N-terminus of the mature protein is the 21st glutamic acid (E) of SEQ ID NO: 27.

(2) cDNA Cloning and Construction of Expression Vector of the 0304 Antibody Gene Hybridoma 0304 cells were collected by centrifugation, and then approximately 900 μg of RNA was purified according to protocols using an ISOGEN RNA extraction reagent (NIPPON GENE). Next, 13 μg of polyA $^+$RNA was obtained from 300 μg of RNA using Oligotex™-dT30<Super> (TAKARA SHUZO CO., LTD.). A cloning experiment was performed using a SMART RACE cDNA Amplification Kit (Clontech company) according the attached instructions using the obtained polyA $^+$RNA as a material, thereby obtaining the cDNA of the variable regions of the antibody gene. Specifically, a first strand cDNA was synthesized by reverse transcriptase using 1.0 μg of the purified polyA $^+$RNA as a material. The H-chain leader sequence and variable region (hereinafter also referred to as "HV") and the L-chain leader sequence and variable region (hereinafter, also referred to as "LV") were amplified by PCR using the obtained cDNA as a template and a primer set: primers (for H-chain: IgG1p; for L-chain: hk-2) for PCR specific to each of the DNAs of a human antibody heavy chain (hereinafter, the heavy chain is also referred to as "H-chain") constant region and light chain (hereinafter, the light chain is also referred to as "L-chain") constant region, and an UMP primer (an oligonucleotide complementary to the common sequence prepared at the 5' end of the synthesized cDNA) attached to a SMART RACE cDNA Amplification Kit. In the PCR, TaKaRa LA Taq™ (TAKARA SHUZO CO., LTD.), which was Taq DNA Polymerase for LA PCR, was used. The template DNA was added to a solution containing 1×LA PCR Buffer II ($Mg^{2+}$ plus) and 400 µM each of dNTP Mixture (in final concentration), 0.2 µM each of two types of primers and 2.5 U TaKaRa LA Taq/50 µl. Reaction was performed by touchdown PCR (94° C. for 5 seconds and 72° C. for 3 minutes (5 cycles)→94° C. for 5 seconds, 70° C. for 10 seconds and 72° C. for 3 minutes (5 cycles)→94° C. for 5 seconds, 68° C. for 10 seconds and 72° C. for 3 minutes (20 cycles)). The amplified PCR fragments were collected by ethanol precipitation, collected by agarose gel electrophoresis, and then purified using a QIAquick Gel Extraction Kit (QIAGEN) which was a DNA purification kit using membranes. For the purified HV and LV fragments, DNA nucleotide sequences were determined using an ABI PRISM® 3700 DNA Analyzer (Applied Biosystems). Furthermore, the amplified HV and LV fragments were subcloned respectively into pGEM®-T Easy Vector Systems (Promega) using the TA cloning method. For the plasmid DNAs of the thus obtained clones, the nucleotide sequences of the insert DNAs were analyzed. The results were compared with the results of the direct sequence analysis made for the PCR product. The sequences of the primers (H-chain: hh-4; L-chain: hk-5 and hk-6; for pGEM®-T Easy Vector: SP6 and T7) used for the determination of the DNA nucleotide sequences are shown in Table 8. The results of the direct sequence analysis made for each of the HV and LV PCR fragments and the results of the analysis of the DNA nucleotide sequences of (subcloned) multiple clones were identical precisely.

The 0304 L-chain leader sequence and variable region were amplified by PCR using the DNA of the 0304 antibody L-chain as a template, and primers that had been designed to add a restriction enzyme site to the end for ligation. The sequences of the primer set used herein are shown in Table 8 (C23LBCL and C23LBsi). The obtained PCR fragments were collected by ethanol precipitation, digested with a restriction enzyme Bgl II and then cleaved with BsiW I. The digested product was subjected to agarose gel electrophoresis, so that a fragment of approximately 400 bp was collected. Purification was performed using a QIAquick Gel Extraction Kit (QIAGEN) which was a DNA purification kit using membranes. In the meantime, N5KG4-Val Lark which was a vector (IDEC Pharmaceuticals, an altered vector of N5KG1 (U.S. Pat. No. 6,001,358)) was similarly digested with restriction enzymes Bgl II and BsiW I sequentially, and then subjected to dephosphorylation treatment (treated with Alkaline Phosphatase (E. coli C75) (TAKARA SHUZO CO., LTD.)). Then, less than approximately 9 kb DNAs were collected by agarose gel electrophoresis and a DNA purification kit. These 2 fragments were ligated using T4 DNA ligase and then introduced into Escherichia coli DH5α, so as to obtain a transformant. A plasmid DNA, N5KG4-0304L, that had been prepared by inserting the 0304 antibody L-chain leader+variable region into N5KG4-Val Lark was selected. The DNA nucleotide sequences surrounding the inserted fragment were determined, thereby confirming that there was no mutation or the like in the DNA nucleotide sequences. To insert the H-chain variable region and the like into the thus obtained N5KG4-0304L, this plasmid DNA was sequentially cleaved with restriction enzymes Nhe I and Sal I, dephosphorylation treatment was performed, and then an approximately 9.3 kb vector DNA was purified. In the meantime, the 0304 antibody H-chain gene leader sequence and variable region were amplified by PCR using the plasmid DNA of the antibody H-chain as a template. The primer set used for amplification (T0304Sal and T0304Nhe) is shown in Table 8.

The obtained PCR fragment was cleaved with restriction enzymes Nhe I and Sal I, and then subjected to agarose gel electrophoresis, thereby purifying approximately 450 bp fragments. These 2 types of DNAs were ligated and introduced into Escherichia coli to obtain transformants, and then clones having the target H-chain leader sequence and variable region inserted therein were selected. The DNA nucleotide sequence of the insertion portion was determined, thereby confirming that there was no difference between the inserted sequence amplified by PCR and the gene sequence used as a template.

DNAs encoding the 0304 heavy chain variable region and light chain variable region, and the amino acid sequences comprising the heavy chain variable region and the light chain variable region, are as respectively shown below.

```
<0304 heavy chain comprising the variable region> (SEQ ID NO: 28)

CTCAACAACC ACATCTGTCC TCTAGAGAAA ACCCTGTGAG CACAGCTCCT CACCATGGAC

TGGACCTGGA GGATCCTCTT CTTGGTGGCA GCAGCTACAA GTGCCCACTC CCAGGTGCAG

CTGGTGCAGT CTGGGGCTGA GATGAAGAAG CCTGGGGCCT CAGTCAAGGT CTCCTGCAAG

ACTTCTGGAT ACACCTTCAC CAATTATAAG ATCAACTGGG TGCGACAGGC CCCTGGACAA

GGACTTGAGT GGATGGGATC GATGAACCCT GACACTGATA GCACAGGCTA TCCACAGAAG

TTCCAGGGCA GAGTCACCAT GACCAGGAAC ACCTCCATAA GCACAGCCTA CATGGAGCTG

AGCAGCCTGA GATCTGAGGA CACGGCCGTG TATTACTGTG CGAGATCCTA TGGTTCGGGG

AGTTATTATA GAGACTATTA CTACGGTATG GACGTCTGGG GCCAAGGGAC CACGGTCACC

GTCTCCTCA

<0304 heavy chain comprising the variable region> (SEQ ID NO: 29)
```

```
MDWTWRILFL VAAATSAHSQ VQLVQSGAEM KKPGASVKVS CKTSGYTFTN YKINWVRQAP

GQGLEWMGWM NPDTDSTGYP QKFQGRVTMT RNTSISTAYM ELSSLRSEDT AVYYCARSYG

SGSYYRDYYY GMDVWGQGTT VTVSS

<0304 light chain comprising the variable region> (SEQ ID NO: 30)

GAGGAACTGC TCAGTTAGGA CCCAGAGGGA ACCATGGAAG CCCCAGCTCA GCTTCTCTTC

CTCCTGCTAC TCTGGCTCCC AGATACCACC GGAGAAATTG TGTTGACACA GTCTCCAGCC

ACCCTGTCTT TGTCTCCAGG GGAAAGAGCC ACCCTCTCCT GCAGGGCCAG TCAGAGTGTT

AGCAGCTACT TAGCCTGGTA CCAACAGAAA CCTGGCCAGG CTCCCAGGCT CCTCATCTAT

GATGCATCCA ACAGGGCCAC TGGCATCCCA GCCAGGTTCA GTGGCAGTGG GTCTGGGACA

GACTTCACTC TCACCATCAG CAGCCTAGAG CCTGAAGATT TTGCAGTTTA TTACTGTCAG

CAGCGTAGCA ACTGGCCGCT CACTTTCGGC GGAGGGACCA AGGTGGAGAT CAAACGA

<0304 light chain comprising the variable region> (SEQ ID NO: 31)

MEAPAQLLFL LLLWLPDTTG EIVLTQSPAT LSLSPGERAT LSCRASQSVS SYLAWYQQKP

GQAPRLLIYD ASNRATGIPA RFSGSGSGTD FTLTISSLEP EDFAVYYCQQ RSNWPLTFGG

GTKVEIKR
```

The translation initiation point of the heavy chain DNA is an ATG codon that begins from the 55th adenine (A) from the 5' end of SEQ ID NO: 28. The antibody variable region ranges from the 5' end to the 489th adenine (A). In the amino acid sequence, the heavy chain variable region ranges from the N-terminus to the 145th serine (S) residue of SEQ ID NO: 29. It was predicted by a gene sequence prediction software (Signal P ver.2) that the heavy chain signal sequence ranges from the N-terminus to the 19th serine (S) of SEQ ID NO: 29. The N-terminus of the mature protein is thought to be the 20th glutamine (Q) of SEQ ID NO: 29.

The translation initiation point of the light chain DNA is an ATG codon that begins from the 34th A from the 5' end of SEQ ID NO: 30, and the variable region ranges from the 5' end to the 414th adenine (A). In the amino acid sequence, the variable region ranges from the N-terminus to the 127th lysine (K) of SEQ ID NO: 31. It was predicted by a gene sequence prediction software (Signal P ver.2) that the light chain signal sequence ranges from the N-terminus to the 20th glycine (G) of SEQ ID NO: 31. The N-terminus of the mature protein is thought to be the 21st glutamic acid (E) of SEQ ID NO: 31.

TABLE 8

Nucleotide Sequence of Synthetic DNA

| No | Primer name | Sequence (5' to 3') | Length | SEQ ID NO: |
|---|---|---|---|---|
| 1 | IgG1 | TCTTGTCCACCTTGGTGTTGCTGGGCTTGTG | 31-mer | 36 |
| 2 | hk-2 | GTTGAAGCTCTTTGTGACGGGCGAGC | 26-mer | 12 |
| 3 | hh-4 | GGTGCCAGGGGGAAGACCGATGG | 23-mer | 9 |
| 4 | hk-5 | AGGCACACAACAGAGGCAGTTCCAGATTTC | 30-mer | 37 |
| 5 | hk-6 | TGGCGGGAAGATGAAGACAGATGGTG | 26-mer | 13 |
| 6 | SP6 | GATTTAGGTGACACTATAG | 19-mer | 38 |
| 7 | T7 | TAATACGACTCACTATAGGG | 20-mer | 39 |
| 8 | C23LBCL | ATCACAGATCTCTCACCATGGAAGCCCCAGCTC AGCTTCTC | 41-mer | 40 |
| 9 | C23LBsi | GGTGCAGCCACCGTACGTTTGATCTCCACCTTG | 33-mer | 41 |
| 10 | T0304Sal | GCGACTAAGTCGACACCATGGACTGGACCTGG AGGATC | 38-mer | 42 |
| 11 | T0304Nhe | AGAGAGAGAGGCTAGCTGAGGAGACGGTGACC | 32-mer | 43 |
| 12 | SEQU1783 | GGTACGTGAACCGTCAGATCGCCTGGA | 27-mer | 44 |
| 13 | SEQU4618 | TCTATATAAGCAGAGCTGGGTACGTCC | 27-mer | 45 |

(3) cDNA Cloning of KMTR1 Antibody Gene

Hybridoma KMTR1 cells were collected by centrifugation, and then approximately 900 μg of RNA was purified using an ISOGEN RNA extraction reagent (NIPPON GENE) according to protocols. Next, 13 μg of polyA $^+$RNA was obtained from 300 μg of RNA using Oligotex™-dT30<Super> (TAKARA SHUZO CO., LTD.). A cloning experiment was performed using a SMART RACE cDNA Amplification Kit (Clontech-company) according the attached instructions using the obtained polyA $^+$RNA as a material, thereby obtaining the cDNA of the variable regions of the antibody gene. Specifically, a first strand cDNA was synthesized by reverse transcriptase using 1.0 μg of the purified polyA +RNA as a material. The H-chain leader sequence and variable region (hereinafter also referred to as "HV") and the L-chain leader sequence and variable region (hereinafter, also referred to as "LV") were amplified by PCR using the obtained cDNA as a template and a primer set: primers (for H-chain: IgG1p; for L-chain: hk-2) for PCR specific to each of the DNAs of a human antibody heavy chain (hereinafter, the heavy chain is also referred to as "H-chain") constant region and light chain (hereinafter, the light chain is also referred to as "L-chain") constant region, and an UMP primer (an oligonucleotide complementary to the common sequence prepared at the 5' end of the synthesized cDNA) attached to a SMART RACE cDNA Amplification Kit. In the PCR, TaKaRa LA Taq™ (TAKARA SHUZO CO., LTD.), which was Taq DNA Polymerase for LA PCR, was used. The template DNA was added to a solution containing 1×LA PCR Buffer II ($Mg^{2+}$ plus) and 400 μM each of dNTP Mixture (in final concentration), 0.2 μM each of two types of primers and 2.5 U TaKaRa LA Taq/50 μl. Reaction was performed by touchdown PCR (94° C. for 5 seconds and 72° C. for 3 minutes (5 cycles)→94° C. for 5 seconds, 70° C. for 10 seconds and 72° C. for 3 minutes (5 cycles)→94° C. for 5 seconds, 68° C. for 10 seconds and 72° C. for 3 minutes (20 cycles)). The amplified PCR fragment was collected by ethanol precipitation, collected by agarose gel electrophoresis, and then purified using a QIAquick Gel Extraction Kit (QIAGEN) which was a DNA purification kit using membranes. For the purified HV and LV fragments, DNA nucleotide sequences were determined using an ABI PRISM® 3700 DNA Analyzer (Applied Biosystems). Furthermore, the amplified HV and LV fragments were subcloned respectively into pGEM®-T Easy Vector System (Promega) using the TA cloning method. For the plasmid DNAs of the thus obtained clones, the nucleotide sequences of the insert DNAs were analyzed. The results were compared with the results of the direct sequence analysis made for the PCR product. The sequences of the primers used for the determination of the DNA nucleotide sequences (H-chain: hh-4; L-chain: hk-5 and hk-6; for pGEM®-T Easy Vector: SP6 and T7) are shown in Table 8 above. The results of the direct sequence analysis made for each of the HV and LV PCR fragments and the results of the analysis of the DNA nucleotide sequences of multiple clones (subcloned) were identical precisely. The thus determined DNA nucleotide sequences encoding the HV and the LV and the amino acid sequences comprising the HV and the LV of the H-chain and the L-chain of the human antibody gene expressed on the KMTR1 cell are shown.

```
<KMTR1 heavy chain comprising the variable region> (SEQ ID NO: 32)

GAGCTCTGAG AGAGGAGCCC AGCCCTGGGA TTTTCAGGTG TTTTCATTTG GTGATCAGGA

CTGAACAGAG AGAACTCACC ATGGAGTTTG GGCTGAGCTG GCTTTTTCTT GTGGCTATTT

TAAAAGGTGT CCAGTGTGAG GTACAGCTGT TGGAGTCTGG GGGAGGCTTG GTACAGCCTG

GGAGGTCCCT GAGACTCTCC TGTGCAGCCT CTGGATTCAC CTTTAGCAGC TATGCCATGA

GCTGGGTCCG CCAGGCTCCA GGGAAGGGGC TGGAGTGGGT CTCAGCTATT AGTGGTAGTG

GTGGTAGCAG ATACTACGCA GACTCCGTGA AGGGCCGGTT CACCATCTCC AGAGACAATT

CCAAGAACAC GCTGTATCTG CAAATGAACA GCCTGAGAGC CGAGGACACG GCCGTATATT

ACTGTGCGAA AGAGAGCAGT GGCTGGTTCG GGGCCTTTGA CTACTGGGGC CAGGGAACCC

TGGTCACCGT CTCCTCA

<KMTR1 heavy chain comprising the variable region> (SEQ ID NO: 33)

MEFGLSWLFL VAILKGVQCE VQLLESGGGL VQPGRSLRLS CAASGFTFSS YAMSWVRQAP

GKGLEWVSAI SGSGGSRYYA DSVKGRFTIS RDNSKNTLYL QMNSLRAEDT AVYYCAKESS

GWFGAFDYWG QGTLVTVSS

<KMTR1 light chain comprising the variable region> (SEQ ID NO: 34)

GATCTTAAAA GAGGTTCTTT CTCTGGGATG TGGCATGAGC AAAACTGACA AGTCAAGGCA

GGAAGATGTC GCCATCACAA CTCATTGGGT TTCTGCTGCT CTGGGTTCGA GCGTCCAGGG

GTGAAATTGT GCTGACTCAG TCTCCAGACT TTCAGTCTGT GACTCCAAAG GAGAAAGTCA

CCATCACCTG CCGGGCCAGT CAGAGCATTG GTAGTAGCTT ACACTGGTAC CAGCAGAAAC

CAGATCAGTC TCCAAAGCTC CTCATGAAGT ATGCTTCCCA GTCCTTCTCA GGGGTCCCCT

CGAGGTTCAG TGGCAGTGGA TCTGGGACAG ATTTCACCCT CACCATCAAT AGCCTGGAAG

CTGAAGATGC TGCAGCGTAT TACTGTCATC AGAGTAGTAG TTTACCGATC ACCTTCGGCC

AAGGGACACG ACTGGAGATT AAACGA

<KMTR1 light chain comprising the variable region> (SEQ ID NO: 35)
```

-continued

```
MSPSQLIGFL LLWVPASRGE IVLTQSPDFQ SVTPKEKVTI TCRASQSIGS SLHWYQQKPD

QSPKLLIKYA SQSFSGVPSR FSGSGSGTDF TLTINSLEAE DAAAYYCHQS SSLPITFGQG

TRLEIKR
```

The translation initiation point of the heavy chain DNA is an ATG codon that begins from the 81st adenine (A) from the 5' end of SEQ ID NO: 32. The antibody variable region ranges from the 5' end to the 497th adenine (A). In the amino acid sequence, the heavy chain variable region ranges from the N-terminus to the 139th serine (S) residue of SEQ ID NO: 33. It was predicted by a gene sequence prediction software (Signal P ver.2) that the heavy chain signal sequence ranges from the N-terminus to the 19th cysteine (C) of SEQ ID NO: 33. The N-terminus of the mature protein is thought to be the 20th glutamic acid (E) of SEQ ID NO: 33.

The translation initiation point of the light chain DNA is an ATG codon that begins from the 66th A from the 5' end of SEQ ID NO: 34, and the variable region ranges from the 5' end to the 443rd adenine (A). In the amino acid sequence, the variable region ranges from the N-terminus to the 126th lysine (K) of SEQ ID NO: 35. It was predicted by a gene sequence prediction software (Signal P ver.2) that the light chain signal sequence ranges from the N-terminus to the 19th glycine (G) of SEQ ID NO: 35. The N-terminus of the mature protein is thought to be the 20th glutamic acid (E) of SEQ ID NO: 35.

Example 15

Preparation of Recombinant Antibody

The recombinant antibody expression vector constructed in Example 14 was introduced into a host cell, thereby preparing a recombinant antibody-expressing cell. As the host cell for expression, for example, a dhfr-deficient strain (ATCC CRL-9096) of CHO cells was used. The vector was introduced into a host cell by electroporation. Approximately 2 µg of the antibody expression vector was linearized with a restriction enzyme. Under conditions of 350 V and 500 µF, the gene was introduced into $4 \times 10^6$ CHO cells using a Bio-Rad electrophoreter, and then the cells were seeded in a 96-well culture plate. A drug corresponding to a selection marker of the expression vector was added, and then culturing was continued. After colonies were confirmed, antibody-expressing lines were selected by the method described in Example 4. The antibodies were purified from the selected cells as described in Example 10.

Example 16

Cell-Death-Inducing Activity of Recombinant Antibody on Carcinoma Cell

The cell-death-inducing activity on Colo205 (ATCC No. CCL-222), the colon carcinoma cell, was measured using the recombinant human anti-TRAIL-R2 monoclonal antibodies obtained in Example 15. Colo205 cells cultured in RPMI media containing 10% FCS were prepared at a concentration of $1.0 \times 10^5$/ml, and then 100 µl of the suspension was added to each well of a 96-well flat-bottomed plate (Beckton Dickinson). After 24 hours of culturing at 37° C. under 5.0% carbon dioxide gas, the purified antibodies E11 (CHO-3) and H48 (CHO-3) were added (10 µl/well) at final concentrations of 10, 100, 1000 and 10000 ng/ml. Further, 10 µl of goat anti-human IgG (γ)-specific polyclonal antibodies (Sigma) were added to each well at final concentrations of 10 and 100 µg/ml. For the obtained hybridomas, wells supplemented with no goat anti-human IgG (γ)-specific polyclonal antibodies were prepared. As a positive control, human recombinant TRAIL proteins (R&D SYSTEMS) with final concentrations of 1 and 10 ng/ml were used. A human anti-HSA antibody was used as a negative control. After 48 hours of culturing at 37° C. under 5.0% carbon dioxide gas, an MTS reagent (Cell Titer 96 AQ$_{UEOUS}$ Non-Radioactive Cell Proliferation Assay: Promega) was prepared according to the method described in the instructions. 20 µl of the reagent was added to each well. After 2 hours of culturing at 37° C. under 5.0% carbon dioxide gas, absorbance at a wavelength of 490 nm (reference wavelength of 630 nm) was measured using a microplate reader (1420 ARVO multi-label counter: WALLAC). Using the reducibility of the mitochondria as an indicator, the survival rate of the cells was calculated. The survival rate of the cells in each well was calculated using a formula similar to that of Example 7.

Figure 11A:
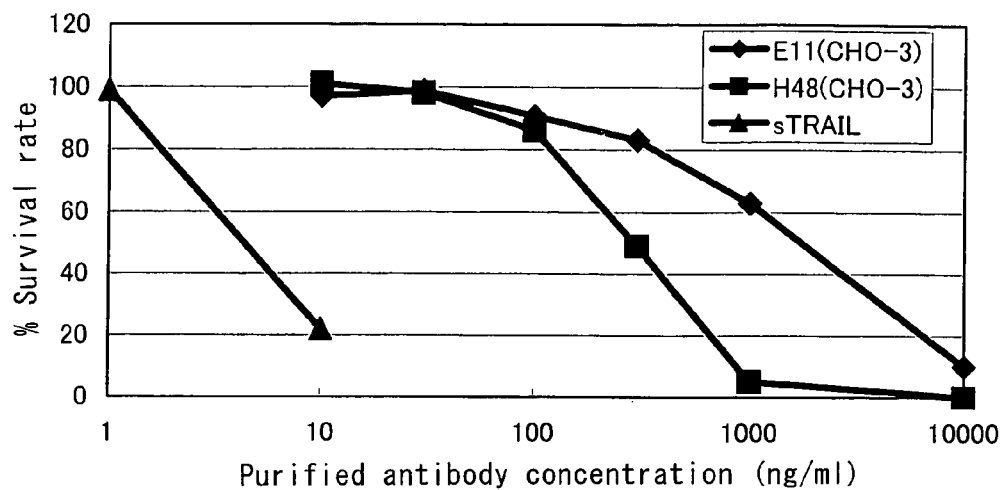
FIG. 11a shows the cell-death-inducing activity (Goat anti-human IgG antibodies were not added) of recombinant purified human anti-TRAIL-R2 monoclonal antibodies on Colo205 cells.
Figure 11B:
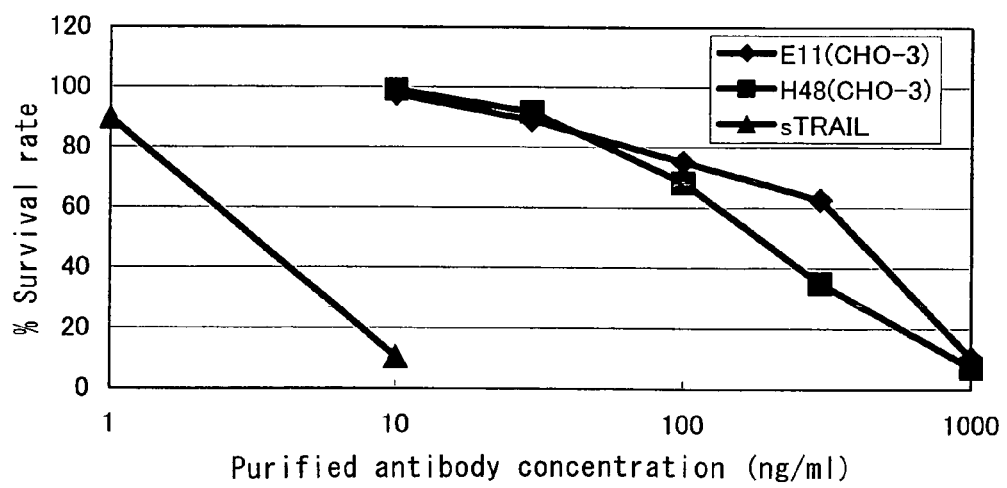
FIG. 11b shows the cell-death-inducing activity (Goat anti-human IgG antibodies were added) of recombinant purified human anti-TRAIL-R2 monoclonal antibodies on Colo205 cells.

FIG. 11a and 11b show the results. FIG. 11a shows the result of an experiment wherein no goat anti-human IgG(γ)-specific polyclonal antibody was added, and FIG. 11b shows the result of an experiment wherein goat anti-human IgG (γ)-specific polyclonal antibodies were added.

As shown in FIG. 11a, the recombinant antibodies E11 (CHO-3) and H48(CHO-3) have activity to induce cell death in Colo205 cells in the case of the antibody alone. Moreover, as shown in FIG. 11b, when goat anti-human IgG(γ)-specific polyclonal antibodies were added, the recombinant antibodies showed cell-death-inducing activity equivalent to that of the antibody purified from the culture supernatant of the hybridoma.

All publications, patents and patent applications cited herein are incorporated herein by reference in their entirety.

INDUSTRIAL APPLICABILITY

According to the present invention, there is provided a molecule with extremely high safety, which is useful as a prophylactic or therapeutic agent against disease, in particular malignant tumors, caused by TRAIL-R1 and R2-expressing cells, and which can avoid damage to the liver.

Sequence Listing Free Text
SEQ ID NO: 1: synthetic DNA
SEQ ID NO: 2: synthetic DNA
SEQ ID NO: 3: synthetic DNA
SEQ ID NO: 4: synthetic DNA
SEQ ID NO: 5: synthetic DNA
SEQ ID NO: 6: synthetic DNA
SEQ ID NO: 7: synthetic DNA
SEQ ID NO: 8: synthetic DNA
SEQ ID NO: 9: synthetic DNA
SEQ ID NO: 10: synthetic DNA
SEQ ID NO: 11: synthetic DNA
SEQ ID NO: 12: synthetic DNA SEQ ID NO: 13: synthetic DNA
SEQ ID NO: 14: synthetic DNA
SEQ ID NO: 15: synthetic DNA
SEQ ID NO: 36: synthetic DNA
SEQ ID NO: 37: synthetic DNA
SEQ ID NO: 38: synthetic DNA
SEQ ID NO: 39: synthetic DNA
SEQ ID NO: 40: synthetic DNA
SEQ ID NO: 41: synthetic DNA
SEQ ID NO: 42: synthetic DNA
SEQ ID NO: 43: synthetic DNA
SEQ ID NO: 44: synthetic DNA
SEQ ID NO: 45: synthetic DNA

The invention claimed is:

1. An antibody or antigen binding fragment thereof, said antibody or fragment having the mature portions of:
- a heavy chain variable region and a light chain variable region of SEQ ID NO: 17 and SEQ ID NO: 19, respectively;
- a heavy chain variable region and a light chain variable region of SEQ ID NO: 21 and SEQ ID NO: 23, respectively;
- a heavy chain variable region and a light chain variable region of SEQ ID NO: 25 and SEQ ID NO: 27, respectively;
- a heavy chain variable region and a light chain variable region of SEQ ID NO: 29 and SEQ ID NO: 31, respectively; or
- a heavy chain variable region and a light chain variable region of SEQ ID NO: 33 and SEQ ID NO: 35, respectively.

2. An antibody or antigen binding fragment thereof, said antibody or fragment having the mature portions of a heavy chain variable region and a light chain variable region of SEQ ID NO: 29 and SEQ ID NO: 31, respectively.

3. An antibody or a functional antigen binding fragment thereof, said antibody or fragment having the mature portions of:
  a heavy chain variable region and a light chain variable region of the antibody produced by a hybridoma E-11-13 with the accession number of FERM BP-7698 or FERM BP-7770;
  a heavy chain variable region and a light chain variable region of the antibody produced by a hybridoma L-30-10 with the accession number of FERM E3P-7700 or FERM BP-7769;
  a heavy chain variable region and a light chain variable region of the antibody produced by a hybridoma H-48-2 with the accession number of FERM BP-7599;
  a heavy chain variable region and a light chain variable region of the antibody produced by a hybridoma 0304 with the accession number of FERM BP-8037; or
  a heavy chain variable region and a light chain variable region of the antibody produced by a hybridoma KMTR1 with the accession number of FERM BP-8038.

4. An antibody or antigen binding fragment thereof, said antibody or fragment having the mature portions of a heavy chain variable region and a light chain variable region of the antibody produced by a hybridoma 0304 with the accession number of FERM BP-8037.

5. An antibody or antibody binding fragment thereof, said antibody or fragment having the mature portions of a heavy chain variable region and a light chain variable region:
  which are amino acids 27 to 144 of SEQ ID NO: 17 and amino acids 21 to 127 of SEQ ID NO: 19, respectively;
  which are amino acids 27 to 144 of SEQ ID NO: 21 and amino acids 21 to 127 of SEQ ID NO: 23, respectively;
  which are amino acids 27 to 152 of SEQ ID NO: 25 and amino acids 21 to 129 of SEQ ID NO: 27, respectively;
  which are amino acids 20 to 145 of SEQ ID NO: 29 and amino acids 21 to 127 of SEQ ID NO: 31, respectively; or
  which are amino acids 20 to 139 of SEQ ID NO: 33 and amino acids 20 to 126 of SEQ ID NO: 35, respectively.

6. An antibody or antigen binding fragment thereof, said antibody or fragment having the mature portions of a heavy chain variable region and a light chain variable region of:
  amino acids 20 to 145 of SEQ ID NO: 29 and amino acids 21 to 127 of SEQ ID NO: 31, respectively.

7. An antibody or antigen binding fragment thereof, having the mature portions of:
  a heavy chain variable region and a light chain variable region encoded by the nucleic acids of SEQ ID NO: 16 and SEQ ID NO: 18, respectively;
  a heavy chain variable region and a light chain variable region encoded by the nucleic acids of SEQ ID NO: 20 and SEQ ID NO: 22, respectively;
  a heavy chain variable region and a light chain variable region encoded by the nucleic acids of SEQ ID NO: 24 and SEQ ID NO: 26, respectively;
  a heavy chain variable region and a light chain variable region encoded by the nucleic acids of SEQ ID NO: 28 and SEQ ID NO: 30, respectively; or
  a heavy chain variable region and a light chain variable region encoded by the nucleic acids of SEQ ID NOS: 32 and SEQ ID NO: 34, respectively.

8. An antibody or antigen binding fragment thereof, having the mature portions of a heavy chain variable region and a light chain variable region encoded by the nucleic acids of SEQ ID NOS: 28 and 30, respectively.

9. An antibody or antigen binding fragment thereof, having the mature portions of:
  a heavy chain variable region and a light chain variable region encoded by nucleic acids isolated from a hybridoma E-11-13 with the accession number of FERM BP-7698 or FERM BP-7770;
  a heavy chain variable region and a light chain variable region encoded by nucleic acids isolated from a hybridoma E-30-10 with the accession number of FERM BP-7700 or FERM BP-7789;
  a heavy chain variable region and a light chain variable region encoded by nucleic acids isolated from a hybridoma M-48-2 with the accession number of FERM BP-7599;
  a heavy chain variable region and a light chain variable region encoded by nucleic acids isolated from a hybridoma 0304 with the accession number of FERM 6P-8037; or
  a heavy chain variable region and a light chain variable region encoded by nucleic acids isolated from a hybridoma KMTR1 with the accession number of FERM BP-8038.

10. An antibody or antigen binding fragment thereof, having the mature portions of a heavy chain variable region and a light chain variable region encoded by nucleic acids isolated from a hybridoma 0304 with the accession number of FERM BP-8037.

11. An antibody or antigen binding fragment thereof, having the mature portions of a heavy chain variable region and a light chain variable region:
  which are encoded by nucleotides 108 to 461 of SEQ ID NO: 16 and 95 to 415 of SEQ ID NO: 18, respectively;
  which are encoded by nucleotides 108 to 46 of SEQ ID NO: 20 and 91 to 411 of SEQ ID NO: 22, respectively;
  which are encoded by nucleotides 107 to 484 of SEQ ID NO: 24 and 91 to 417 of SEQ ID NO: 26, respectively;
  which are encoded by nucleotides 112 to 489 of SEQ ID NO: 28 and 94 to 414 of SEQ ID NO: 30, respectively; or
  which are encoded by nucleotides 138 to 497 of SEQ ID NO: 32 and 123 to 443 of SEQ ID NO: 34, respectively.

12. An antibody or antigen binding fragment thereof, having the mature portions of a heavy chain variable region and a light chain variable region encoded by nucleotides 112 to 489 of SEQ ID NO: 28 and 94 to 414 of SEQ ID NO: 30, respectively.

13. The antibody or antigen binding fragment thereof, according to any one of claims 1 to 6 and 7–12, which is an IgG.

14. The antibody or antigen binding fragment thereof, according to claim 13, which is an IgG 1.

* * * * *

SEQUENCE LISTING

<160> NUMBER OF SEQ ID NOS: 45

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
cacgaattca ccatggcgcc accaccagct                                      30

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
tttctcgagg cggccgctta tcactccaag gacacggcag agcctgtg                  48

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
cacgaattcg ccaccatgga acaacgggga cag                                  33

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
tttctcgagg cggccgctca ttaggacatg gcagagtctg cattacct                  48

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
ttctacgagc ggcttatcac agcctcctcc tctgaga                              37

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
ttctacgagc ggccgcttat cacaagtctg caaagtcatc                          40

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
ggtccgggag atcatgaggg tgtcctt                                        27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
gtgcacgccg ctggtcaggg cgcctg                                         26

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
ggtgccaggg ggaagaccga tgg                                            23

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
atatagatct ctcagttagg acccagaggg aacc                                34

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
gatgggccct tggtgctagc tgaggagacg g                                   31

```
<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
gttgaagctc tttgtgacgg gcgagc                                          26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 13
tggcgggaag atgaagacag atggtg                                          26

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 14
atatgtcgac tacgggggggg ctttctgaga gtc                                 33

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 15
aagacagatg gtgcagccac cgtacgtttg at                                   32

<210> SEQ ID NO 16
<211> LENGTH: 467
<212> TYPE: DNA
<213> ORGANISM: Homo sapiens

<400> SEQUENCE: 16
gtcgactacg gggggctttt ctgagagtca tggatctcat gtgcaagaaa atgaagcacc      60
tgtggttctt cctcctgctg gtggcggctc ccagatgggt cctgtcccag ctgcagctgc     120
aggagtcggg cccaggactg gtgaagcctt cggagaccct gtccctcacc tgcactgtct     180
ctggtggctc catcatcagt aaaagttcct actggggctg gatccgccag ccccagggaa     240 agggggctgga gtggattggg agtatctatt atagtgggag taccttctac aacccgtccc     300
tcaagagtcg agtcaccata tccgtagaca cgtccaagaa ccagttctcc ctgaagctga     360
gctctgtgac cgccgcagac acggctgtgt attactgtgc gagactgaca gtggctgagt     420
ttgactactg gggccaggga accctggtca ccgtctcctc agctagc                   467

<210> SEQ ID NO 17
<211> LENGTH: 146
<212> TYPE: PRT
```

<210> SEQ ID NO 17 (continued)

<213> ORGANISM: Homo sapiens

<400> SEQUENCE: 17

```
Met Asp Leu Met Cys Lys Lys Met Lys His Leu Trp Phe Phe Leu Leu
 1               5                  10                  15
Leu Val Ala Ala Pro Arg Trp Val Leu Ser Gln Leu Gln Leu Gln Glu
             20                  25                  30
Ser Gly Pro Gly Leu Val Lys Pro Ser Glu Thr Leu Ser Leu Thr Cys
         35                  40                  45
Thr Val Ser Gly Gly Ser Ile Ile Ser Lys Ser Ser Tyr Trp Gly Trp
     50                  55                  60
Ile Arg Gln Pro Pro Gly Lys Gly Leu Glu Trp Ile Gly Ser Ile Tyr
 65                  70                  75                  80
Tyr Ser Gly Ser Thr Phe Tyr Asn Pro Ser Leu Lys Ser Arg Val Thr
                 85                  90                  95
Ile Ser Val Asp Thr Ser Lys Asn Gln Phe Ser Leu Lys Leu Ser Ser
            100                 105                 110
Val Thr Ala Ala Asp Thr Ala Val Tyr Tyr Cys Ala Arg Leu Thr Val
        115                 120                 125
Ala Glu Phe Asp Tyr Trp Gly Gln Gly Thr Leu Val Thr Val Ser Ser
    130                 135                 140
Ala Ser
145
```

<210> SEQ ID NO 18
<211> LENGTH: 421
<212> TYPE: DNA
<213> ORGANISM: Homo sapiens

<400> SEQUENCE: 18

```
tcacagatct ctcagttagg acccagaggg aaccatggaa gccccagctc agcttctctt    60
cctcctgcta ctctggctcc cagataccac cggagaaatt gtgttgacac agtctccagc   120
caccctgtct ttgtctccag gggaaagagc caccctctcc tgcagggcca gtcagagtgt   180
tagcagcttc ttagcctggt accaacagaa acctggccag gctcccaggc tcctcatcta   240
tgatgcatcc aacagggcca ctggcatccc agccaggttc agtggcagtg gatctgggac   300
agacttcact ctcaccatca gcagcctaga gcctgaagat tttgcagttt attactgtca   360
gcagcgtagc aactggcctc tcactttcgg ccctgggacc aaagtggata tcaaacgtac   420
g                                                                   421
```

<210> SEQ ID NO 19
<211> LENGTH: 129
<212> TYPE: PRT
<213> ORGANISM: Homo sapiens

<400> SEQUENCE: 19

```
Met Glu Ala Pro Ala Gln Leu Leu Phe Leu Leu Leu Leu Trp Leu Pro
 1               5                  10                  15
Asp Thr Thr Gly Glu Ile Val Leu Thr Gln Ser Pro Ala Thr Leu Ser
             20                  25                  30
Leu Ser Pro Gly Glu Arg Ala Thr Leu Ser Cys Arg Ala Ser Gln Ser
         35                  40                  45
Val Ser Ser Phe Leu Ala Trp Tyr Gln Gln Lys Pro Gly Gln Ala Pro
     50                  55                  60
Arg Leu Leu Ile Tyr Asp Ala Ser Asn Arg Ala Thr Gly Ile Pro Ala
```

```
                65                  70                  75                  80
Arg Phe Ser Gly Ser Gly Ser Gly Thr Asp Phe Thr Leu Thr Ile Ser
                            85                  90                  95

Ser Leu Glu Pro Glu Asp Phe Ala Val Tyr Tyr Cys Gln Gln Arg Ser
                100                 105                 110

Asn Trp Pro Leu Thr Phe Gly Pro Gly Thr Lys Val Asp Ile Lys Arg
        115                 120                 125

Thr

<210> SEQ ID NO 20
<211> LENGTH: 467
<212> TYPE: DNA
<213> ORGANISM: Homo sapiens

<400> SEQUENCE: 20
gtcgactacg gggggctttt ctgagagtca tggatctcat gtgcaagaaa atgaagcacc      60
tgtggttctt cctcctgctg gtggcggctc ccagatgggt cctgtcccag ttgcagctgc     120
aggagtcggg cccaggactg gtgaagccct cggagaccct gtccctcacc tgcactgtct     180
ctggtggctc catcagcagt aggagtaact actggggctg gatccgccag cccccaggga     240
agggcctgga gtggattggg aatgtctatt atagagggag cacctactac aattcgtccc     300
tcaagagtcg agtcaccata tccgtagaca cgtccaagaa ccagttctcc ctgaagctga     360
gctctgtgac cgtcgcagac acggctgtgt attactgtgc gagactgtca gtggctgagt     420
ttgactactg gggccaggga atcctggtca ccgtctcctc agctagc                   467

<210> SEQ ID NO 21
<211> LENGTH: 146
<212> TYPE: PRT
<213> ORGANISM: Homo sapiens

<400> SEQUENCE: 21

Met Asp Leu Met Cys Lys Lys Met Lys His Leu Trp Phe Phe Leu Leu
1               5                   10                  15

Leu Val Ala Ala Pro Arg Trp Val Leu Ser Gln Leu Gln Leu Gln Glu
            20                  25                  30

Ser Gly Pro Gly Leu Val Lys Pro Ser Glu Thr Leu Ser Leu Thr Cys
        35                  40                  45

Thr Val Ser Gly Gly Ser Ile Ser Ser Arg Ser Asn Tyr Trp Gly Trp
    50                  55                  60

Ile Arg Gln Pro Pro Gly Lys Gly Leu Glu Trp Ile Gly Asn Val Tyr
65                  70                  75                  80

Tyr Arg Gly Ser Thr Tyr Tyr Asn Ser Ser Leu Lys Ser Arg Val Thr
                85                  90                  95

Ile Ser Val Asp Thr Ser Lys Asn Gln Phe Ser Leu Lys Leu Ser Ser
                100                 105                 110

Val Thr Val Ala Asp Thr Ala Val Tyr Tyr Cys Ala Arg Leu Ser Val
            115                 120                 125

Ala Glu Phe Asp Tyr Trp Gly Gln Gly Ile Leu Val Thr Val Ser Ser
        130                 135                 140

Ala Ser
145

<210> SEQ ID NO 22
<211> LENGTH: 417
<212> TYPE: DNA
```

<210> SEQ ID NO 22
<211> LENGTH: 417
<212> TYPE: DNA
<213> ORGANISM: Homo sapiens

<400> SEQUENCE: 22

```
agatctctca gttaggaccc agagggaacc atggaagccc cagctcagct tctcttcctc     60
ctgctactct ggctcccaga taccaccgga gaaattgtgt tgacacagtc tccagccacc    120
ctgtctttgt ctccagggga agagccacc ctctcttgta gggccagtca gagtgttagc    180
agcttcttag cctggtacca acagaaacct ggccaggctc ccaggctcct catctatgat    240
gcatccaaca gggccactgg cagcccagcc aggttcagtg gcagtgggtc tgggacagac    300
ttcactctca ccatcagcag cctagagcct gaagattttg cagtttatta ctgtcagcag    360
cgtagcgact ggcctctcac tttcggccct gggaccaaag tggatatcaa acgtacg       417
```

<210> SEQ ID NO 23
<211> LENGTH: 129
<212> TYPE: PRT
<213> ORGANISM: Homo sapiens

<400> SEQUENCE: 23

```
Met Glu Ala Pro Ala Gln Leu Leu Phe Leu Leu Leu Trp Leu Pro
  1               5                  10                  15

Asp Thr Thr Gly Glu Ile Val Leu Thr Gln Ser Pro Ala Thr Leu Ser
             20                  25                  30

Leu Ser Pro Gly Glu Arg Ala Thr Leu Ser Cys Arg Ala Ser Gln Ser
         35                  40                  45

Val Ser Ser Phe Leu Ala Trp Tyr Gln Gln Lys Pro Gly Gln Ala Pro
     50                  55                  60

Arg Leu Leu Ile Tyr Asp Ala Ser Asn Arg Ala Thr Gly Ser Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln Gln Arg Ser
            100                 105                 110

Asp Trp Pro Leu Thr Phe Gly Pro Gly Thr Lys Val Asp Ile Lys Arg
        115                 120                 125

Thr
```

<210> SEQ ID NO 24
<211> LENGTH: 490
<212> TYPE: DNA
<213> ORGANISM: Homo sapiens

<400> SEQUENCE: 24

```
tcgactacgg gggggctttc tgagagtcat ggatctcatg tgcaagaaaa tgaagcacct     60
gtggttcttc ctcctgctgg tggcggctcc cagatgggtc ctgtcccagc tgcagctgca    120
ggagtcgggc ccaggactgg tgaagccttc ggagaccctg tccctcacct gcactgtctc    180
tggtggctcc atcagcagta gtagttacta ctggggctgg gtccgccagc ccccagggaa    240
ggggctggag tggattggga gtatccatta gtgggagt actttctaca acccgtccct    300
caagagtcga gtcaccattt ccgtagacac gtccaagaac cagttctccc tgaagctgag    360
ctctgtgacc gccgcagaca cgactgtgta ttactgtgcg agacaggggt ctactgtggt    420
tcggggagtt tactactacg gtatggacgt ctggggccaa gggaccacgg tcaccgtctc    480
ctcagctagc                                                          490
```

<210> SEQ ID NO 25
<211> LENGTH: 154
<212> TYPE: PRT
<213> ORGANISM: Homo sapiens

<400> SEQUENCE: 25

```
Met Asp Leu Met Cys Lys Lys Met Lys His Leu Trp Phe Phe Leu Leu
 1               5                  10                  15
Leu Val Ala Ala Pro Arg Trp Val Leu Ser Gln Leu Gln Leu Gln Glu
            20                  25                  30
Ser Gly Pro Gly Leu Val Lys Pro Ser Glu Thr Leu Ser Leu Thr Cys
        35                  40                  45
Thr Val Ser Gly Gly Ser Ile Ser Ser Ser Tyr Tyr Trp Gly Trp
    50                  55                  60
Val Arg Gln Pro Pro Gly Lys Gly Leu Glu Trp Ile Gly Ser Ile His
 65                  70                  75                  80
Tyr Ser Gly Ser Thr Phe Tyr Asn Pro Ser Leu Lys Ser Arg Val Thr
                85                  90                  95
Ile Ser Val Asp Thr Ser Lys Asn Gln Phe Ser Leu Lys Leu Ser Ser
            100                 105                 110
Val Thr Ala Ala Asp Thr Thr Val Tyr Tyr Cys Ala Arg Gln Gly Ser
        115                 120                 125
Thr Val Val Arg Gly Val Tyr Tyr Tyr Gly Met Asp Val Trp Gly Gln
    130                 135                 140
Gly Thr Thr Val Thr Val Ser Ser Ala Ser
145                 150
```

<210> SEQ ID NO 26
<211> LENGTH: 423
<212> TYPE: DNA
<213> ORGANISM: Homo sapiens

<400> SEQUENCE: 26

```
agatctctca gttaggaccc agagggaacc atggaaaccc cagcgcagct tctcttcctc     60
ctgctactct ggctcccaga taccaccgga gaaattgtgt tgacgcagtc tccaggcacc    120
ctgtctttgt ctccagggga agagccacc  ctctcctgca gggccagtca gagtgttagc    180
agcagctact tagcctggta ccagcagaaa cctggccagg ctcccaggct cctcatctat    240
ggtgcatcca gcagggccac tggcatccca gacaggttca gtggcagtgg gtctgggaca    300
gacttcactc tcaccatcag cagactggag cctgaagatt ttgcagtgta ttactgtcag    360
cagtatggta gctcacctct gtacactttt ggccagggga ccaagctgga gatcaaacgt    420
acg                                                                  423
```

<210> SEQ ID NO 27
<211> LENGTH: 131
<212> TYPE: PRT
<213> ORGANISM: Homo sapiens

<400> SEQUENCE: 27

```
Met Glu Thr Pro Ala Gln Leu Leu Phe Leu Leu Leu Trp Leu Pro
 1               5                  10                  15
Asp Thr Thr Gly Glu Ile Val Leu Thr Gln Ser Pro Gly Thr Leu Ser
            20                  25                  30
Leu Ser Pro Gly Glu Arg Ala Thr Leu Ser Cys Arg Ala Ser Gln Ser
        35                  40                  45
Val Ser Ser Ser Tyr Leu Ala Trp Tyr Gln Gln Lys Pro Gly Gln Ala
```

```
                50                   55                   60
Pro Arg Leu Leu Ile Tyr Gly Ala Ser Ser Arg Ala Thr Gly Ile Pro
 65                  70                   75                   80

Asp Arg Phe Ser Gly Ser Gly Ser Gly Thr Asp Phe Thr Leu Thr Ile
                 85                   90                   95

Ser Arg Leu Glu Pro Glu Asp Phe Ala Val Tyr Tyr Cys Gln Gln Tyr
            100                  105                  110

Gly Ser Ser Pro Leu Tyr Thr Phe Gly Gln Gly Thr Lys Leu Glu Ile
            115                  120                  125

Lys Arg Thr
        130

<210> SEQ ID NO 28
<211> LENGTH: 489
<212> TYPE: DNA
<213> ORGANISM: Homo sapiens

<400> SEQUENCE: 28
ctcaacaacc acatctgtcc tctagagaaa accctgtgag cacagctcct caccatggac     60
tggacctgga ggatcctctt cttggtggca gcagctacaa gtgcccactc ccaggtgcag    120
ctggtgcagt ctggggctga gatgaagaag cctggggcct cagtcaaggt ctcctgcaag    180
acttctggat acaccttcac caattataag atcaactggg tgcgacaggc ccctggacaa    240
ggacttgagt ggatgggatg gatgaaccct gacactgata gcacaggcta tccacagaag    300
ttccagggca gagtcaccat gaccaggaac acctccataa gcacagccta catggagctg    360
agcagcctga gatctgagga cacggccgtg tattactgtg cgagatccta tggttcgggg    420
agttattata gagactatta ctacggtatg gacgtctggg gccaagggac cacggtcacc    480
gtctcctca                                                            489

<210> SEQ ID NO 29
<211> LENGTH: 145
<212> TYPE: PRT
<213> ORGANISM: Homo sapiens

<400> SEQUENCE: 29

Met Asp Trp Thr Trp Arg Ile Leu Phe Leu Val Ala Ala Ala Thr Ser
  1               5                   10                  15

Ala His Ser Gln Val Gln Leu Val Gln Ser Gly Ala Glu Met Lys Lys
                 20                  25                  30

Pro Gly Ala Ser Val Lys Val Ser Cys Lys Thr Ser Gly Tyr Thr Phe
             35                  40                  45

Thr Asn Tyr Lys Ile Asn Trp Val Arg Gln Ala Pro Gly Gln Gly Leu
         50                  55                  60

Glu Trp Met Gly Trp Met Asn Pro Asp Thr Asp Ser Thr Gly Tyr Pro
 65                  70                  75                  80

Gln Lys Phe Gln Gly Arg Val Thr Met Thr Arg Asn Thr Ser Ile Ser
                 85                  90                  95

Thr Ala Tyr Met Glu Leu Ser Ser Leu Arg Ser Glu Asp Thr Ala Val
            100                  105                  110

Tyr Tyr Cys Ala Arg Ser Tyr Gly Ser Gly Ser Tyr Tyr Arg Asp Tyr
            115                  120                  125

Tyr Tyr Gly Met Asp Val Trp Gly Gln Gly Thr Thr Val Thr Val Ser
        130                  135                  140

Ser
```

-continued

<210> SEQ ID NO 30
<211> LENGTH: 417
<212> TYPE: DNA
<213> ORGANISM: Homo sapiens

<400> SEQUENCE: 30

| gaggaactgc tcagttagga cccagaggga accatggaag ccccagctca gcttctcttc | 60 |
| ctcctgctac tctggctccc agataccacc ggagaaattg tgttgacaca gtctccagcc | 120 |
| accctgtctt tgtctccagg ggaaagagcc accctctcct gcagggccag tcagagtgtt | 180 |
| agcagctact tagcctggta ccaacagaaa cctggccagg ctcccaggct cctcatctat | 240 |
| gatgcatcca acagggccac tggcatccca gccaggttca gtggcagtgg gtctgggaca | 300 |
| gacttcactc tcaccatcag cagcctagag cctgaagatt ttgcagttta ttactgtcag | 360 |
| cagcgtagca actggccgct cactttcggc ggagggacca aggtggagat caaacga | 417 |

<210> SEQ ID NO 31
<211> LENGTH: 128
<212> TYPE: PRT
<213> ORGANISM: Homo sapiens

<400> SEQUENCE: 31

Met Glu Ala Pro Ala Gln Leu Leu Phe Leu Leu Leu Leu Trp Leu Pro
1               5                   10                  15
Asp Thr Thr Gly Glu Ile Val Leu Thr Gln Ser Pro Ala Thr Leu Ser
            20                  25                  30
Leu Ser Pro Gly Glu Arg Ala Thr Leu Ser Cys Arg Ala Ser Gln Ser
        35                  40                  45
Val Ser Ser Tyr Leu Ala Trp Tyr Gln Gln Lys Pro Gly Gln Ala Pro
    50                  55                  60
Arg Leu Leu Ile Tyr Asp Ala Ser Asn Arg Ala Thr Gly Ile Pro Ala
65                  70                  75                  80
Arg Phe Ser Gly Ser Gly Ser Gly Thr Asp Phe Thr Leu Thr Ile Ser
                85                  90                  95
Ser Leu Glu Pro Glu Asp Phe Ala Val Tyr Tyr Cys Gln Gln Arg Ser
            100                 105                 110
Asn Trp Pro Leu Thr Phe Gly Gly Gly Thr Lys Val Glu Ile Lys Arg
        115                 120                 125

<210> SEQ ID NO 32
<211> LENGTH: 497
<212> TYPE: DNA
<213> ORGANISM: Homo sapiens

<400> SEQUENCE: 32

| gagctctgag agaggagccc agccctggga ttttcaggtg ttttcatttg gtgatcagga | 60 |
| ctgaacagag agaactcacc atggagtttg gctgagctg cttttttctt gtggctattt | 120 |
| taaaaggtgt ccagtgtgag gtacagctgt tggagtctgg gggaggcttg gtacagcctg | 180 |
| ggaggtccct gagactctcc tgtgcagcct ctggattcac ctttagcagc tatgccatga | 240 |
| gctgggtccg ccaggctcca gggaaggggc tggagtgggt ctcagctatt agtggtagtg | 300 |
| gtggtagcag atactacgca gactccgtga agggccggtt caccatctcc agagacaatt | 360 |
| ccaagaacac gctgtatctg caaatgaaca gcctgagagc cgaggacacg gccgtatatt | 420 |
| actgtgcgaa agagagcagt ggctggttcg gggcctttga ctactggggc caggaaccc | 480 | tggtcaccgt ctcctca                                                      497

<210> SEQ ID NO 33
<211> LENGTH: 139
<212> TYPE: PRT
<213> ORGANISM: Homo sapiens

<400> SEQUENCE: 33

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Ser Ser Gly Trp Phe Gly Ala Phe Asp Tyr
        115                 120                 125

Trp Gly Gln Gly Thr Leu Val Thr Val Ser Ser
    130                 135

<210> SEQ ID NO 34
<211> LENGTH: 446
<212> TYPE: DNA
<213> ORGANISM: Homo sapiens

<400> SEQUENCE: 34
gatcttaaaa gaggttcttt ctctgggatg tggcatgagc aaaactgaca agtcaaggca    60
ggaagatgtc gccatcacaa ctcattgggt ttctgctgct ctgggttcca gcctccaggg    120
gtgaaattgt gctgactcag tctccagact tcagtctgt gactccaaag gagaaagtca    180
ccatcacctg ccgggccagt cagagcattg gtagtagctt acactggtac cagcagaaac    240
cagatcagtc tccaaagctc ctcatcaagt atgcttccca gtccttctca ggggtcccct    300
cgaggttcag tggcagtgga tctgggacag atttcaccct caccatcaat agcctggaag    360
ctgaagatgc tgcagcgtat tactgtcatc agagtagtag tttaccgatc accttcggcc    420
aagggacacg actggagatt aaacga                                          446

<210> SEQ ID NO 35
<211> LENGTH: 127
<212> TYPE: PRT
<213> ORGANISM: Homo sapiens

<400> SEQUENCE: 35

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
                20                  25                  30

Thr Pro Lys Glu Lys Val Thr Ile Thr Cys Arg Ala Ser Gln Ser Ile
            35                  40                  45

```
Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Ile Thr Phe Gly Gln Gly Thr Arg Leu Glu Ile Lys Arg
        115                 120                 125
```

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 36
tcttgtccac cttggtgttg ctgggcttgt g                              31

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 37
aggcacacaa cagaggcagt tccagatttc                                30

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 38
gatttaggtg acactatag                                            19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 39
taatacgact cactataggg                                           20

<210> SEQ ID NO 40
<211> LENGTH: 41
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 40
atcacagatc tctcaccatg gaagccccag ctcagcttct c                   41

```
<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 41
ggtgcagcca ccgtacgttt gatctccacc ttg                              33

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 42
gcgactaagt cgacaccatg gactggacct ggaggatc                         38

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 43
agagagagag gctagctgag gagacggtga cc                               32

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 44
ggtacgtgaa ccgtcagatc gcctgga                                     27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:Synthetic DNA

<400> SEQUENCE: 45
tctatataag cagagctggg tacgtcc                                     27
```